United States Patent
Schlaf et al.

(10) Patent No.: US 10,074,530 B1
(45) Date of Patent: *Sep. 11, 2018

(54) CARBON NANOTUBE ANCHOR FOR MASS SPECTROMETER

(71) Applicants: Rudiger Schlaf, Tampa, FL (US); Joshua Schumacher, Laurel, MD (US)

(72) Inventors: Rudiger Schlaf, Tampa, FL (US); Joshua Schumacher, Laurel, MD (US)

(73) Assignee: University of South Florida, Tampa, FL (US)

( * ) Notice: Subject to any disclaimer, the term of this patent is extended or adjusted under 35 U.S.C. 154(b) by 5 days.

This patent is subject to a terminal disclaimer.

(21) Appl. No.: 15/088,843

(22) Filed: Apr. 1, 2016

Related U.S. Application Data

(63) Continuation of application No. 14/094,057, filed on Dec. 2, 2013, now abandoned, which is a
(Continued)

(51) Int. Cl.
*H01J 49/04* (2006.01)
*C23C 16/455* (2006.01)
*H01J 49/16* (2006.01)

(52) U.S. Cl.
CPC ........ *H01J 49/0418* (2013.01); *C23C 16/455* (2013.01); *H01J 49/164* (2013.01)

(58) Field of Classification Search
USPC ....................................................... 250/282
See application file for complete search history.

(56) References Cited

U.S. PATENT DOCUMENTS 5,808,300 A * 9/1998 Caprioli ............. H01J 49/0004
250/281
6,858,197 B1 * 2/2005 Delzeit .................. B82Y 30/00
423/445 R (Continued)

OTHER PUBLICATIONS

Baro, M. et al. Pulsed PECVD for Low-temperature Growth of Vertically Aligned Carbon Nanotubes. Chem. Vap. Deposition 2014, 20, 161-169.
(Continued)

*Primary Examiner* — Phillip A Johnston
(74) *Attorney, Agent, or Firm* — Molly L. Sauter; Robert J. Varkonyi; Smith & Hopen, P.A.

(57) ABSTRACT

This invention enables a sensitivity enhancement in the detection of molecular compounds. A mass spectrometry analyte support with nanotube anchors are used to concentrate MALDI samples prepared with water-insoluble matrix compounds on the anchor spot. A matrix solution mixed with analyte molecules is spotted onto a specialized MALDI plate using carbon nanotubes to selectively nucleate the analyte. The spot diameter of the target is usually several orders of magnitude larger than traditional supports, and led to lateral concentration for non-aqueous based matrices and produced a final dried matrix/analyte spot that was approximately the diameter of the laser spot at the point of investigation. The carbon nanotubes enhance nucleation on specific areas of a sample plate to concentrate analyte/matrix deposit during droplet evaporation, and demonstrate an increase in signal to noise ratio and an improved detection capability of low analyte concentrations compared to the standard MALDI preparation technique.

19 Claims, 50 Drawing Sheets

Specification includes a Sequence Listing.

Related U.S. Application Data continuation-in-part of application No. 12/398,710, filed on Mar. 5, 2009, now Pat. No. 8,598,511.

(60) Provisional application No. 61/033,909, filed on Mar. 5, 2008.

(56) References Cited

U.S. PATENT DOCUMENTS

| | | | |
|---|---|---|---|
| 7,465,921 B1* | 12/2008 | Joyce | H01J 49/0418 250/281 |
| 7,492,088 B2* | 2/2009 | Jang | B82Y 10/00 313/311 |
| 7,735,147 B2* | 6/2010 | Jin | G01Q 60/38 73/105 |
| 2004/0043497 A1* | 3/2004 | Feuer | B82Y 30/00 422/261 |
| 2006/0097150 A1* | 5/2006 | Joyce | B82Y 10/00 250/288 |

OTHER PUBLICATIONS

Garg, R.K. et al. Effects of Feed Gas Composition and Catalyst Thickness on Carbon Nanotube and Nanofiber Synthesis by Plasma Enhanced Chemical Vapor Deposition. Journal of Nanoscience and Nanotechnology, vol. 8, 3068-3076, 2008.

Meyyappan, M. et al. Carbon nanotube growth by PECVD: a review. Plasma Sources Sci. Technol. 12(2003) 205-216.

\* cited by examiner

α-cyan-hydroxycinnamic acid
(αCHCA)

dihydroxy benzoic acid
(DHB)

hydroxy picolinic acid
(HPA)

SEQUENCE LISTING

```
<160> NUMBER OF SEQ ID NOS: 4

<210> SEQ ID NO 1
<211> LENGTH: 8
<212> TYPE: PRT
<213> ORGANISM: Homo sapiens

<400> SEQUENCE: 1

Pro Pro Gly Phe Ser Pro Phe Arg
1               5

<210> SEQ ID NO 2
<211> LENGTH: 10
<212> TYPE: PRT
<213> ORGANISM: Homo sapiens

<400> SEQUENCE: 2

Asp Arg Val Tyr Ile His Pro Phe His Leu
1               5                  10

<210> SEQ ID NO 3
<211> LENGTH: 14
<212> TYPE: PRT
<213> ORGANISM: Homo sapiens

<400> SEQUENCE: 3

Glu Gly Val Asn Asp Asn Glu Glu Gly Phe Phe Ser Ala Arg
1               5                  10

<210> SEQ ID NO 4
<211> LENGTH: 17
<212> TYPE: PRT
<213> ORGANISM: Homo sapiens

<400> SEQUENCE: 4

Ser Tyr Ser Met Glu His Phe Arg Trp Gly Lys Pro Val Gly Lys Lys
1               5                  10                  15

Arg
```

CARBON NANOTUBE ANCHOR FOR MASS SPECTROMETER

CROSS REFERENCE TO RELATED APPLICATION

This application is a continuation application of U.S. Nonprovisional application Ser. No. 14/094,057, entitled "Carbon Nanotube Anchor for Mass Spectrometer", filed on Dec. 2, 2013, which is a continuation-in-part of U.S. Nonprovisional patent application Ser. No. 12/398,710, entitled "Carbon Nanotube Anchor for Mass Spectrometer", filed on Mar. 5, 2009, which claims priority to U.S. Provisional Patent Application No. 61/033,909, entitled "Carbon Nanotube Anchor for Mass Spectrometer", filed on Mar. 5, 2008, the contents of which are herein incorporated by reference.

FIELD OF INVENTION

This invention relates to mass spectrometer sample anchors. Specifically, the invention is a carbon nanotube anchor plate for water insoluble samples in matrix assisted laser desorption ionization mass spectrometers.

BACKGROUND OF THE INVENTION

Mass spectrometry (MS) is a sensitive procedure to measure the masses of particles and chemical compounds, such as biomolecules like proteins, peptides, DNA. However, biomolecules require specialized techniques to enable desorption and ionization of the molecules while keeping them intact, such as matrix-assisted laser desorption/ionization mass spectrometry (MALDI-MS).

In the MALDI process, a matrix is used to protect and assist in ionization by donating charge to the analyte biomolecules when excited by the laser. The matrix consists of crystallized molecules specific to the type of analyte to be investigated. The most common matrices used today are based on benzoic or cinnamic acids and absorb light with wavelengths below 350 nm. In most sample preparation procedures, the matrix is first dissolved in the appropriate solvent (de-ionized water, various organic solvents, etc.), then mixed with solution containing the analyte molecules.

There are five main types of matrix, seen in FIGS. 1(A) through (E), with their use is determined by the type of molecule to be investigated. For investigating proteins, sinapinic (Beavis, & Bridson, *Epitaxial Protein Inclusion in Sinapic Acid Crystals*. Journal of Physics D-Applied Physics, 1993. 26(3): p. 442-447) and ferulic acids are typically used. For peptides, sinapinic acid, α-cyanohydroxycinnamic acid (CHCA), (Beavis, et al., *Alpha-Cyano-4-Hydroxycinnamic Acid as a Matrix for Matrix-Assisted Laser Desorption Mass-Spectrometry*. Organic Mass Spectrometry, 1992. 27(2): p. 156-158) and dihydroxy benzoic acid (DHB) (Strupat, et al., *2,5-Dihydroxybenzoic Acid—a New Matrix for Laser Desorption Ionization Mass-Spectrometry*. International Journal of Mass Spectrometry and Ion Processes, 1991. 111: p. 89-102) are used. For oligonucleotides and DNA probes, DHB and hydroxy picolinic acid (HPA) are used. The natural state of the matrix molecules is a crystalline form, and is dissolved in an appropriate solvent (typically highly purified water and an organic solvent such as acetonitrile) for use.

There are two main types of sample preparation, sequential deposition in which the matrix solution is deposited on the MALDI plate and allowed to crystallize before the analyte solution is deposited on top (Dai, et al., *Two-layer sample preparation: A method for MALDI-MS analysis of complex peptide and protein mixtures*. Analytical Chemistry, 1999. 71(5): p. 1087-1091), and concurrent deposition where the matrix and analyte solutions are mixed before deposition. In the latter technique, the analyte is distributed throughout the matrix and is said to be co-crystallized. The sequential deposition technique has the advantage of increased analyte concentration on the surface of the matrix crystals, if the matrix is not entirely re-dissolved upon analyte application. However, sample homogeneity is affected due to the lack of analyte in the bulk of the matrix crystals, leading to signal degradation over time with increased laser investigation of the same sample spot. The co-crystallization technique produces matrix crystals with a more uniform concentration of embedded analyte, which produces more consistent ion signals over time.

The resultant solution is deposited onto a MALDI plate, where the matrix re-crystallizes with the analyte as the solvents evaporate thereby forming a spot, through a process called co-crystallization.

For analysis, the plate is loaded into the MALDI instrument and subjected to a vacuum, followed by laser stimulation. It should be noted that atmospheric pressure MALDI is also possible, but has limitations in sensitivity and mass range. The energy from the laser is absorbed by the matrix, which transfers charge to the analyte, generating plumes of both matrix and analyte molecules that are desorbed from the plate surface. Ideally, the matrix should desorb from the sample surface without destructively heating the analyte. Ionization is assumed to occur at the sample surface and in the initial stages of the resulting plume of molecules. The ionized analyte molecules are detected by a time-of-flight (TOF) mass spectrometer and the data is plotted in a graph of intensity vs. mass-to-charge ratio.

When the matrix molecules reach the desorption temperature, which is based on the matrix, the molecules are liberated from the sample surface at velocities above 600 m per second. Because the desorption is primarily dependent on the electron excitation, increasing the laser fluence considerably above the plume generation threshold can lead to excessive matrix desorption and increased noise in a sample spectra. The energy and diameter of the laser used for plume generation can be factors in instrument resolution as a result of differing plume dynamics. Additionally, the expansion of the matrix plume might be influenced by charges that the molecules carry as a result of being excited by the primary laser.

Evaporation speed is also a factor in sample preparation. It has been observed that fast evaporation produces high density fields of smaller crystals (Beeson, et al., *Aerosol Matrix-Assisted Laser-Desorption Ionization-Effects of Analyte Concentration and Matrix-to-Analyte Ratio*. Analytical Chemistry, 1995. 67(13): p. 1981-1986). This can lead to an increase in surface area available for laser absorption and analyte desorption compared to the larger matrix crystals that are obtained through slow evaporation. Crystal density on the sample spot can have an effect on the MALDI spectra. An increased number of crystals in contact can increase the energy pooling efficiency resulting in increased analyte ionization at the crystal surface.

However, in current sample preparation the dried mixture of matrix and analyte has been shown to be non-homogenous, most likely a result of separation of the two substances during crystallization. This increases the number of investigations required to get an accurate average of the analyte signal.

Droplet deposition on traditional metal substrates resulted in nonhomogeneous dried droplets with a majority of the matrix crystals forming a ring around the edge and a central area that was either blank or contained microcrystals, which is consistent with the results found in this work when using this technique. One of the techniques designed to decrease sample spot size is the use of patterned areas using hydrophobic and hydrophilic materials. Schuerenberg (Schuerenberg, et al., *Prestructured MALDI-MS sample supports*. Analytical Chemistry, 2000. 72(15): p. 3436-3442) published results using a substrate composed of a hydrophobic Teflon® field with an array of hydrophilic gold spots to act as sample anchors. The sample supports used in the experiment consisted of a stainless steel sample plate coated with polytetrafluoroethylene (PTFE, or commonly known as Teflon®) to a thickness between 30-40 µm. Gold spots were deposited via sputtering to a thickness of 30 nm, with spot diameters ranging from 100-300 µm (Schuerenberg, et al., *Prestructured MALDI-MS sample supports*. Analytical Chemistry, 2000. 72(15): p. 3436-3442), which are considerably smaller than the diameter of the samples prepared using the traditional dried droplet technique (approaching 1 mm diameter, depending on solution composition, concentrations, and deposition volume). Since the typical laser used in MALDI-MS instruments has a diameter typically between 100-200 µm, the objective of the technique is lateral concentration of the sample onto the anchor spot. Solutions containing matrices 2,5-dihydroxybenzoic acid (DHB) or 3-hydroxypicolinic acid (3-HPA) were deposited via pipette onto the patterned 200 µm. When 3-HPA matrix-samples exceeded the gold spot diameter, thought to be a result of excess matrix material in solution. The author also reported in several instances the shrinking sample droplet would leave the gold spot and crystallize on the surrounding Teflon surface. Investigations with the 300 µm diameter gold spots revealed that the drying crystals resulted in structures that resembled those on plain metal, with a thicker crystalline rim and a blank center area. This was thought to be a result of insufficient matrix concentration in solution, as this phenomenon was avoided by increasing the matrix concentration previous to droplet deposition (Schuerenberg, et al., *Prestructured MALDI-MS sample supports*. Analytical Chemistry, 2000. 72(15): p. 3436-3442). As such, matrix composition and concentration are critical for successful concentration during drying.

Carbon nanotubes (CNTs) are one of the many different occurring forms (or allotropes) of the element carbon, comprising tubular structures composed entirely of carbon atoms that are joined with 120° bond angles that resemble rolled up sheets of grapheme (Dresselhaus, et al., *Carbon-Fibers Based on C-60 and Their Symmetry*. Physical Review B, 1992. 45(11): p. 6234-6242). CNT's can be single tube (single-walled) or multiple tubes inside each other (multi-walled), according to the type of growth process. Each wall can be classified as "armchair", "zigzag" or "chiral" depending on the orientation of the carbon bond angles with respect to the diameter of the tube (Dresselhaus, et al., *Physics of Carbon Nanotubes*. Carbon, 1995. 33(7): p. 883-891). Each type has characteristic properties such as minimum diameter and electron conductivity. The conductivity of the carbon nanotube is also determined by the chiral vector (Saito, R., et al., *Electronic-Structure of Chiral Graphene Tubules*. Applied Physics Letters, 1992. 60(18): p. 2204-2206). Depending on the lattice unit cell, CNTs can behave as a metal or semiconductor. CNTs with armchair structure behave as a metal, while zigzag and chiral CNTs can behave as either a metal or semiconductor depending on the vector. For carbon nanotubes that consist of multiple walls, each wall can have its own chiral vector and electronic properties. However in practice, multi-walled CNTs usually display metallic properties, as one of the shells has a chiral vector consistent with metallic properties, hence dominating conduction when the entire nanotube is measured.

Matrix assisted laser desorption ionization mass spectrometry (MALDI-MS) is a technique used for the quantification and detection of bio-molecules and other macromolecular substances for applications ranging from proteomics and cancer early detection to forensic investigations. Especially for proteomics and cancer research, sensitivity and analyte concentration are essential for successful measurements, since the analyte is often only available in very small quantities and/or high dilution.

The described invention aims at increasing the reproducibility and sensitivity of MALDI-MS for water-insoluble matrix based samples through improving the sample preparation process. MALDI-MS is an advanced mass spectrometry technique used to detect large molecules ("macromolecules"). Such molecules cannot be measured using conventional mass spectrometry techniques due to fragmentation. MALDI-MS achieves ionization by proton transfer from a matrix compound (usually a crystal-forming acid) to the analyte to be analyzed. To achieve this proton transfer, the analyte needs to be embedded within the matrix compound, which generally exceeds the analyte amount by two to three magnitudes. This is achieved by creating a mixed solution of both analyte and matrix, which is drop-deposited on a sample plate. Evaporation results in a solid residue of analyte/matrix compound. This solid residue is then ablated with a laser focused into a tight (~100 µm diameter) high-intensity spot. The ablated material forms a gaseous cloud above the sample in which protons are transferred from matrix to analyte, resulting in charging of the analyte molecules, which can subsequently be analyzed in the mass spectrometer by use of electrical or magnetic fields.

The standard matrix materials used in MALDI investigations can be generally divided into water-soluble and water-insoluble compounds. The mostly used water-soluble compounds are 2,5-dihydroxybenzoic acid (2,5-DBH) and 3-hydroxypicolinic acid (3-HPA), while the most popular water-insoluble material is α-cyano-4-hydroxycinnamic acid (HCCA).

Since drop-deposition of matrix/analyte solution on a flat plate typically yields irregular circular deposits, such deposits are difficult to analyze. Usually a trial and error procedure is used to find a "sweet spot" that yields a good signal-to-noise ratio. This is time consuming, and yields poorly reproducible data. Consequently, this has led to the invention of so-called anchor plates, where arrays of small (100-800 µm diameter) hydrophilic spots are created on a hydrophobic substrate. This allows deposited droplets to anchor to the hydrophilic spots, since they are repelled by the hydrophobic surroundings. Successively, evaporation results in crystallization of the matrix/analyte deposit on or close to the hydrophilic spot. This allows a much more reproducible interrogation of the sample since the laser spot covers a larger portion of the area coated with the matrix/analyte deposit. This eliminates the hunt for the "sweet spot", while also increasing the sensitivity of the measurement due to the analyte concentration effect of the procedure (Schuerenberg, C. Luebbert, H. Eickhoff, M. Kalkum, H. Lehrach and E. Nordhoff: "Prestructured MALDI-MS sample supports", Analytical Chemistry 72 (15), pp. 3436-3442 (2000).).

This procedure works reliably with water-soluble matrix compounds such as 2,5-DHP or 3-HPA, while it does not work well with water-insoluble matrix compounds such as HCCA (Schuerenberg, C. Luebbert, H. Eickhoff, M. Kalkum, H. Lehrach and E. Nordhoff: "Prestructured MALDI-MS sample supports", Analytical Chemistry 72 (15), pp. 3436-3442 (2000); M. Schuerenberg: "AnchorChip™ Technology, Revision 2.3", Bruker Product Information, (2005)). When HCCA is used, the final deposit is spread over an area much wider than the anchor spot. The reason for this behavior lies in the necessity to use an organic solvent mixable with water to dissolve the HCCA matrix. Usually, acetonitrile is used as organic solvent since it dissolves HCCA, and it is polar enough to mix well with the aqueous solution containing the analyte to be investigated.

However, the current laser-based mass spectrometry supports are unable to reliably deposit or concentrate samples having micro-liter volume and suffer from high signal to noise ratios below a threshold analyte concentration. The present invention addresses these issues through a novel device designed to nucleate analyte at a specific, predetermined location.

SUMMARY OF THE INVENTION

When HCCA is used, the final deposit is spread over an area much wider than the anchor spot. The reason for this behavior lies in the necessity to use an organic solvent mixable with water to dissolve the HCCA matrix. Usually, acetonitrile is used as organic solvent since it dissolves HCCA, and it is polar enough to mix well with the aqueous solution containing the analyte to be investigated. Since the organic solvent has a higher vapor pressure than water, it evaporates first after the droplet is deposited. This creates a supersaturation situation for the matrix molecules, causing them to precipitate on the area surrounding the anchor spot since the drop is still relatively large at that point, while in the same time collapsing due to the increased concentration. At the end of the evaporation process an area much larger than that of the anchor spot is coated with deposit, similar to drop depositions on a standard (non-anchor stainless steel) plate. On such a deposit the laser spot can again only interrogate a small fraction of the total deposit. Hence most of the analyte is never analyzed by the mass spectrometer, limiting the total achievable sensitivity.

The invention addresses this issue by introducing an additional feature to provide an anchor spot more conducive to nucleation of the matrix compound than the surrounding area, and precipitation on the surrounding area due to supersaturation could be avoided. The inventive mass spectrometry analyte support comprises at least one analyte anchor disposed on the analysis face of a support wafer. This results in deposition exclusively on the anchor spot during the initial organic solvent evaporation phase, even if the droplet originally covered a larger area than the anchor spot. In some embodiments, the support wafer is a silicon wafer, and may optionally be coated with a hydrophobic material. The analyte anchors disposed on the support wafer optionally comprise a plurality of nanotubes, which may be carbon nanotubes. Thus a plurality of carbon nanotube based anchoring spots are located on the silicon support for organic solvent containing MALDI samples, which result in the concentration of water-insoluble matrix based MALDI samples on a suitable anchor spot.

A patch of aligned carbon nanotubes grown by plasma enhanced chemical vapor deposition (PECVD) on a standard Si wafer were tested as an anchoring spot. A catalyst (usually Ni) was used to enable carbon nanotube growth. Patterning of the catalyst allows the definition of areas with and without nanotube growth. This was utilized for the invention through mask-based patterning of 150 μm diameter Ni patches subsequently subjected to PECVD growth of nanotubes (the size of the patches is only limited by the patterning resolution available). The nanotube arrays were shown to act as anchoring surfaces for analyte/water-insoluble matrix solutions (for pure water carbon nanotubes actually act as hydrophobic surfaces, probably due to the higher surface tension of pure water), thereby anchoring the deposited drop since the nanotube spot is surrounded by hydrophobic native Si oxide.

Carbon nanotube spots not only anchor the deposited drop, but they also act as nucleation centers causing early nucleation of the analyte/matrix compound on top of the nanotube array as the droplet evaporates. This prevents supersaturation of the solution, and therefore strongly reduces deposition on areas surrounding the nanotube spots (see below for further description). In some embodiments, these nanotubes are aligned with the other nanotubes, and specifically may be carbon nanotubes aligned with the other carbon nanotubes.

Also disclosed in a method of creating a mass spectrometry analyte support. A metal catalyst is deposited on the analysis face of a MALDI support wafer, such as a silicon wafer, having a diameter of from 150 μm to 200 μm. Optionally, the support wafer is rinsed prior to use in acetone, isopropyl alcohol, then methanol followed by drying with nitrogen. During deposition of the metal catalyst, the catalyst may optionally be annealed to the support wafer by warming the support wafer-metal catalyst to about 200° C. for 24 hours. Exemplary metal catalyst include iron, iron and molybdenum, cobalt, cobalt and molybdenum, and nickel. In certain embodiments, the metal catalyst is applied to the support wafer at 10 nm to 40 nm thick, in particular 20 nm thick. The catalyst is optionally deposited using electron beam deposition, such as using a 270° deflection of the electron beam source from the crucible. The electron beam deposition may be performed at $1 \times 10^{-6}$ Torr.

The ambient pressure surrounding the support wafer is reduced and the wafer exposed to ammonia and a carbon source. Exemplary carbon sources include methane, carbon oxide, hexane, acetylene, carbon dioxide, benzene, and ethanol. In some variations, the ammonia and the carbon source are introduced at an ammonia to carbon source ratio of 4:1. Aligned carbon nanotubes were then grown perpendicular on the support wafer using plasma enhanced chemical vapor deposition. Optionally, the plurality of aligned carbon nanotubes are grown at a temperature between 500° C. and 1200° C. Further, in particular embodiments, the ambient pressure was reduced to $1 \times 10^{-3}$ Torr for growth of the carbon nanotubes. The support wafer with plurality of aligned carbon nanotubes is allowed to cool to room temperature in vacuum in specific embodiments.

Also disclosed is a method of analyzing an analyte sample. A water-insoluble matrix, such as HCCA, is first dissolved in an organic solvent, such as acetonitrile, and analyte added to the matrix-solution. The dissolved analyte-matrix solution is then applied to the mass spectrometry analyte support, described above. The dissolved analyte-matrix solution is nucleated on the support wafer, such as by allowing the solution to evaporate, thereby forming concentrated analyte locales on the nanotube anchors. In certain embodiments, the nanotube anchors are aligned carbon nanotubes.

The analyte-matrix solutes remaining from the analyte-matrix solution are lased, producing a gas which is then analyzed. The sample may be lased using a nitrogen laser, however any lasers known in the art for use in mass spectrometry analysis may be used in this invention.

The inventions disclosed herein were tested using drop-deposition of identical 0.2 µL aliquots of 250 fmol/µL peptide standard solution (Mariner CALMIX 1—consisting of des-Arginine-Bradykinin, Angiotensin I, Glu-Fibrinopeptide, and Adrenocorticotropic Hormone (ACTH); Applied Biosystems (Foster City, Calif.)) mixed with HCCA matrix compound at a strength of 3 mg/ml on a conventional Bruker "anchor plate" (M. Schuerenberg: "AnchorChip™ Technology, Revision 2.3", Bruker Product Information, (2005)), and on the invention, a carbon nanotube based "nucleation enhancing" anchor spot. It was noted that the experiment on the nanotube spot had a slightly different matrix concentration of 2.5 mg/ml. The analyte deposit was analyzed for the conventional anchor sample plate, where a 200 µm diameter anchor spot was visible in the top left quadrant of the deposited residue, indicated by a circle. Of particular note, the matrix/analyte deposit was considerably larger (~0.8 mm diameter) than the anchor spot. In contrast, deposition on the carbon nanotube anchor spot resulted in an almost complete concentration of the analyte/matrix crystals onto the ~150 µm diameter nanotube area, where most of the deposit is crystallized on top of the carbon nanotubes.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Disclosed is a mass spectrometry analyte support, which is useful in performing various analysis procedures, such as MALDI-TOF. The device promotes the nucleation of analyte on a discrete location on the analyte support, increasing sensitivity and consistency and decreasing analysis time.

As used herein, the term "morphology" refers to the form and structure of an object, typically a film or particle.

As used herein, the term "profilometer" refers to an instrument that uses a stylus to measure the profile of a surface. The vertical resolution of the instrument is typically in the nanometer range.

As used herein, the term "supersaturation" refers to a solution that contains a dissolved amount of material greater than the standard maximum under normal circumstances. Supersaturation can occur when an initial condition of a solution is changed such as a reduction in temperature or change in solvent composition due to evaporation.

As used herein, the term "isoelectric point" (pI) is the pH value at which no net electrical charge exists on a molecule.

As used herein "substantially" means almost wholly within the specified characteristics. Where the term is used to designate a purity amount, substantially pure means at least 90% pure, more preferably more than 95% pure, and most preferably more than 99.9% pure.

As used herein "metal in elemental form or an alloy having typical metallic properties, such as electrical conductivity As used herein "catalyst island" means a patterned structure comprised of catalyst material.

As used herein "perpendicular" means the longitudinal axis of the specified element is at a right angle to a specified plane or secondary element.

As used herein "nanotube" means a structure at least partially having a cylindrical structure with at least one dimension being in the nanometer size, i.e. below 1 μm.

Example 1

The Plasma-Enhanced Chemical Vapor Deposition (PECVD) growth was used to permit strict control of growth location and creation of well-defined areas of carbon nanotubes. Electron beam evaporation was used to deposit a nickel catalyst onto the substrate to create samples for carbon nanotube growth. Nickel pellets of 99.9% purity (Alfa Aesar, Ward Hill, Mass.) and placed in a new crucible liner (MDC Vacuum Products, Hayward, Calif.). The device used a 270° deflection of the electron beam source from the crucible, preventing the electron beam from being coated with target material, and concurrently permits beam focusing and beam shifting/scanning.

Figure 1A:
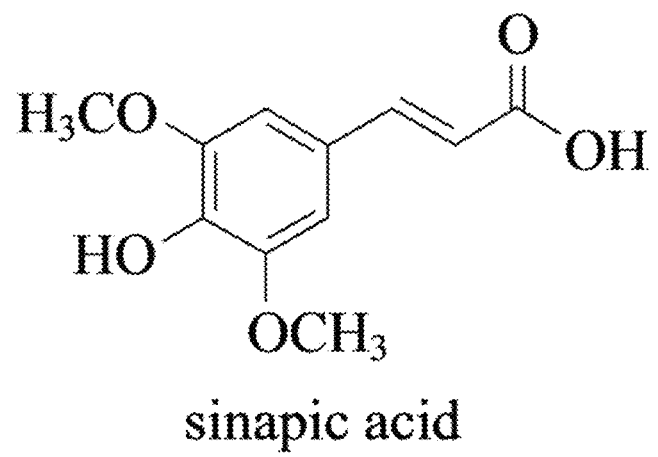
FIG. 1A is a chemical structures of the commonly used matrix molecule, sinapic acid.
Figure 1B:
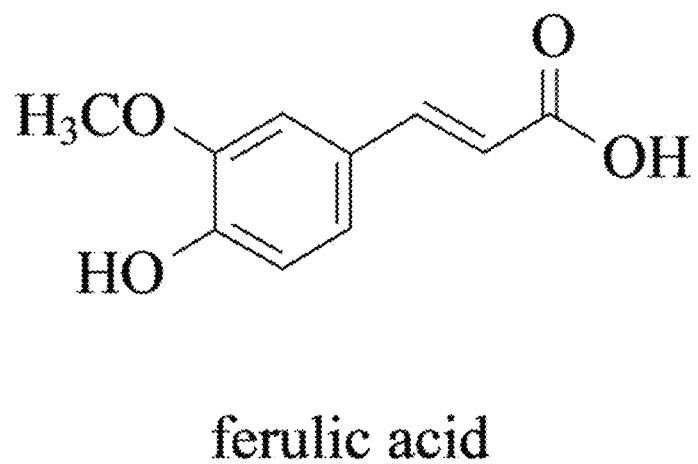
FIG. 1B is a chemical structures of the commonly used matrix molecule, ferulic acid.
Figure 1C:
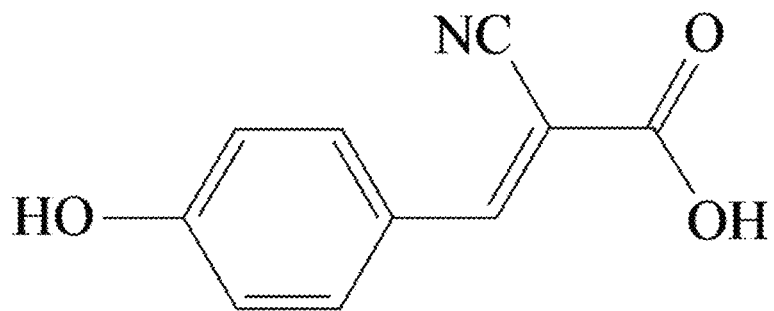
FIG. 1C is a chemical structures of the commonly used matrix molecule, α-cyan-hydroxycinnamic acid.
Figure 1D:
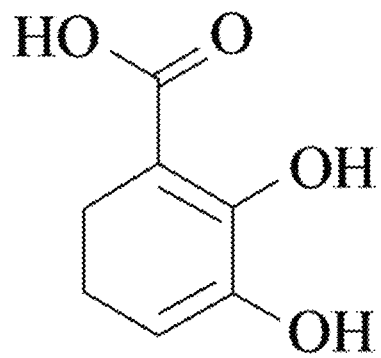
FIG. 1D is a chemical structures of the commonly used matrix molecule, dihydroxy benzoic acid.
Figure 1E:
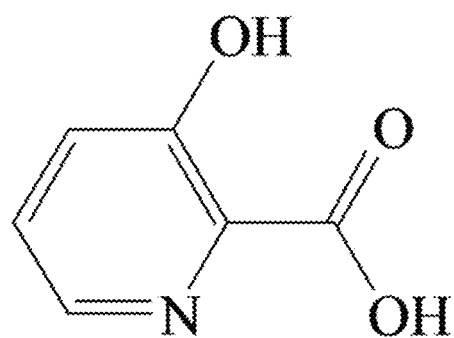
FIG. 1E is a chemical structures of the commonly used matrix molecule, hydroxyl picolinic acid.
Figure 2A:
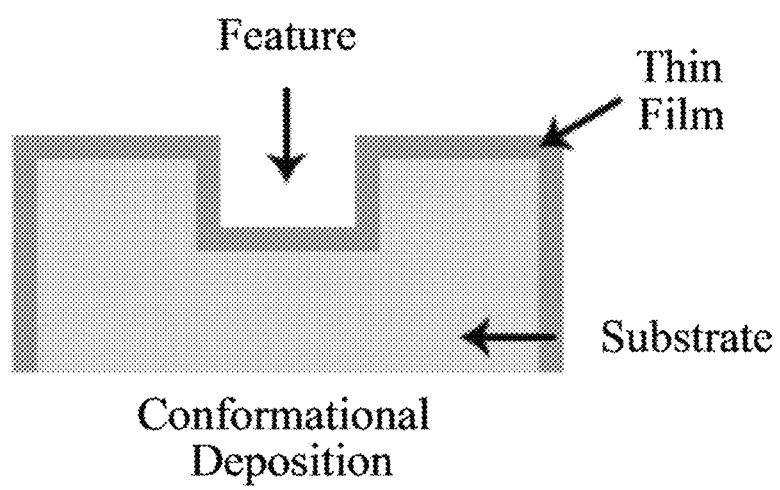
FIG. 2A is an illustration of sidewall coverage for conformal deposition.
Figure 2B:
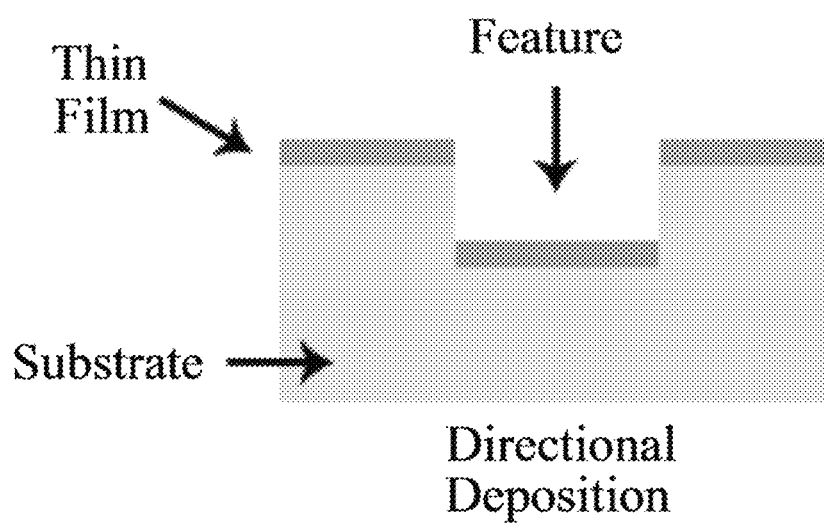
FIG. 2B is an illustration of sidewall coverage for directional deposition.
Figure 3:
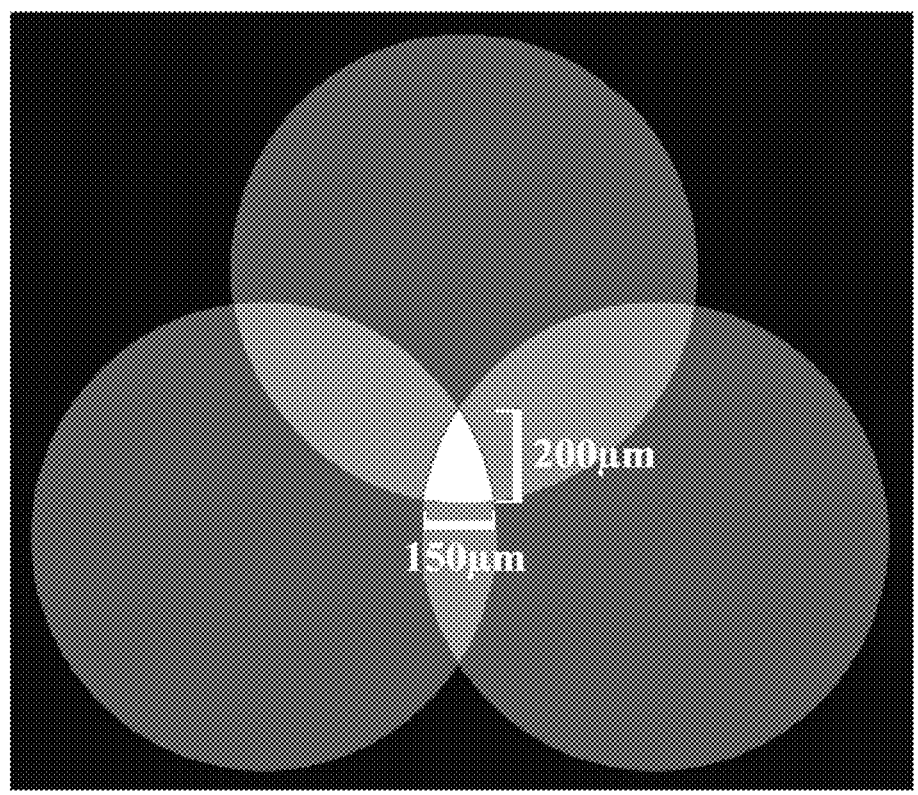
FIG. 3 is an illustration of the triple mask overlap forming a window with dimensions 200×150 µm.
Figure 4:
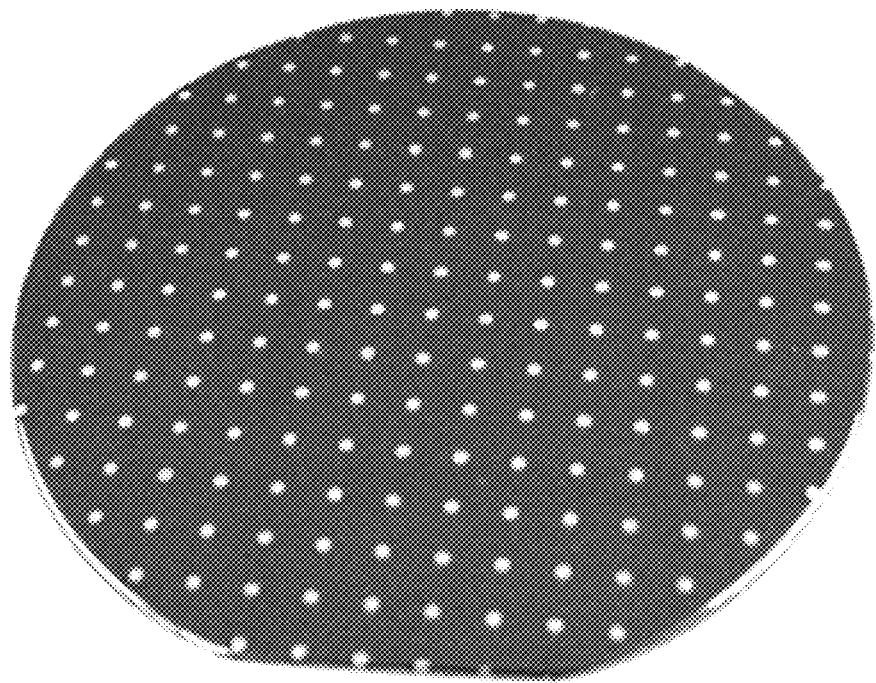
FIG. 4 is an image of a silicon wafer with 1 mm patterned nickel deposits (lighter spots). Image only for reference as the smaller nickel deposits were difficult to photograph.
Figure 5A:
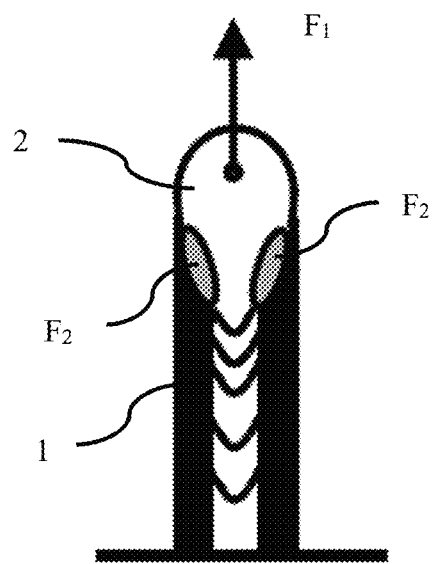
FIG. 5A is an illustration showing the alignment mechanism for tip growth.
Figure 5B:
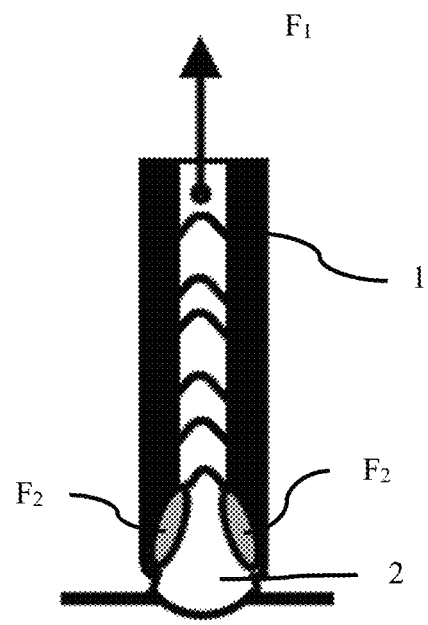
FIG. 5B is an illustration showing the alignment mechanism for root growth.
Figure 5C:
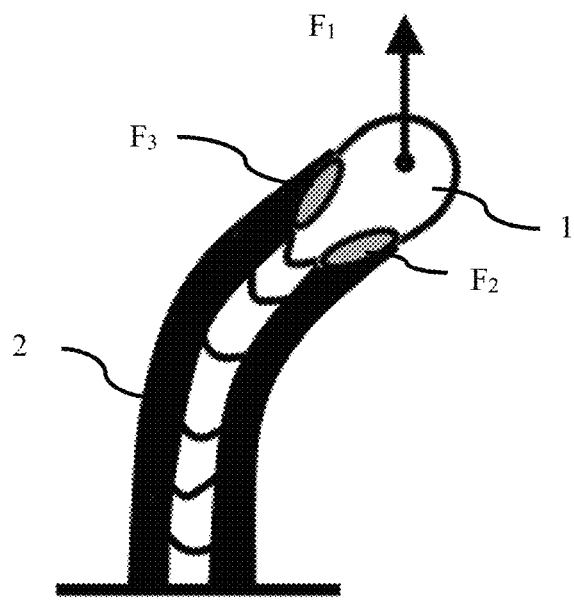
FIG. 5C is an illustration showing the alignment mechanism for tip growth illustrating that misalignment during growth causes a restoration force in the case of tip growth.
Figure 5D:
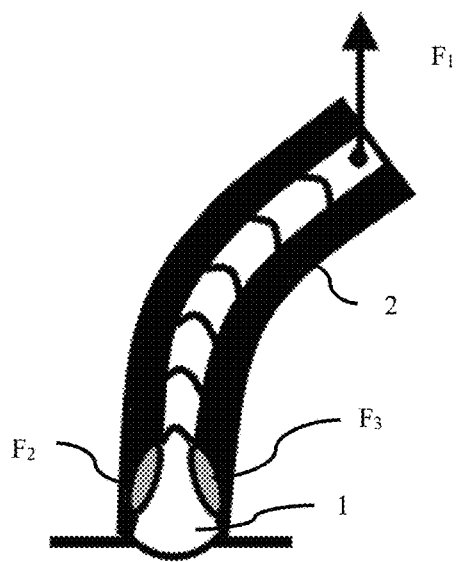
FIG. 5D is an illustration showing the alignment mechanism for root growth illustrating that misalignment during growth does not cause a restoration force in the case of root growth.

An advantage of chemical deposition, the deposited film is typically conformal to the sample surface, meaning a nearly uniform film thickness regardless of surface features, as seen in FIG. 2(A). A combination of three physical masks with rectangular grids of 1 mm diameter holes (with 3.3 mm grid spacing) were overlapped to form an opening that was approximately 200 μm tall by 150 μm wide, as seen in FIG. 3. This was placed in contact with the front of the silicon wafer (in the direction of the evaporation source) and used to pattern the nickel. A Varian Semiconductor (Gloucester, Mass.) model 980-2462 electron beam evaporator was used to deposit the nickel onto an n-type (111) silicon wafer that was cleaned using a standard sequential rinse of acetone, isopropyl alcohol, and methanol and dried with nitrogen. The wafer was placed in the evaporator's vacuum chamber which was then pumped down to high vacuum ($1 \times 10^{-6}$ Torr) using a combination of roughing, turbo-molecular, and cryogenic pumps (O'Hanlon, *A User's Guide to Vacuum Technology.* 3rd ed. 2003, New York, N.Y.: Wiley-Interscience. 536). The pressure was measured using a Varian Semiconductor model 845 ion gauge/controller. A high voltage of 10.5 kV was applied to the electron emitter and the emission current was continuously adjusted to provide a stable 1.5 Å (Angstroms) per second deposition rate as measured by a Sigma Instruments (Fort Collins, Colo.) SQM-160 quartz crystal thickness monitor placed in vacuum near the silicon wafer. The final deposition thickness was approximately 20 nm as measured using a Dektak 3030ST surface profilometer (Veeco Instruments Inc., Plainview, N.Y.). The result was a silicon wafer with nickel deposits approximately 20 nm in height surrounded by clean silicon, seen in FIG. 4. These samples were used in the PECVD chamber to create small patches of carbon nanotubes for MALDI sample concentration experiments.

Carbon nanotube growth was accomplished with a prototype PECVD reactor, built in-house using ultra high vacuum components sourced from Kurt J. Lesker Company (Clairton, Pa.) and MDC Vacuum Products (Hayward, Calif.). Plasma-enhanced chemical vapor deposition (PECVD) (Bower, et al., *Plasma-induced alignment of carbon nanotubes.* Applied Physics Letters, 2000. 77(6): p. 830-832; Han, et al., *Effects of growth parameters on the selective area growth of carbon nanotubes.* Thin Solid Films, 2002. 409(1): p. PII S0040-6090(02)00115-3; Ren, et al., *Synthesis of large arrays of well-aligned carbon nanotubes on glass.* Science, 1998. 282(5391): p. 1105-1107) was used as it allows control over location and the alignment of the grown CNT relative to the substrate surface.

The wafer with patterned nickel was manually diced into pieces approximately 1 cm² using a diamond-tipped scribe (Ted Pella Inc., Redding, Calif.). A single layer of the catalyst-coated silicon substrate was placed onto a machined copper substrate heater in the center of the reactor grounded, and the base pressure reduced to approximately 1 milli-Torr ($1 \times 10^{-3}$ Torr) to evacuate atmospheric gasses with an Edwards (Tewksbury, Mass.) model 30 two-stage roughing pump. Vacuum was measured with an Edwards Barocel 600 series capacitance manometer rather than traditional filament-based gauges because of the corrosive environment (e.g. hot gaseous ammonia) inside the reactor during operation. Simultaneously, the substrate was heated to approximately 600° C. using Omega Engineering (Stamford, Conn.) CSH series stainless steel cartridge heaters powered by a Sorensen (division of Ametek Programmable Power Inc., San Diego, Calif.) model DCS 150-20 direct current power supply. Temperature was measured using a JK type thermocouple attached to the side of the substrate heating stage and connected to an Omega CNi series programmable temperature controller. The measured temperature was previously calibrated to the sample temperature to ensure correct measurement since direct measurement is not possible during CNT growth due to interference from the upper high-voltage electrode and resulting plasma. Optionally, the substrate can be heated to between 500-1000° C.

Once the sample temperature reached the target and stabilized, gaseous ammonia ($NH_3$, Anhydrous grade 4) and acetylene ($C_2H_2$, Atomic Absorption grade) (both supplied by Airgas, Radnor, Pa.) were introduced into the reactor from storage tanks through a system of mass flow controllers (MFC) sourced from Unit Instruments Inc. (Yorba Linda, Calif.) model UFC-1660 connected to a model URS-100-5 MFC controller. The ammonia to acetylene ratio for successful CNT growth in this reactor was found to be 4:1 with a combined flow of 500 standard cubic centimeters per minute (SCCM) as controlled by the MFCs. Chamber pressure during the growth phase is held constant at a value between 2-3 Torr by the use of a throttling valve on the line between the chamber and the roughing pump. Once the target pressure was achieved, a DC high voltage was applied to the upper plate electrode using a Glassman (High Bridge, N.J.) power supply model KL5R600, using higher voltage for initial plasma striking and lower for operation. Alternatively, RF/microwave, hot filament, and parallel plate-style PECVD is used to grow aligned CNT's.

Growth time was thirty minutes, at which point gas flow was stopped, all power supplies were turned off, and the samples were allowed to cool to room temperature in vacuum to avoid potential rapid oxidation if exposed to atmosphere while at growth temperature.

The concentration gradient, tube walls, and internal structure (such as bamboo intersects) is partially determined by the shape and size of the catalyst particle (Ducati, et al., *The role of the catalytic particle in the growth of carbon nanotubes by plasma enhanced chemical vapor deposition*. Journal of Applied Physics, 2004. 95(11): p. 6387-6391). However, other forces known in the art also affect nanotube characteristics. For example, alignment mechanism for PECVD growth are based on electrostatic forces along electric field lines.

As illustrated in FIGS. 5(A) through (D), as nanotube walls 1 grow from catalyst 2, electrostatic force $F_1$ acting along the applied electric field induces tensile stress $F_2$ at the carbon precipitation points on the catalyst particle during growth in both the tip and root growth mechanisms. Any deviation or fluctuation during the process could cause misalignment. In that case, the electrostatic force $F_1$ would induce a compressive stress $F_3$ due to the interaction of the CNT and the electric field. The compressive stress would be a restoration force to cause re-alignment in the tip growth, but not for the root growth due to the opposite distribution of the stress.

Figure 6A:
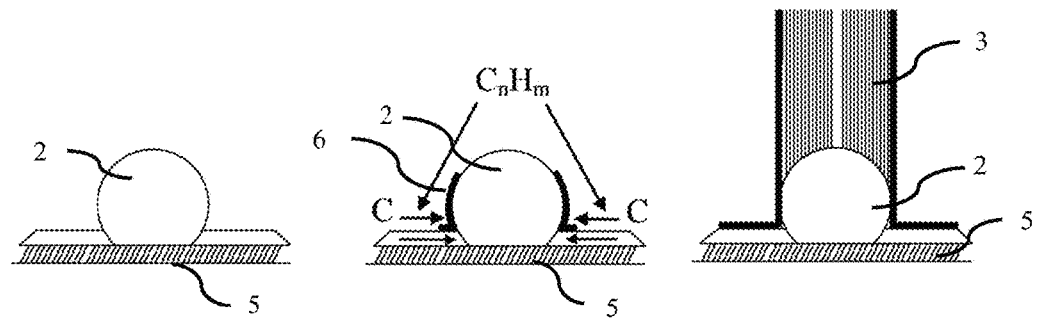
FIG. 6A is an illustration of the growth mechanism for (A) root growth.
Figure 6B:
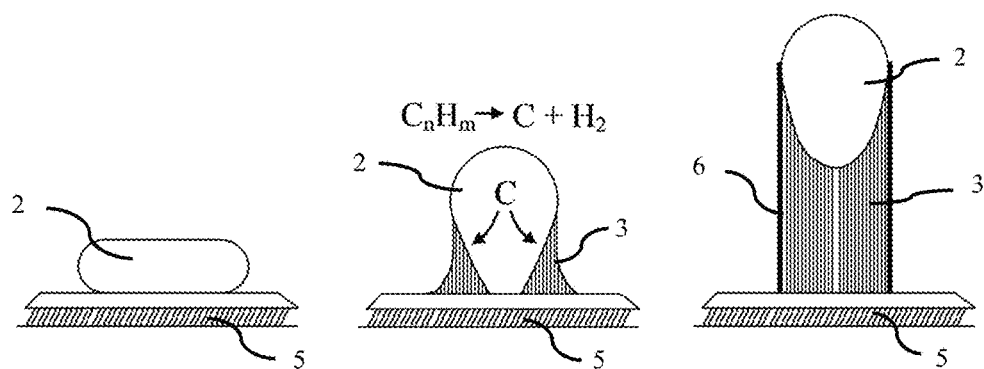
FIG. 6B is an illustration of the growth mechanism for tip growth.

Substrate temperature (Ducati, et al., *Temperature selective growth of carbon nanotubes by chemical vapor deposition*. Journal of Applied Physics, 2002. 92(6): p. 3299-3303), deposition thickness (Chhowalla, et al., *Growth process conditions of vertically aligned carbon nanotubes using plasma enhanced chemical vapor deposition*. Journal of Applied Physics, 2001. 90(10): p. 5308-5317), and exposure to any etching precursor gasses ($NH_3$) can have an effect on the size and shape of catalyst particles formed from a deposited catalyst film. For PE-CVD, the carbon atoms enter the top of catalyst 2 and precipitate out of the bottom as precipitate 6, pushing the catalyst particle upwards from substrate 5 as the carbon nanotube forms (Sinnott, S. B., et al., *Model of carbon nanotube growth through chemical vapor deposition*. Chemical Physics Letters, 1999. 315(1-2): p. 25-30), as seen in FIG. 6(B), producing a carbon nanotubes (CNT) 3 with catalyst particle 2 at the tip; a process known as tip growth. This differs from CVD, where the carbon precipitates as a nanotube from the upper surface of the catalyst, which accounts for the apparent bottom-up growth of the nanotube, known as root growth, as seen in FIG. 6(A).

Figure 7:
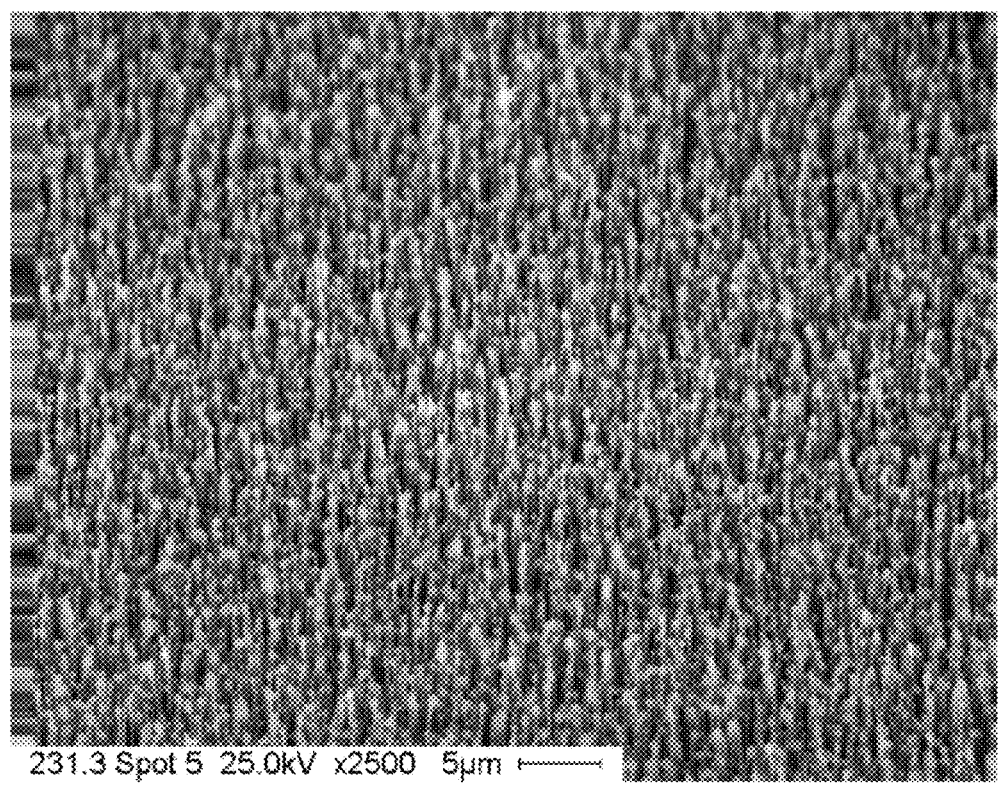
FIG. 7 is a scanning electron microscope (SEM) image of carbon nanotubes grown from 20 nm thick nickel catalyst.

Post-growth morphology analysis of the CNTs was performed using a Hitachi (Hitachi High Technologies America, Pleasanton, Calif.) model S-800 Scanning Electron Microscope. Image capture was accomplished with a Phoenix digitizing system from EDAX (a division of AMETEK Inc, Mahwah, N.J.), as seen in FIG. 7. CNT dimensions were quantified, as summarized in Table 1. Carbon nanotube growth was uniform across the catalyst deposited area and maintained overall dimensions similar to the initial patterned catalyst dimensions.

TABLE 1

Carbon nanotube physical characteristics after growth on MALDI support.

| CNT structure | multiwall |
|---|---|
| average length | 2.5 μm |
| average width | 110 nm |

Example 2

Figure 8:
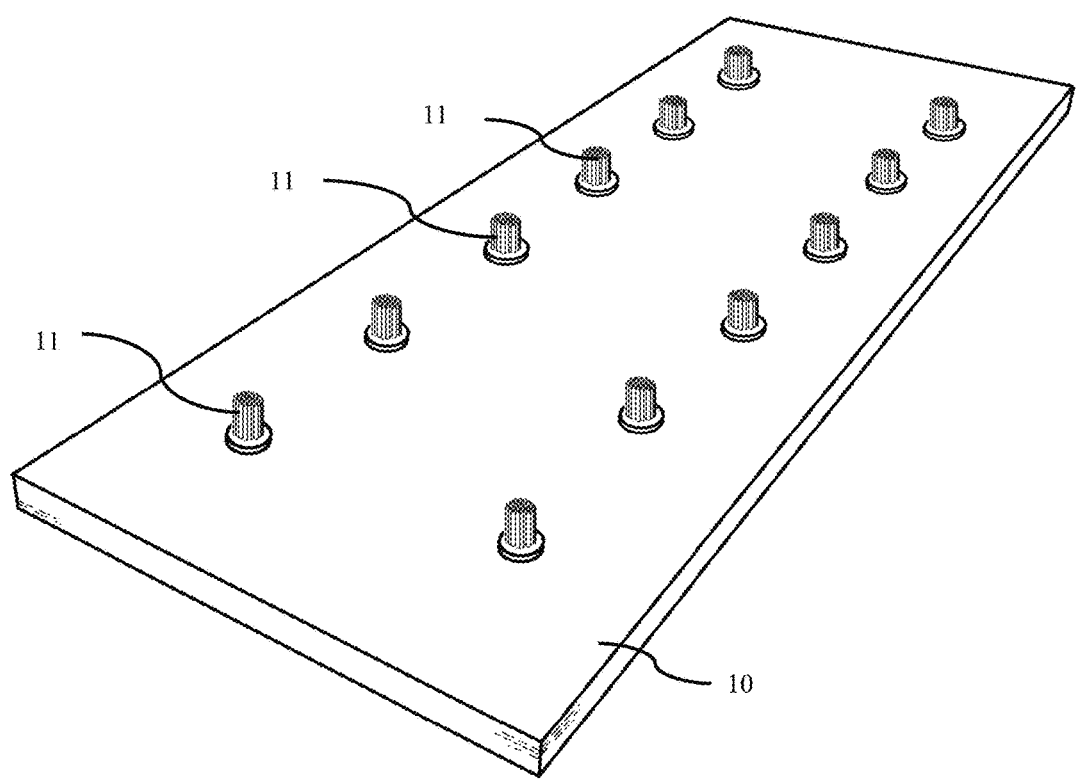
FIG. 8 is an isometric view of the target support wafer of the present invention. The carbon nanotubes have an increased size compared to the wafer to allow visualization of the nanotubes.

A vital element of mass spectrometers, such as MALDI, are target support 10. Anchor spot 11 is developed on target support 10, and is designed to hold or maintain a target 20, seen in FIG. 8. Target support 10 may comprise or be coated with a hydrophobic material, as is known in the art.

Carbon nanotubes are extremely hydrophobic and have the capability of absorbing UV energy. These characteristics of carbon nanotubes enhance MALDI detection and enable matrixless biomolecular detection. The carbon nanotube material creates a surface for improved ionization or production of ion plume, at least in part from the hydrophobic nature of the carbon nanotube surface. After the growth of carbon nanotubes, the anchor spots become slightly roughened and provide large surface areas that promote the crystallization of analyte and matrix. Carbon nanotubes provide not only a hydrophobic anchor, but a large surface area with strong absorption at 334 nm.

Carbon nanotubes grow on a layer of transition metal catalyst pre-deposited on a substrate at optimal temperature and pressure or transition metal catalytic clusters. Carbon nanotubes can also be directly coated on a chemically modified surface. There are a number of techniques for the preparation of carbon nanotubes. For instance, single walled carbon nanotubes have been prepared as discussed by Ericson et al., Chem. Mater. 2003, 15, 175-178, 2003; Huang, Z. P., Applied Physics Letters, Volume 82, Number 3, Jan. 20, 2003; Melosh et al., Science, Volume 300, Apr. 4, 2003; Chen, R. J., J. Am. Chem. Soc. 2001, 123, 3838-3839; Bradley, K, NanoLetters Vol. 0. No. 0 A-D, Nov. 5, 2003;

Lustig, S. R., Nanoletters, Vol. 3, No. 8, 1007-1012, 2003.). Multiple walled carbon nanotubes have also been developed and employed. A number of techniques for preparing these types of nanotubes are also known in the art. Both single wall and multiwall carbon nanotubes can be aligned themselves in a defined direction. Carbon nanotubes largely comprise a ring structure organized in a variety of ways. For instance, they may be ordered at the atomic level as well as to form larger ordered structures and/or supramolecular structures. These various ordered structures are applicable to the present invention and improve over the prior art in providing more efficient ion plume. Other methods and techniques known and developed in the art may be employed.

Chemical vapor deposition (CVD) uses hydrocarbon gases, such as $CH_4$, CO, $C_6H_6$, and $C_2H_5OH$, as a carbon stock with metal catalysts, like Fe, Fe/Mo, Co, Co/Mo, and Ni, as a "seed" to grow carbon nanotubes at 500° C.-1200° C. The distribution, density and location of these seeds determined the resulting carbon nanotube density and location. Seeds can be controlled using polymer carrier approaches, and lithography. In these approaches, a polymer is employed as a binder to disperse a catalyst uniformly across the wafer by a spin coating method. Catalysts can be either attached or otherwise complexed to the repeat unit of one segment of a polymer or one of the homopolymer constituents. The size of catalyst cluster, i.e. seed, after polymer removal is determined by the catalyst-containing chain length. Spacing between seeds is determined by the dilution factor, the volume ratio of polymer segments or by lithography, with distance between seeds determined by electron beam or optical lithography. Through this approach, the population of carbon nanotubes can be controlled precisely and also the carbon nanotube size.

Carbon nanotubes can also be grown using a related dispersion approach. For instance, 0.2 wt % Ni may be spun or sputtered onto a silicon dioxide wafer surface followed by annealing at 200° C. for 24 hrs and removing the organic component. The resulting Ni catalyst is uniformly dispersed and may be defined into seeds. Treatment with a carbon source then results in nanotubes on the surface of the wafer. Other dispersion techniques and materials may be utilized such as 0.25 wt % Polystyrene-b-Poly-(ferrocenyl ethyl methyl silane), coated on a thermal oxide surface. The wafer/catalyst is calcinated at 700° C. and carbon nanotube growth performed at 900° C. under $CH_4$.

Anchor spot 11 is at least one patch of aligned carbon nanotubes, which are grown by plasma enhanced chemical vapor deposition (PECVD) on target support 10, which may be a standard silicon wafer or other conductive substrates could be used, such as metal foils. Nickel catalyst 12 was patterned onto target support 10 at pre-determined locations of the target support. However, other catalysts include Fe and Co. The catalyst comprises a thin layer of the nickel metal catalyst sputtered onto target support using mask-based patterning or electron beam lithography and metal evaporation, resulting in a 10-25 nm layer of nickel at spot locations 12 that are 150 µm in diameter, seen in FIG. 9. The target support was then subjected to plasma-enhanced chemical vapor deposition (PECVD). The target support was placed in a vacuum container and the ambient pressure reduced to below $1 \times 10^{-3}$ Torr. Then the substrate was heated to approximately 600° C. Ammonia was added to the vacuum container at 200 standard cubic centimeters per minute (sccm). After approximately 30 seconds, acetylene gas was added at 50 sccm forming a mixture of 1:4 acetylene to ammonia. The reaction was allowed to commence for 30 minutes, forming a patterning of areas with and without nanotube growth. The carbon nanotubes are uniformly distributed in the seeded surface of the wafer. The carbon nanotubes also display predictable density and ordering, as seen in the images.

Anchor spot 11 is defined as an area coated with nanotubes, which acts as an anchoring surface for analyte/water-insoluble matrix solutions. This anchors a deposited test drop to the nanotube area, since the nanotube spot is surrounded by hydrophobic native Si oxide. In traditional MALDI samples, the test drop leaves sequential rings, formed from distinct crystallization events during evaporation of the test drop. The carbon nanotube anchor spots also advantageously provide nucleation centers causing early nucleation of the analyte/matrix compound on top of the nanotube array as the droplet evaporates. This early nucleation prevents supersaturation of the solution and reduces deposition on areas surrounding the nanotube spots.

Example 3

Matrix α-cyano-4-hydroxycinnamic acid (αCHCA; Sigma-Aldrich, St. Louis, Mo.), high-purity acetonitrile (Burdick and Jackson, Morristown, N.J.), and peptide standard mix (Mariner CALMIX 4700; Applied Biosystems, Foster City, Calif.—hereinafter Peptide Mixture 1) consisting of des-Arginine1-Bradykinin (m/z 904), Angiotensin I (m/z 1297), Glu1-Fibrinopeptide B (m/z1569), and Adrenocorticotropic Hormone (ACTH) (1-17 clip) (m/z 2092)) were obtained. Information on the peptides is shown in Table 2. Water used was obtained from a Milli-Q water purification system (Millipore, Milford, Mass.) with a resistivity of $1.8 \times 10^8$ ohm per centimeter (MegΩ-cm) indicating highly purified water. Cleaning solvents such as acetone, isopropyl alcohol, and methanol were purchased from J.T. Baker (a division of Mallinckrodt Chemicals, Phillipsburg, N.J.).

TABLE 2

Amino acid sequences for each respective peptide contained in Peptide Mixture 1. The amino acids in bold indicate the presence of a carbon ring.

| | Analyte Component | Sequence |
|---|---|---|
| SEQ ID No. 1 | des-Arginine1-Bradykinin | H-Pro-Pro-Gly-Phe-Ser-Pro-Phe-Arg-OH |
| SEQ ID No. 2 | Angiotensin I | H-Asp-Arg-Val-Tyr-Ile-His-Pro-Phe-His-Leu-OH |
| SEQ ID No. 3 | Glu1-Fibrino-peptide B | H-Glu-Gly-Val-Asn-Asp-Asn-Glu-Glu-Gly-Phe-Phe-Ser-Ala-Arg-OH |
| SEQ ID No. 4 | Adrenocorticotropic hormone (ACTH) | H-Ser-Tyr-Ser-Met-Glu-His-Phe-Arg-Trp-Gly-Lys-Pro-Val-Gly-Lys-Lys-Arg-OH |

For initial experiments, a solution of 1:1 volumetric ratio of acetonitrile to de-ionized water was prepared as a matrix solvent. Dry crystalline matrix αCHCA was weighed out with a Sartorius Research (Goettingen, Germany) model R200D digital precision balance and combined in a 1.5 mL Eppendorf® tube (Westbury, N.Y.) to a final concentration of 3 mg/mL and mixed for two minutes with a Vortex-Genie mixer (Scientific Industries, Bohemia, N.Y.). The analyte peptide mixture 1 was measured and combined in a new 1.5 mL Eppendorf® tube with de-ionized water according to the instructions from Applied Biosystems to achieve a final concentration of 250 fmol/µL and mixed for two minutes. In a separate 0.5 mL Eppendorf® tube, 0.2 mL of each of the analyte and matrix solutions were added and mixed for two minutes to ensure complete homogenization for concurrent deposition.

A standard 100-well, stainless steel MALDI plate (Applied Biosystems, part number V700666) was cleaned with methanol and de-ionized water before use and dried with a stream of nitrogen. Carbon nanotube samples were not cleaned after growth or SEM investigation, but were stored in closed Gel-Pak® boxes (Hayward, Calif.) at all times to prevent contamination or physical damage to the nanotubes. The combined matrix/analyte solution was deposited onto the MALDI plate and carbon nanotube spots using an Eppendorf® Research® model precision pipette (0.1 µL-2.5 µL range) with a volume of 0.2 µL.

Deposition was performed under an Olympus SZ61 Stereoscope (Melville, N.Y.) with DP70 digital camera to capture time-lapse images of the drying process. Sample lighting provided by a Dolan-Jenner MI-150 fiber optic illuminator (Edmund Optics, Barrington, N.J.) set for fifty percent of maximum intensity (light source is a 150 watt quartz halogen bulb with 3200K color temperature). The samples were dried by exposure to room air at an ambient temperature of 23° C. MALDI investigation of the samples was performed immediately after preparation to minimize any potential effects due to age, temperature, atmospheric moisture, oxidation, light, and environmental contaminants.

Additional dilution stages were required to achieve the desired concentrations. Matrix and analyte solutions were diluted separately to ensure proper distribution and only combined immediately before use. Every effort was made to deposit all of the samples in a particular experiment in a uniform fashion with identical conditions and on the same day and time. Only pipette tips were changed between samples to prevent contamination of the samples and results. Solutions used for sample preparation were prepared fresh the day of the experiment.

The MALDI mass spectrometric experiments were performed using an Applied Biosystems Voyager DE STR MALDI-TOF in positive-ion reflector mode with a 200 nano-second delayed extraction and 25 kV accelerating voltage. Ionization was achieved using a 355 nm wavelength laser with 20 Hz firing frequency. Laser intensity was adjusted to slightly above the threshold level for each sample to maintain mass resolution and minimize noise. Data was collected for 250 consecutive laser shots per spectrum.

In order to calculate the signal to noise ratios, the signal value from each independent peak was divided by the root mean square (RMS) noise from the individual spectra that was calculated using the Data Explorer software. This provided a means of normalization for the spectra and allowed easier comparison and manipulation of the data. No data smoothing routines were applied. Microsoft Excel and Wavemetrics Igor Pro 4.0 software was used for statistical calculation and graphing.

Standard and CNT-Enhanced Substrates

In order to compare of drying behavior of αCHCA matrix on the standard stainless steel MALDI plate and on a carbon nanotube-enhanced substrate, samples were prepared by depositing 0.2 µL of a matrix/analyte solution. A solution of 1:1 volumetric ratio of acetonitrile to de-ionized water was prepared as a matrix solvent. Dry crystalline matrix αCHCA was weighed out with a Sartorius Research (Goettingen, Germany) model R200D digital precision balance and combined in a 1.5 mL Eppendorf® Safe-Lock Microcentrifuge tube (Westbury, N.Y.) with sufficient quantity of solution to achieve a final concentration of 3 mg/mL and mixed for two minutes with a Vortex-Genie mixer (Scientific Industries, Bohemia, N.Y.). The analyte peptide mixture 1 was measured and combined in a new 1.5 mL Eppendorf® tube with de-ionized water according to the instructions from Applied Biosystems to achieve a final concentration of 250 fmol/µL and mixed for two minutes. In a separate 0.5 mL Eppendorf® tube, 0.2 mL of each of the analyte and matrix solutions were added and mixed for two minutes to ensure complete homogenization. A standard 100-well, stainless steel MALDI plate (Applied Biosystems, part number V700666) was cleaned with methanol and de-ionized water before use and dried with a stream of nitrogen. Carbon nanotube samples were not cleaned after growth or SEM investigation, but were stored in closed Gel-Pak® boxes (Hayward, Calif.) at all times to prevent contamination or physical damage to the nanotubes. The combined matrix/analyte solution was deposited onto the MALDI plate and carbon nanotube spots using an Eppendorf® Research® model precision pipette (0.1 µL-2.5 µL range) with a volume of 0.2 µL.

The samples were dried by exposure to room air at an ambient temperature of 23° C. Time-lapse optical microscopy images (Olympus SZ61 stereo microscope) of the drying process for the samples was obtained (data not shown). For the stainless steel MALDI plate, the droplet flattened as the contact angle at the liquid/solid interface changed, indicating a hydrophilic state (contact angle less than 90 degrees). Crystallization occurred at the edge of the droplet as a result of increased concentration gradients around the perimeter of the droplet (referred to as the "contact line"), which is the result of maximum evaporation flux at the edge of the droplet (Smalyukh, et al., *Structure and dynamics of liquid crystalline pattern formation in drying droplets of DNA*. Physical Review Letters, 2006. 96(17)) creating a Marangoni loop (Bhardwaj, et al., *Pattern formation during the evaporation of a colloidal nanoliter drop: a numerical and experimental study*. New Journal of Physics, 2009. 11) which transported solute from the droplet interior to the contact line. The increase in concentration led to the formation of matrix/analyte crystals at the contact line. The crystals formed micromenisci (Dufresne, E. R., et al., *Flow and fracture in drying nanoparticle suspensions*. Physical Review Letters, 2003. 91(22)) at the droplet contact line effectively "pinning" the line (Deegan, R. D., et al., *Capillary flow as the cause of ring stains from dried liquid drops*. Nature, 1997. 389(6653): p. 827-829), which prevented the normal receding mechanism. As the droplet volume continued to decrease, surface tension was sufficient to overcome capillary forces (known as "de-pinning"; Bhardwaj, et al., *Pattern formation during the evaporation of a colloidal nanoliter drop: a numerical and experimental study*. New Journal of Physics, 2009. 11), at which point the liquid retreated sequentially, and deposited additional crystals at the previous edges of the liquid due to the same mechanism. The drying results in deposition of off-center, concentric rings of crystal deposits, leaving very few crystals in the field area between the rings.

The drying process on the CNT-enhanced substrate showed a reduction in droplet diameter during the evaporation process which corresponded to the decrease in droplet volume. The droplet appeared to maintain a rounded shape and did not flatten onto the silicon surface, which indicated a hydrophobic condition (contact angle greater than 90 degrees). The initial deposition was not centered on the area occupied by the carbon nanotubes but centered on the CNT area during drying. Additionally, crystallization did not occur in rings around the contact perimeter as on the MALDI plate, but rather on the carbon nanotubes. During final evaporation, the small volume of liquid that was present during the final stages of the deposition process preferentially resided on the carbon nanotubes until the solvent evaporated completely. The silicon wafer substrate used for the carbon nanotube enhanced samples was manufactured from a single crystal of silicon and was polished to a high degree (nearly atomically flat). As a result, the silicon wafer reflected light in a more ideal manner.

Adobe Photoshop CS3 Extended software was used to perform an image segmentation technique (Sedgewick, *Scientific Imaging with Photoshop: Methods, Measurement, and Output*. 2008, Berkeley, Calif.: New Riders Press. 312) using a color difference filter to separate the matrix crystals from the background to enhance contrast. Image J software (National Institute of Health) was used to measure the area of crystallization for the two samples. The standard sample covers an area of 0.651 mm$^2$ (1.104 mm diameter) while the CNT-enhanced sample is only 0.021 mm$^2$, with a diameter of 206 micrometers, which is on the same order as the diameter of the MALDI laser at the point of investigation.

Figure 10A:
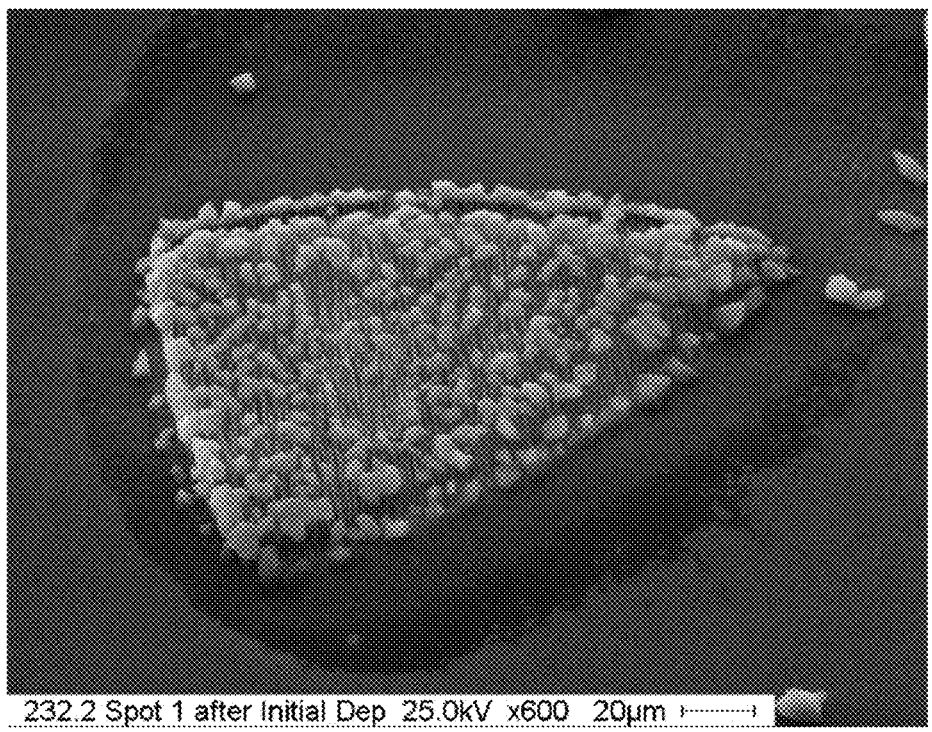
FIG. 10A is a scanning electron microscope (SEM) images of the αCHCA matrix crystals deposited on the carbon nanotubes.
Figure 10B:
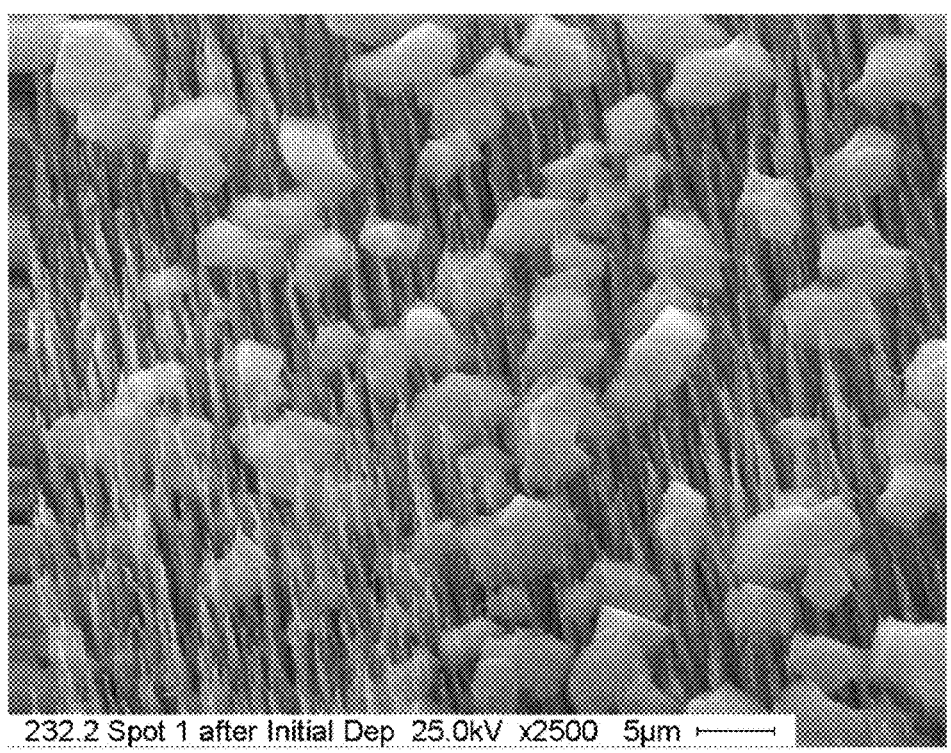
FIG. 10B is a scanning electron microscope (SEM) images of the αCHCA matrix crystals deposited on the carbon nanotubes in a magnified view.

Scanning electron microscopy images (Hitachi S-800) of the sample deposited on the CNT-enhanced substrate can be seen in FIGS. 10(A) and (B). The standard MALDI plate was too large to fit into the loading door of the SEM, so no images were taken of that sample. The carbon nanotube enhanced sample was imaged after the initial deposition, before being exposed to vacuum conditions or laser irradiation in the MALDI instrument. The crystals (cubic structures) that formed on the carbon nanotubes (long, thin structures) display a high degree of homogeneity both in size and dispersion. The surrounding area in the image is the silicon substrate.

Figure 11A:
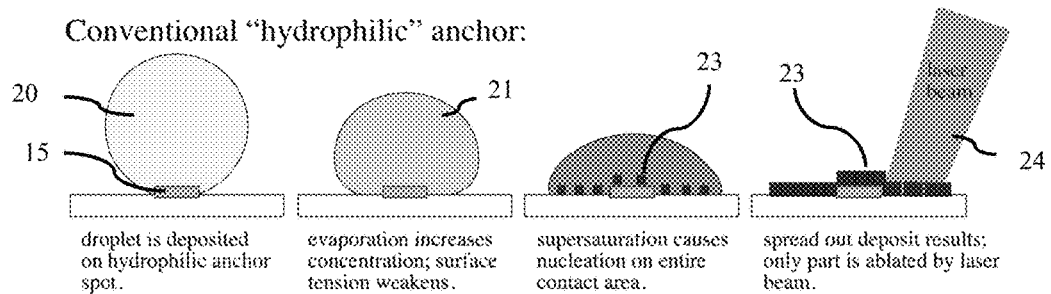
FIG. 11A is a schematic depictions of crystallization processes on a standard hydrophilic anchor. The nucleation promoting anchor keeps the analyte/matrix concentration of the droplet nearly constant during evaporation of the solvent through early nucleation on the anchor spot. This prevents deposition of solids in areas outside the anchor spot.
Figure 11B:
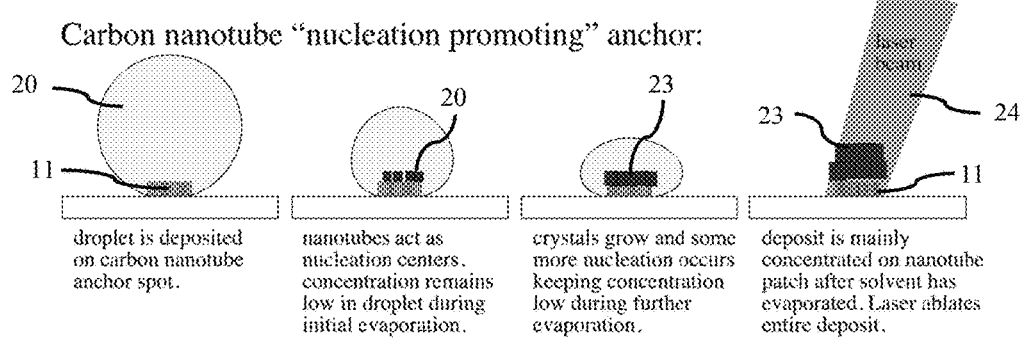
FIG. 11B is a schematic depictions of crystallization processes on nucleation promoting anchor spot. The nucleation promoting anchor keeps the analyte/matrix concentration of the droplet nearly constant during evaporation of the solvent through early nucleation on the anchor spot. This prevents deposition of solids in areas outside the anchor spot.
Figure 12A:
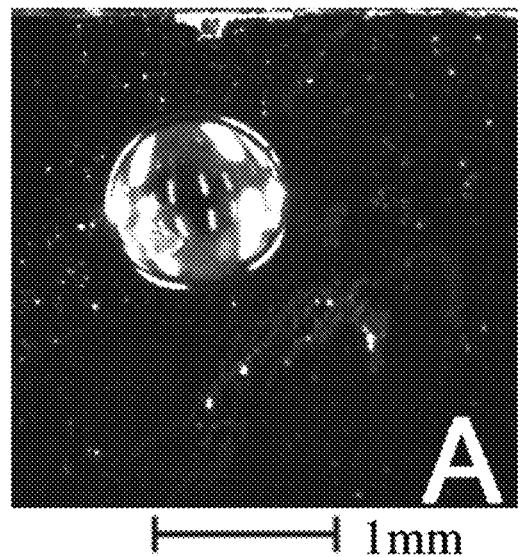
FIG. 12A is a time lapse image of 0.2 µL αCHCA matrix/analyte solution deposited on a silicon wafer with a patterned area of carbon nanotubes grown by PECVD. Drying time and temperature was unchanged from the deposition on the MALDI plate.
Figure 12B:
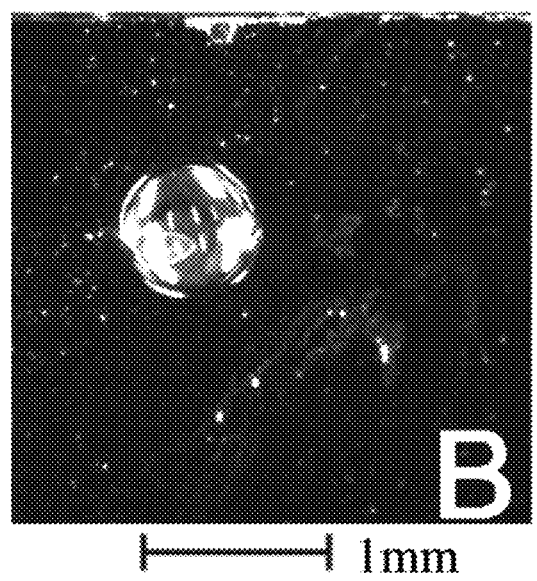
FIG. 12B is a time lapse image of 0.2 µL αCHCA matrix/analyte solution deposited on a silicon wafer with a patterned area of carbon nanotubes grown by PECVD. Drying time and temperature was unchanged from the deposition on the MALDI plate.
Figure 12C:
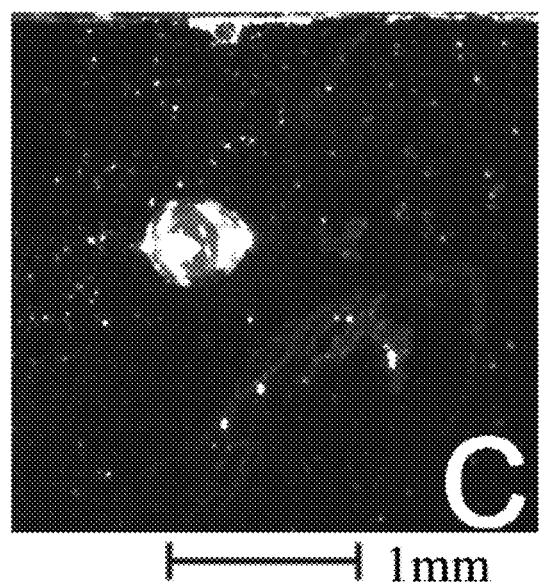
FIG. 12C is a time lapse image of 0.2 µL αCHCA matrix/analyte solution deposited on a silicon wafer with a patterned area of carbon nanotubes grown by PECVD. Drying time and temperature was unchanged from the deposition on the MALDI plate.
Figure 12D:
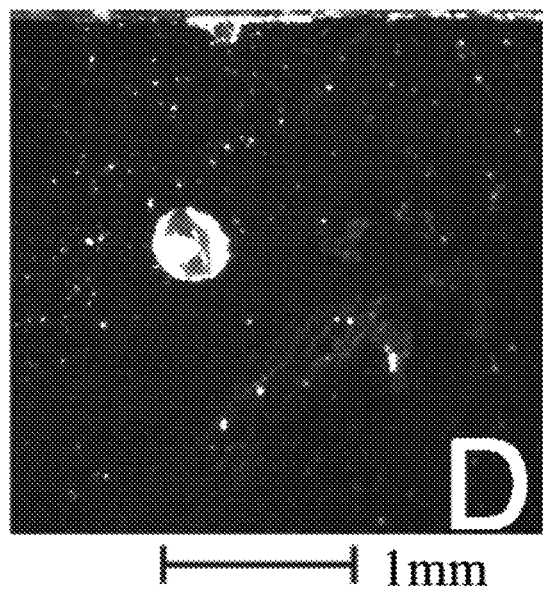
FIG. 12D is a time lapse image of 0.2 µL αCHCA matrix/analyte solution deposited on a silicon wafer with a patterned area of carbon nanotubes grown by PECVD. Drying time and temperature was unchanged from the deposition on the MALDI plate.
Figure 12E:
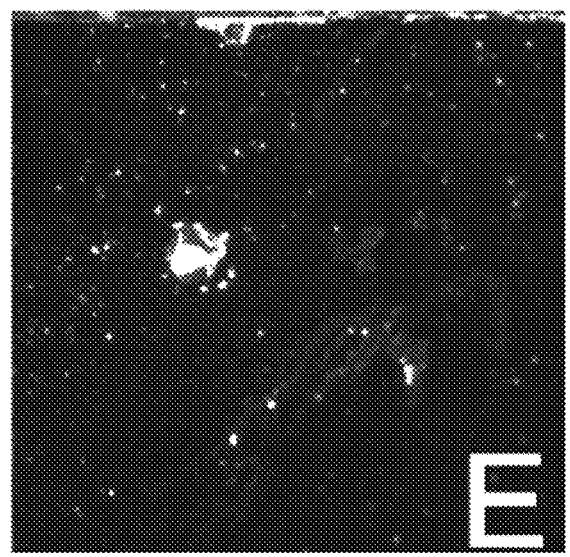
FIG. 12E is a time lapse image of 0.2 µL αCHCA matrix/analyte solution deposited on a silicon wafer with a patterned area of carbon nanotubes grown by PECVD. Drying time and temperature was unchanged from the deposition on the MALDI plate.
Figure 12F:
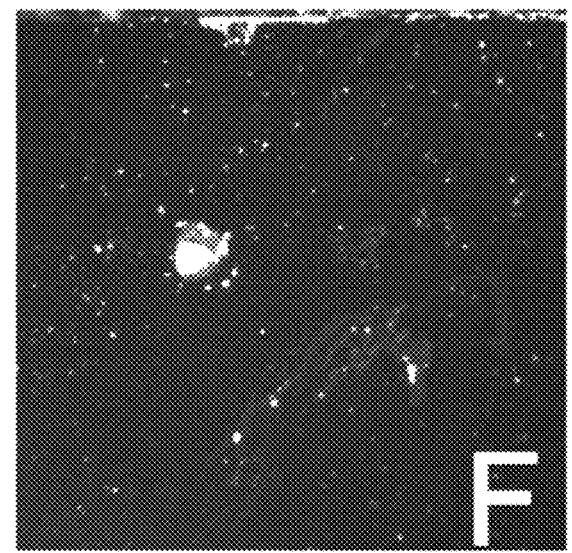
FIG. 12F is a time lapse image of 0.2 µL αCHCA matrix/analyte solution deposited on a silicon wafer with a patterned area of carbon nanotubes grown by PECVD. Drying time and temperature was unchanged from the deposition on the MALDI plate.

For comparison, an AnchorChip™ (Bruker Daltonics) plate was used to concentrate samples, using a patterned area of hydrophilic spots as anchors on a surrounding hydrophobic surface. A schematic illustrating the evaporation process on the hydrophilic anchor, seen in FIG. 11(A), versus CNT-enhanced anchor is shown in FIG. 11(B). For a conventional hydrophilic-type of anchor plate, the droplet of matrix 20 containing solution is deposited on anchor spot 15, and the solvent evaporates from the solution, concentrating the solute 21. Continued evaporation causes super-saturation of the solution, which triggers nucleation at the contact edge of the droplet forming nucleation precipitate 23, resulting in a crystal field with a large diameter relative to the MALDI laser diameter 24 at the sample surface, in which only a few crystals are investigated concurrently.

While hydrophilic anchors come in a variety of sizes, the manufacturer recommends that matrix αCHCA (non-aqueous) be used with the 600 µm diameter anchor spots. Anchor spots with diameters as low as 200 µm are available for aqueous-based matricies, however the product literature states that size anchor is not able to reliably attract droplets of micro-liter volume.

Droplet deposition of the identical matrix solution onto the carbon nanotube enhanced substrate using CNT anchor spot 11 is the same as a standard MALDI plate. During initial solvent evaporation, the solute concentration remains stable as the matrix initiates crystallization on the carbon nanotubes 11. The matrix crystals 23 precipitate and remove solute from the evaporating droplet, preventing crystal formation on the surrounding area. In the resulting deposit, the majority of the crystals are grown on the carbon nanotubes. The MALDI laser 24 is able to simultaneously interrogate a greater percentage of the deposited matrix/analyte crystals, which can produce an increase in collected signal strength.

The carbon nanotube enhanced anchor demonstrated the ability to concentrate solutions of matrix αCHCA to final dried droplet diameters below 200 µm, as seen in FIGS. 12(A) through (D).

Figure 13A:
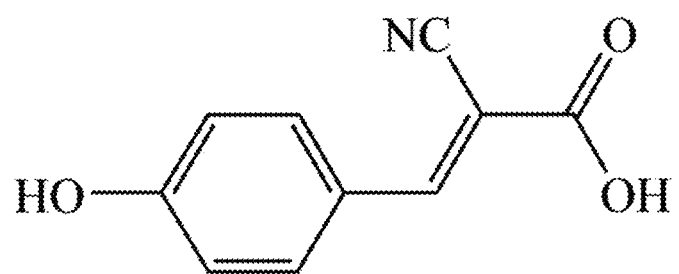
FIG. 13A is a schematic of αCHCA molecule.
Figure 13B:
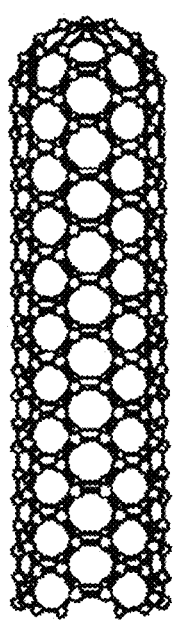
FIG. 13B is a schematic of a carbon nanotube to illustrate hexagonal carbon structure.

The cause of early nucleation of matrix crystals on the carbon nanotubes appears to be the result of interaction between the hexagonal carbon ring in the matrix molecule αCHCA and the carbon atoms on the surface of the nanotube, also in a hexagonal arrangement, as seen in FIGS. 13(A) and (B). The results of π-bond stacking between aromatic compounds and carbon nanotubes has been published by research groups studying interactions between pyrenyl groups and CNT (Chen, et al., Noncovalent sidewall functionalization of single-walled carbon nanotubes for protein immobilization. Journal of the American Chemical Society, 2001. 123(16): p. 3838-3839), benzyl groups and CNT (Star, et al., *Preparation and properties of polymer-wrapped single-walled carbon nanotubes*. Angewandte Chemie-International Edition, 2001. 40(9): p. 1721-1725), DNA and CNT (Zheng, et al., *DNA-assisted dispersion and separation of carbon nanotubes*. Nature Materials, 2003. 2(5): p. 338-342), and aromatic peptides and CNT (Zorbas, et al., *Importance of aromatic content for peptide/single-walled carbon nanotube interactions*. Journal of the American Chemical Society, 2005. 127(35): p. 12323-12328; Piao, et al., *Adsorption of L-phenylalanine on single-walled carbon nanotubes*. Journal of Physical Chemistry C, 2008. 112(8): p. 2857-2863; Salzmann, et al., Interaction of tyrosine-, tryptophan-, and lysine-containing polypeptides with single-wall carbon nanotubes and its relevance for the rational design of dispersing agents. Journal of Physical Chemistry C, 2007. 111(50): p. 18520-18524; Tomasio & Walsh, *Atomistic modelling of the interaction between peptides and carbon nanotubes*. Molecular Physics, 2007. 105 (2-3): p. 221-229; Zheng, et al., *Nanotube-Peptide Interactions on a Silicon Chip*. Journal of Physical Chemistry C, 2009. 113(10): p. 3978-3985).

The π-bond is thought to be a contributing force in aromatic compound adsorption on carbon nanotubes. Hydrogen and covalent bonds may also be present between molecular components (OH groups) and CNT surfaces (Piao, et al., *Adsorption of L-phenylalanine on single-walled carbon nanotubes*. Journal of Physical Chemistry C, 2008. 112(8): p. 2857-2863). The adsorption of αCHCA onto the nanotube surface may initiate the crystallization of matrix out of solution and account for the phenomena observed during the droplet drying process and the inter-nanotube crystal formation in FIGS. 10(A) and (B). The rapid rate of crystallization on the carbon nanotubes is likely the result of Marangoni convection which would supply additional matrix molecules to the localized area around the CNT's as the crystallization process removes matrix from the solution. In addition, the carbon nanotubes large surface area provides substantial capacity for adsorption and crystallization.

Further experiments were performed to document and validate the mechanism for interaction between the matrix molecules and the carbon nanotubes. The first experiment was designed to verify that the CNT's were responsible for the lateral concentration and early nucleation by deposition of the αCHCA matrix solution on both a bare silicon wafer and a wafer that had a patterned area of nickel (catalyst for CNT growth via PECVD) that was created by e-beam deposition as described in Example 1.

The deposited droplet consisted of the same solution and volume as those used in the previous examples. The drying process on the bare silicon substrate was similar to that observed on the bare, stainless steel MALDI plate, i.e. matrix crystals formed on the surface primarily at the contact edge between the substrate and the droplet. The final deposit was larger than the equivalent on the MALDI plate with an area of 0.759 mm$^2$ and a maximum diameter of 1.057 mm. The deposition on the substrate with a patterned nickel area demonstrated similar drying patterns to both the bare silicon substrate and the stainless steel MALDI plate, with crystallization occurring in rings during evaporation. While evaporation was in the direction of the nickel pattern, no crystallization occurred directly on the nickel. The final dried droplet was slightly smaller than that on the MALDI plate, with an area of 0.626 mm$^2$ with a 0.855 mm diameter.

The results of these experiments indicate that for αCHCA, the enhanced nucleation behavior was due to matrix interaction with the carbon nanotubes and not attributed to the presence of nickel or the surrounding silicon substrate.

Figure 14A:
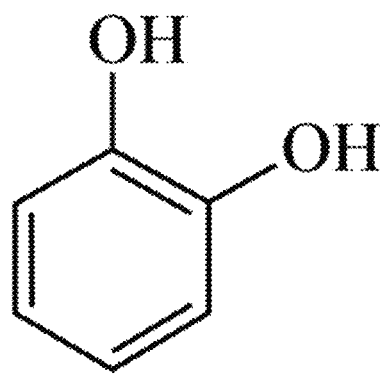
FIG. 14A is a schematic diagram of Catechol.
Figure 14B:
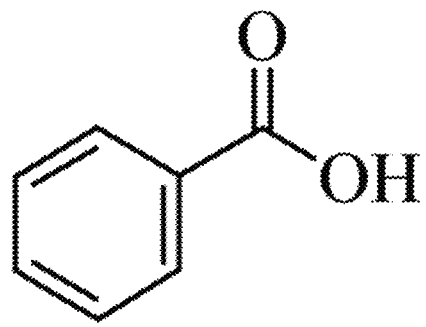
FIG. 14B is a schematic diagram of Benzoic acid.
Figure 14C:
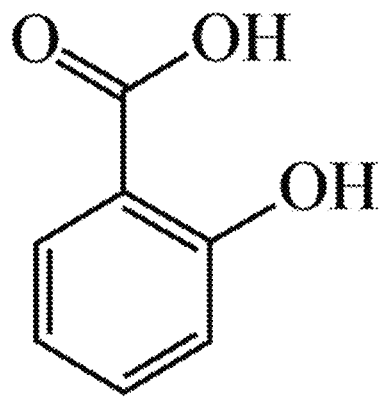
FIG. 14C is a schematic diagram of Salicylic acid.
Figure 15:
FIG. 15 is a schematic diagram of 1,10-Decanediol.

The CNT/matrix interaction was further explored using the crystallization behavior of aromatic molecules with attached hydroxyl and carboxyl groups, shown in FIG. 14(A) through (C), to determine if these groups interacted with the carbon nanotubes. Samples were prepared using molecules that had only hydroxyl components (Catechol), only carboxyl components (Benzoic acid), and both components (Salicylic acid). To test the interaction of hydroxyl terminated, non-aromatic molecules with carbon nanotubes, samples were also prepared using 1,10-Decanediol, shown in FIG. 15.

Individual solutions were made from each of the components with a solvent of 1:1 volumetric ratio acetonitrile to de-ionized water. The solute concentrations were adjusted using the values in Table 3 to keep the molarity of each solution consistent with that of the initial αCHCA solution. Deposition was performed on both the standard MALDI plate and CNT-enhanced substrates as described in previous examples.

TABLE 3

Calculations for concentrations used to prepare solutions with equivalent molarity.

| Solute | Moles | Molecular Mass | Concentration | pH |
|---|---|---|---|---|
| αCHCA | 1.32 × 10$^{-6}$ mol | 189.17 g/mol | 0.25 mg/mL | 2.75 |
| Catechol | 1.32 × 10$^{-6}$ mol | 110.1 g/mol | 0.146 mg/mL | 4.5 |
| Benzoic acid | 1.32 × 10$^{-6}$ mol | 122.12 g/mol | 0.161 mg/mL | 3.6 |
| Salicylic acid | 1.32 × 10$^{-6}$ mol | 138.12 g/mol | 0.183 mg/mL | 2.8 |
| Decanediol | 1.32 × 10$^{-6}$ mol | 174.28 g/mol | 0.23 mg/mL | 7.6 |

The deposition on the MALDI plate resulted in ring structures for all aromatic solutions. The catechol sample had a thin solid ring with very few crystals in the interior. The sample made with benzoic acid resulted in a smaller, dense ring with a large number of central crystals. The salicylic acid resulted in a deposit with similar morphology to an αCHCA deposit, as crystallites formed at the edge of the contact line as the solvent evaporated. The decanediol sample produced thin, straight crystals that did not form a ring structure at the contact edge of the droplet.

For the CNT anchored plate, the drying behavior of the catechol solution and αCHCA showed crystallization did not occur on any area surrounding the CNT. At the final stages, the carbon nanotubes became coated with catechol or αCHCA crystals and a few excess crystals formed on the silicon surface. The evaporation of the salicylic acid solution progressed in a similar fashion to catechol, as the droplet maintained a round shape and symmetrically reduced in diameter. Crystals formed in the center of the CNT area and progressed outward, slightly exceeding the diameter of the patterned region. The benzoic acid droplet dried differently than both αCHCA and catechol; the solution deformed during drying and became elliptical, concentrating directly onto the CNT area. The final crystallization occurred in a ring around the perimeter of the nanotubes, then spread inwards forming long, thin crystals that encrusted the deposition area. This behavior was similar to the drying pattern observed when matrix 3-hydroxy picolinic acid (HPA) was deposited on the carbon nanotube-enhanced substrate.

The sample prepared using decanediol crystallized during solvent evaporation, starting with the contact edge of the droplet and formed straight, thin crystals that developed equally across the sample surface, with no apparent interaction with the carbon nanotubes. These crystals appeared as a "herring-bone" type structure perpendicular to the longest axis of the molecule due to hydrogen bonding of the terminal hydroxyl groups.

Image J software was used to measure the area and diameter of each of the deposited spots. For direct comparison, the data (averaged with standard deviation values) is presented in Table 4 and grouped by solute molecule and substrate type. As a reference, the typical carbon nanotube pattern has an area of approximately 0.02 mm$^2$ and a maximum diameter of 0.2 mm. Of the molecules used in the experiment, salicylic acid was the best analog to αCHCA. The dried droplet areas on both the MALDI plate and the patterned carbon nanotubes were comparable. Additionally, the molecular structures are similar with an aromatic carbon ring with attached hydroxyl and carboxyl groups, and equivalent pH values in solution (2.75 average for αCHCA to 2.8 average for salicylic acid).

TABLE 4

Metrics of dried droplet samples organized by substrate.

| Solute | Substrate | Av. Area (mm$^2$) with std. dev. (σ) | Av. Diameter (mm) with std. dev. (σ) |
|---|---|---|---|
| αCHCA | MALDI plate | 0.591 (0.084 σ) | 1.007 (0.137 σ) |
| αCHCA | Bare Silicon | 0.669 (0.126 σ) | 0.991 (0.093 σ) |
| αCHCA | Patterned Ni | 0.960 (0.473 σ) | 1.105 (0.354 σ) |
| Catechol | MALDI plate | 0.278 (0.123 σ) | 0.630 (0.105 σ) |
| Benzoic acid | MALDI plate | 0.154 (0.042 σ) | 0.459 (0.060 σ) |
| Salicylic acid | MALDI plate | 0.577 (0.161 σ) | 0.948 (0.179 σ) |
| Decanediol | MALDI plate | 0.592 (0.138 σ) | 0.918 (0.129 σ) |
| αCHCA | Patterned CNT | 0.034 (0.018 σ) | 0.263 (0.080 σ) |
| Catechol | Patterned CNT | 0.064 (0.013 σ) | 0.328 (0.041 σ) |
| Benzoic acid | Patterned CNT | 0.066 (0.008 σ) | 0.331 (0.020 σ) |
| Salicylic acid | Patterned CNT | 0.046 (0.007 σ) | 0.267 (0.002 σ) |
| Decanediol | Patterned CNT | 0.287 (0.128 σ) | 0.690 (0.153 σ) |

The results showed the CNT anchor plate significantly reduced the deposition area of deposited sample, as seen in Table 5.

TABLE 5

Reduction in sample area as a result of deposition on CNT substrate compared to standard MALDI plate.

| Solute | Average Area Reduction for Deposition on CNT Substrate |
|---|---|
| αCHCA | 94.25% |
| Catechol | 76.98% |

TABLE 5-continued

Reduction in sample area as a result of deposition
on CNT substrate compared to standard MALDI plate.

| Solute | Average Area Reduction for Deposition on CNT Substrate |
|---|---|
| Benzoic acid | 57.14% |
| Salicylic acid | 92.03% |
| Decanediol | 51.52% |

The mechanism that contributes to the enhanced nucleation on the CNTs was thought to be π-bond stacking between aromatic compounds and the outer surface of carbon nanotubes. The results show that the presence of hydroxyl or carboxyl groups on the solute molecule can affect the crystallization behavior resulting in a marked difference in crystal morphology, an indication that the mechanism is more complex. Additionally, π-bonds are relatively short range resulting in a low probability for primary molecular attraction.

Figure 16:
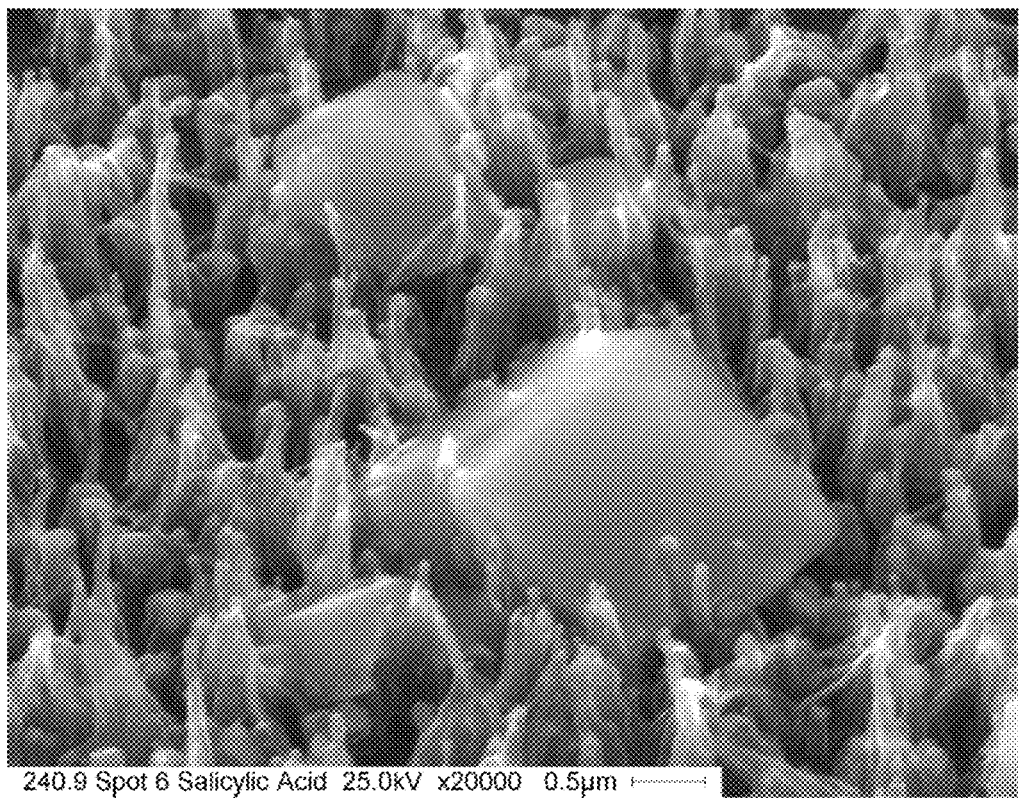
FIG. 16 is a scanning electron microscope (SEM) image of Salicylic acid deposited on CNT's demonstrating crystallization around the carbon nanotubes. The nickel catalyst-containing nanotube tips are seen protruding from the crystal, indicating preferential intersection with the CNT sidewall.
Figure 17A:
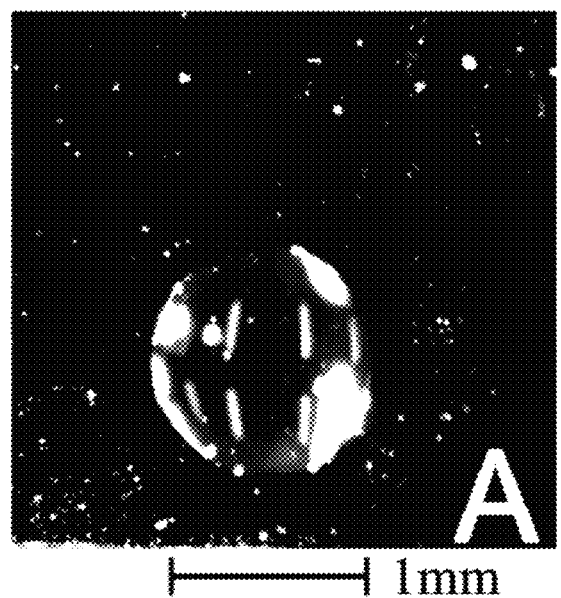
FIG. 17A is a time lapse image of 0.2 µL αCHCA matrix solution deposited on a bare silicon wafer without nickel catalyst or CNT.
Figure 17B:
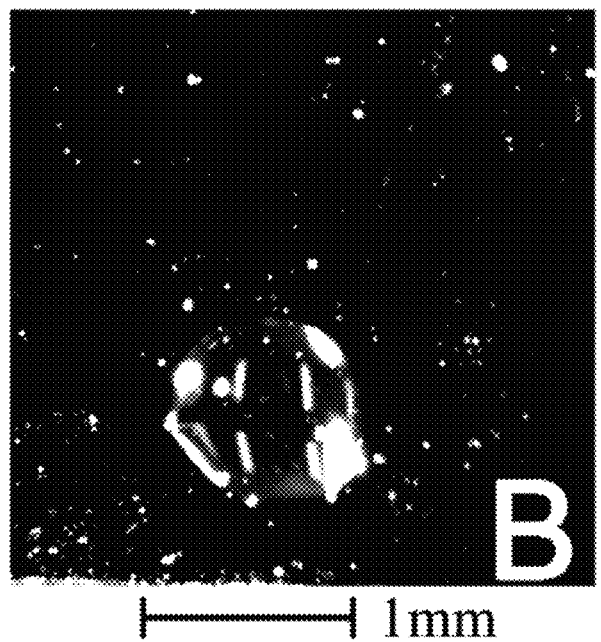
FIG. 17B is a time lapse image of 0.2 µL αCHCA matrix solution deposited on a bare silicon wafer without nickel catalyst or CNT.
Figure 17C:
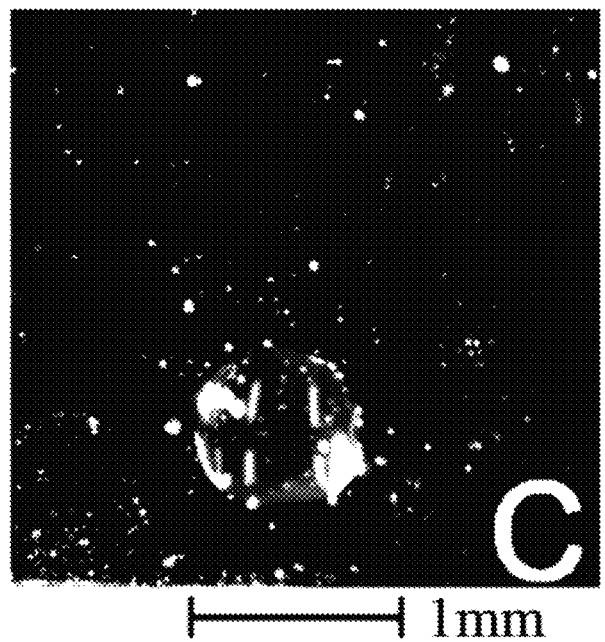
FIG. 17C is a time lapse image of 0.2 µL αCHCA matrix solution deposited on a bare silicon wafer without nickel catalyst or CNT. Crystal ring formation and subsequent pinning visible in the frame.
Figure 17D:
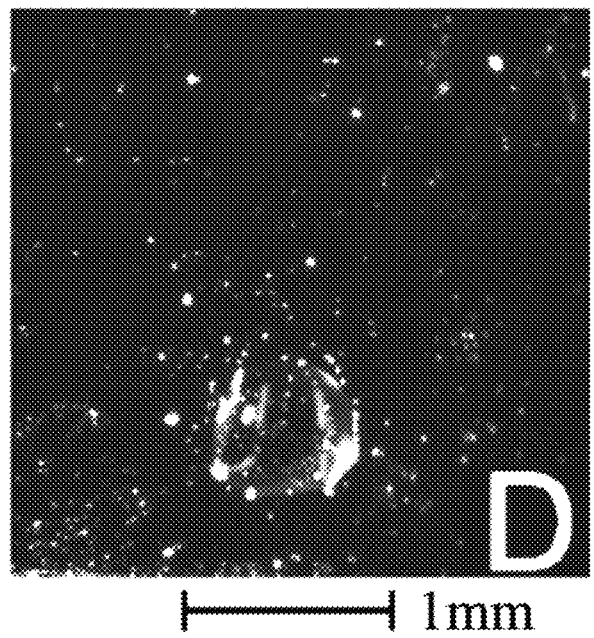
FIG. 17D is a time lapse image of 0.2 µL αCHCA matrix solution deposited on a bare silicon wafer without nickel catalyst or CNT. Crystal ring formation and subsequent pinning visible in the frame.
Figure 17E:
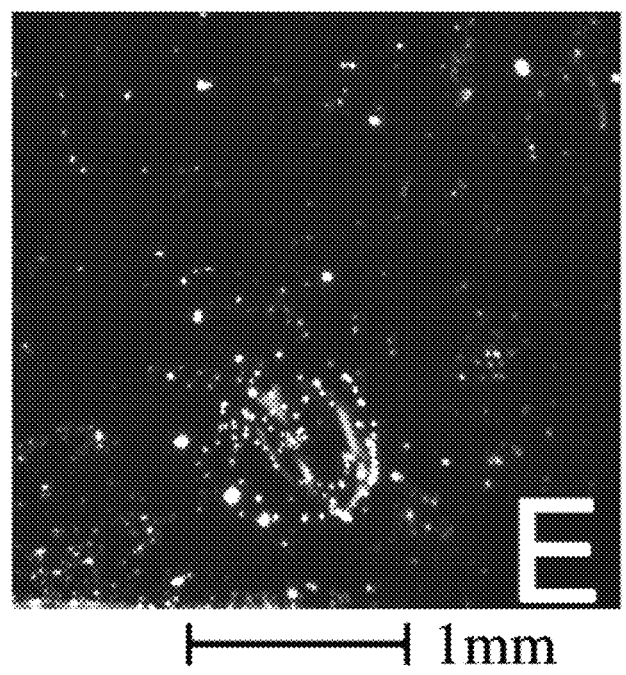
FIG. 17E is a time lapse image of 0.2 µL αCHCA matrix solution deposited on a bare silicon wafer without nickel catalyst or CNT.
Figure 17F:
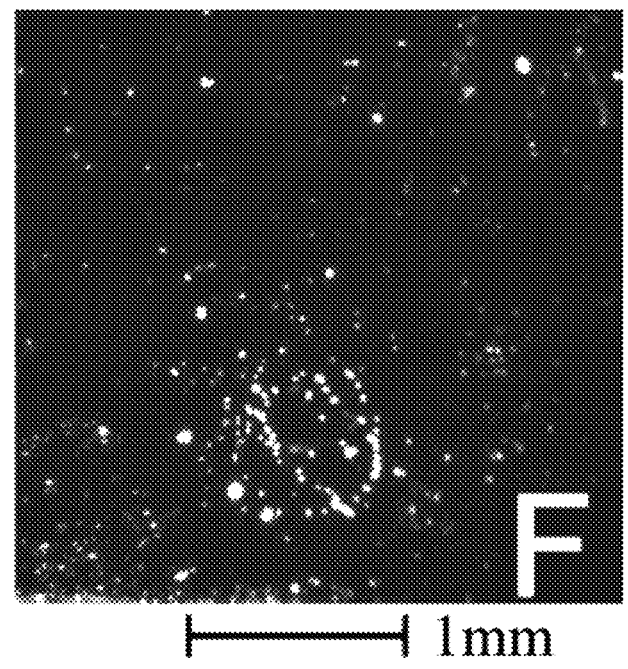
FIG. 17F is a time lapse image of 0.2 µL αCHCA matrix solution deposited on a bare silicon wafer without nickel catalyst or CNT.
Figure 18A:
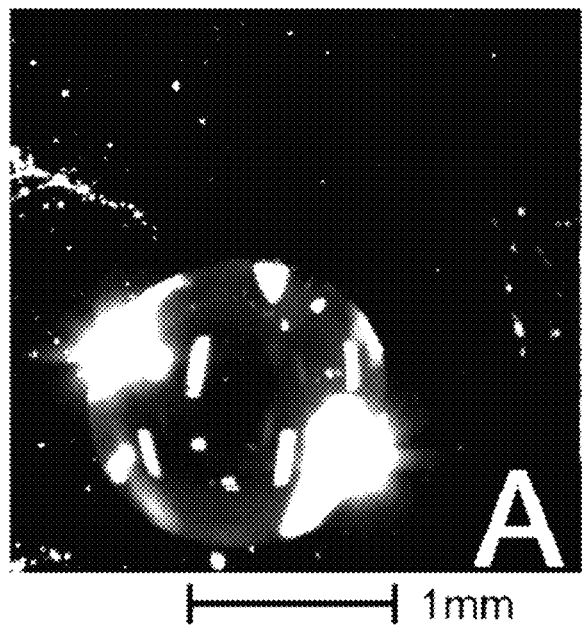
FIG. 18A is a time lapse image of 0.2 µL matrix solution deposited on a silicon wafer with a patterned area of nickel catalyst without carbon nanotube growth.
Figure 18B:
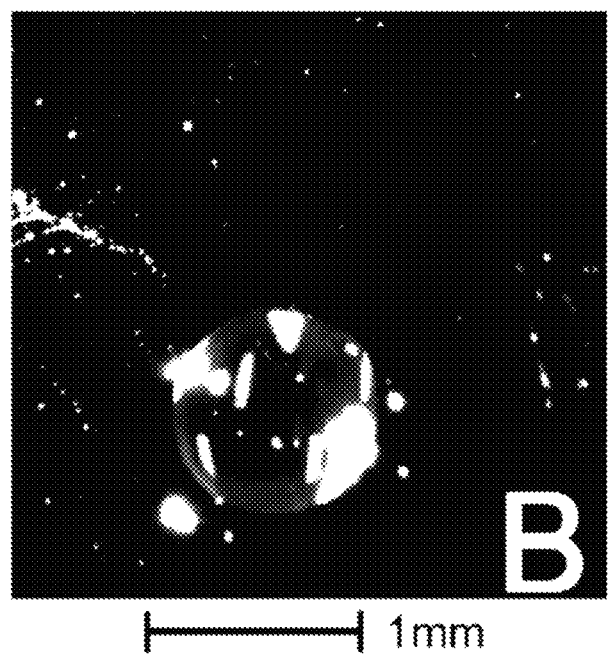
FIG. 18B is a time lapse image of 0.2 µL matrix solution deposited on a silicon wafer with a patterned area of nickel catalyst without carbon nanotube growth.
Figure 18C:
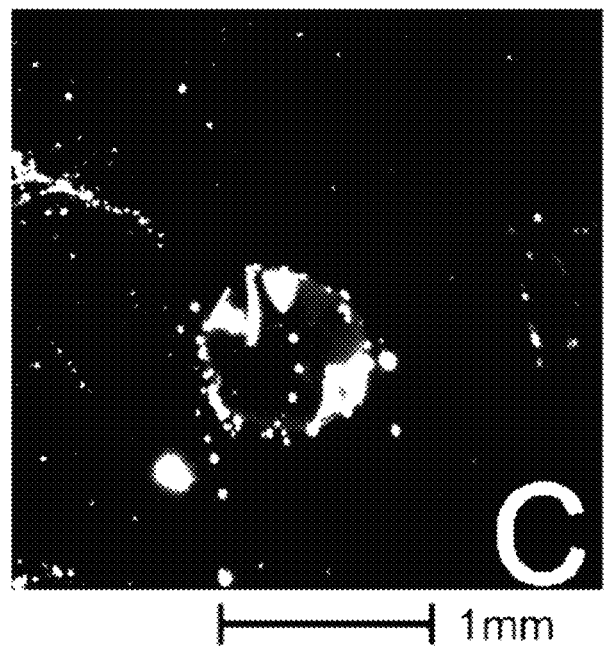
FIG. 18C is a time lapse image of 0.2 µL matrix solution deposited on a silicon wafer with a patterned area of nickel catalyst without carbon nanotube growth.
Figure 18D:
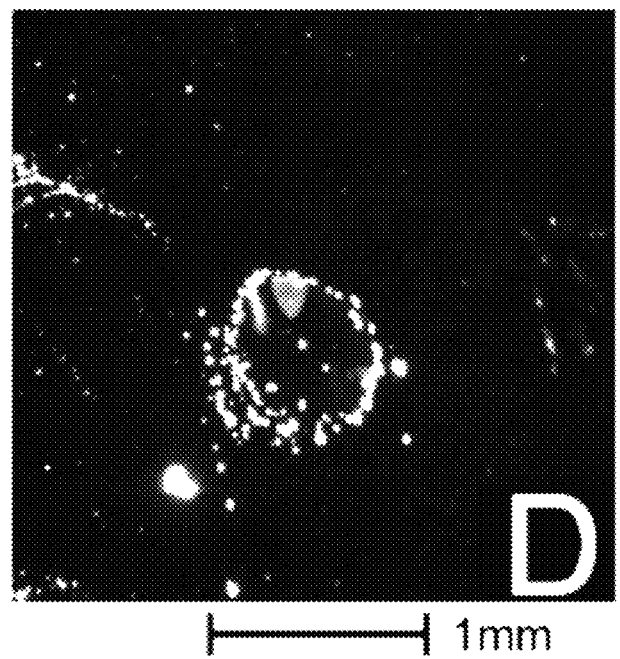
FIG. 18D is a time lapse image of 0.2 µL matrix solution deposited on a silicon wafer with a patterned area of nickel catalyst without carbon nanotube growth.
Figure 18E:
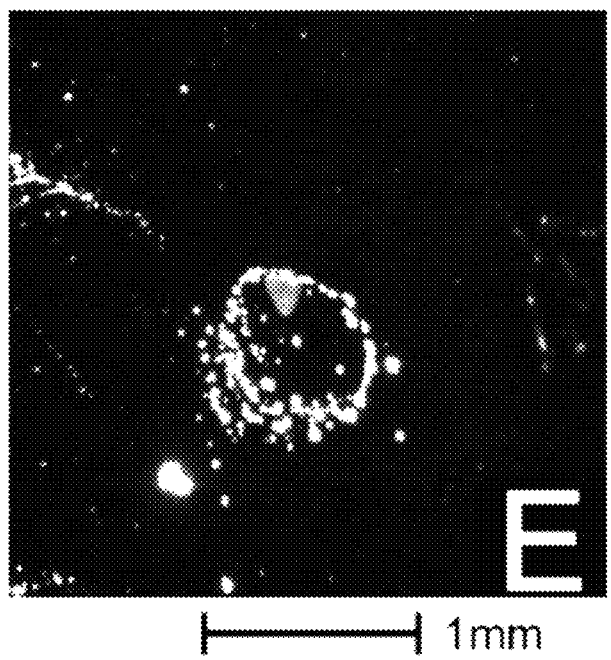
FIG. 18E is a time lapse image of 0.2 µL matrix solution deposited on a silicon wafer with a patterned area of nickel catalyst without carbon nanotube growth.
Figure 18F:
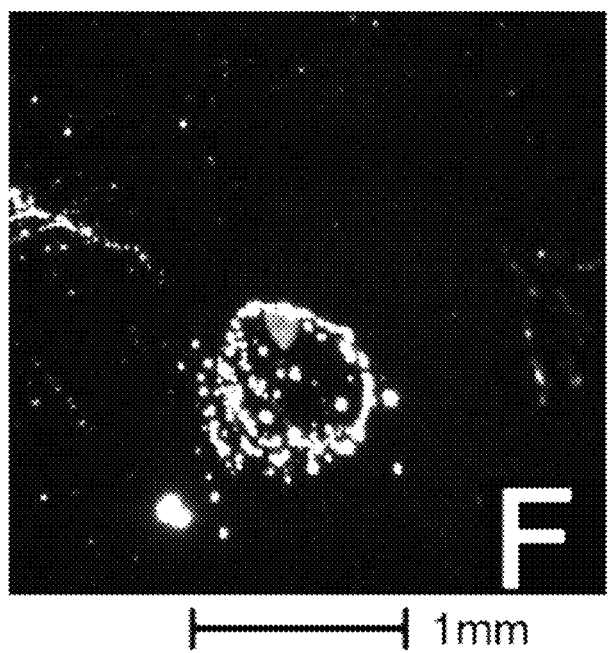
FIG. 18F is a time lapse image of 0.2 µL matrix solution deposited on a silicon wafer with a patterned area of nickel catalyst without carbon nanotube growth.
Figure 19A:
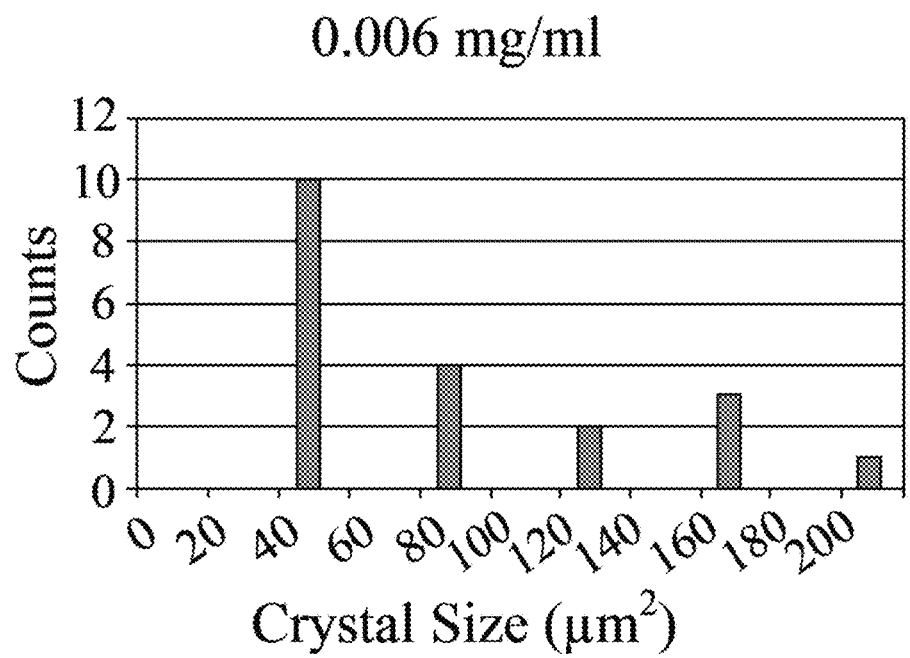
FIG. 19A is a graph showing the distribution of crystal sizes for matrix concentration of 0.006 mg/mL.
Figure 19B:
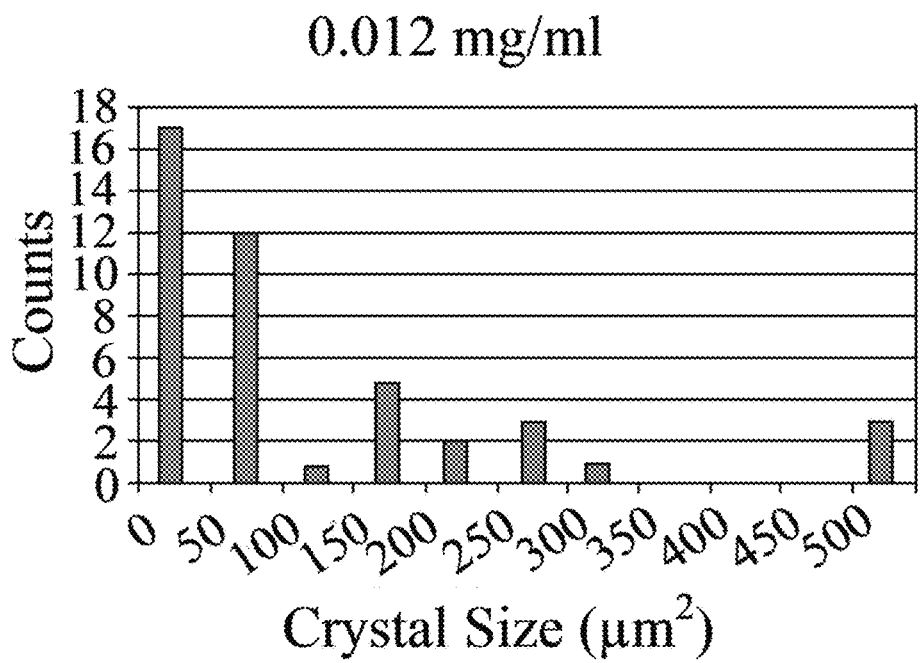
FIG. 19B is a graph showing the distribution of crystal sizes for matrix concentration of 0.012 mg/mL.
Figure 20A:
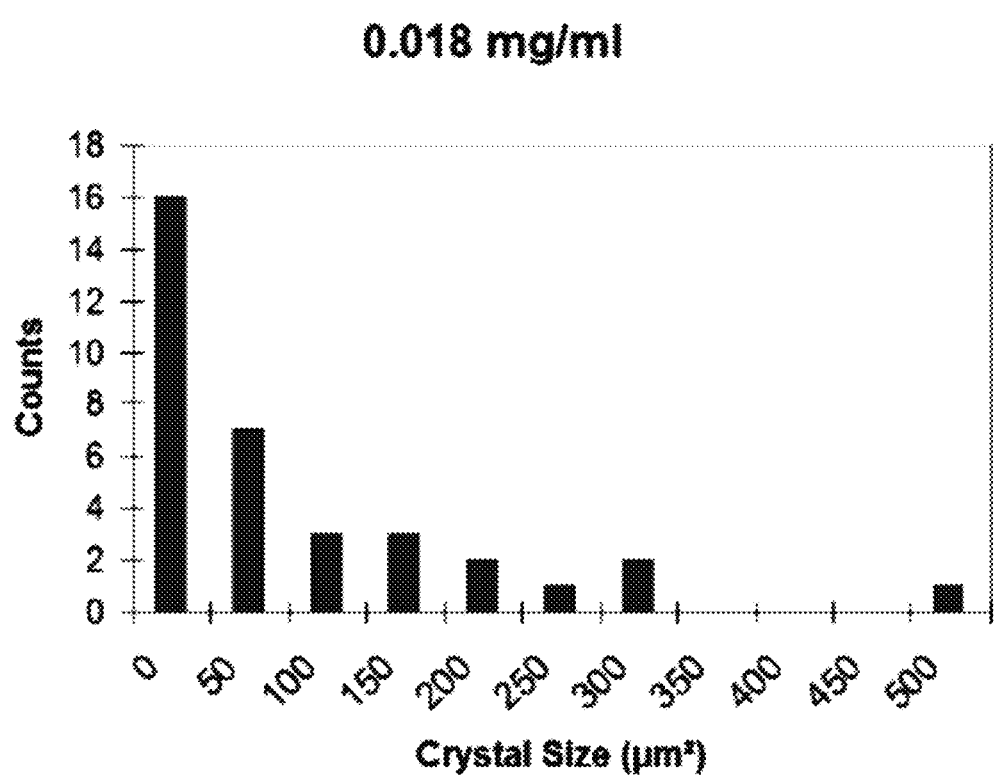
FIG. 20A is a graph showing the distribution of crystal sizes for matrix concentration of 0.018 mg/mL. The majority of crystals have an area of less than 200 $\mu m^2$.
Figure 20B:
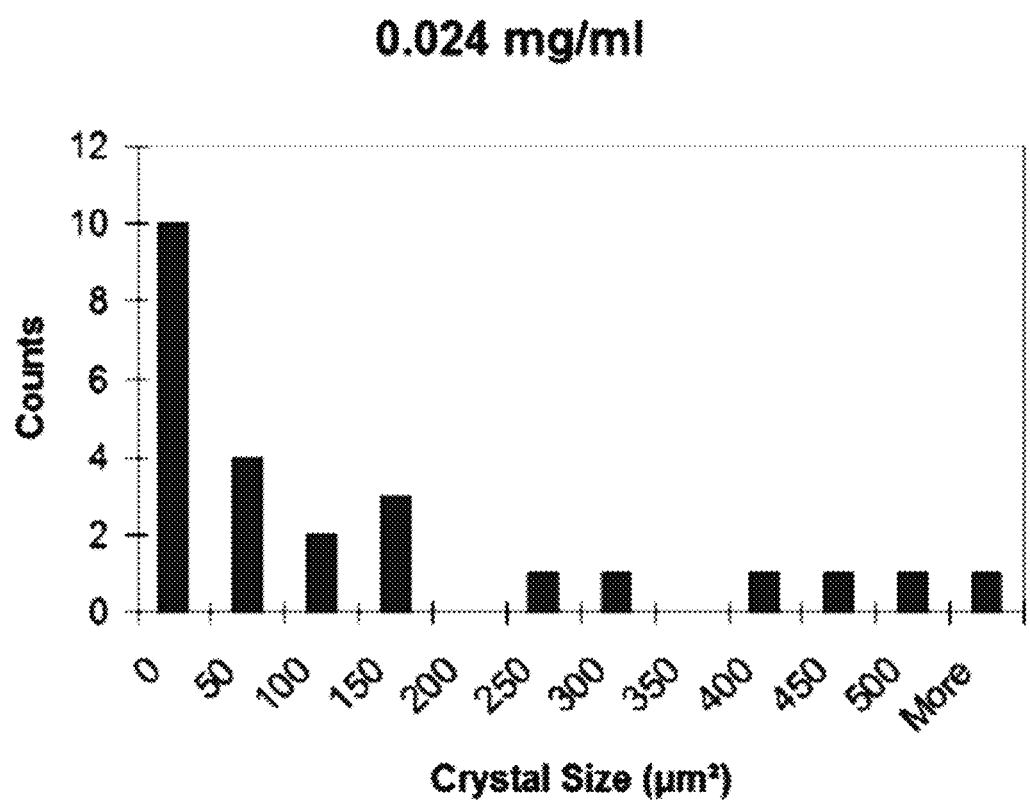
FIG. 20B is a graph showing the distribution of crystal sizes for matrix concentration of 0.024 mg/mL. The majority of crystals have an area of less than 200 $\mu m^2$.
Figure 21A:
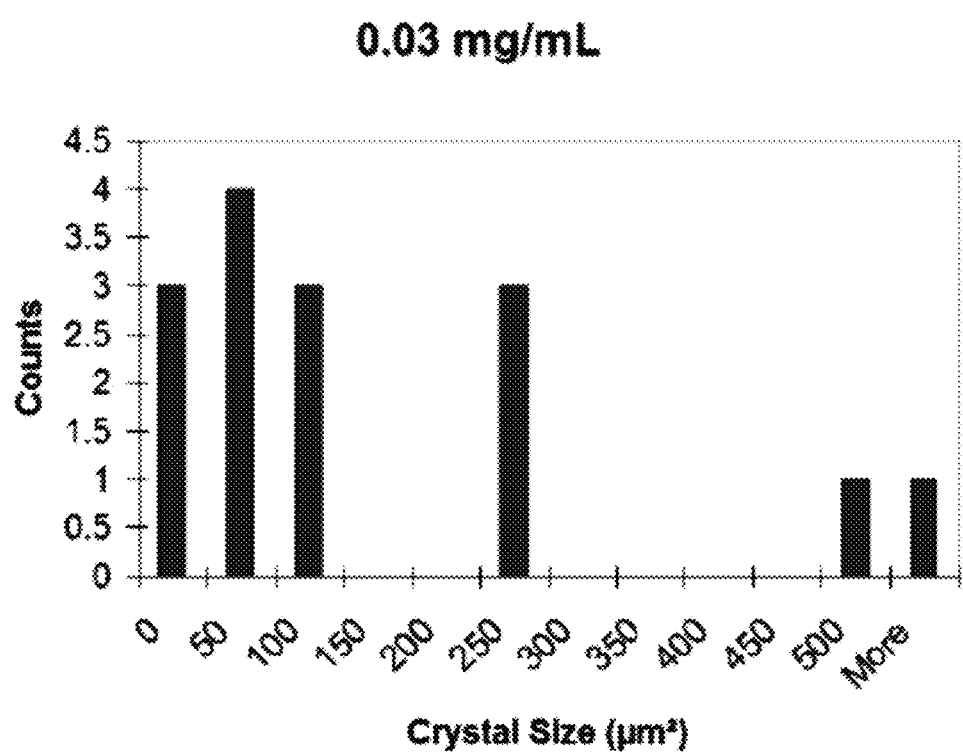
FIG. 21A is a graph showing the distribution of crystal sizes for matrix concentration of 0.03 mg/mL.
Figure 21B:
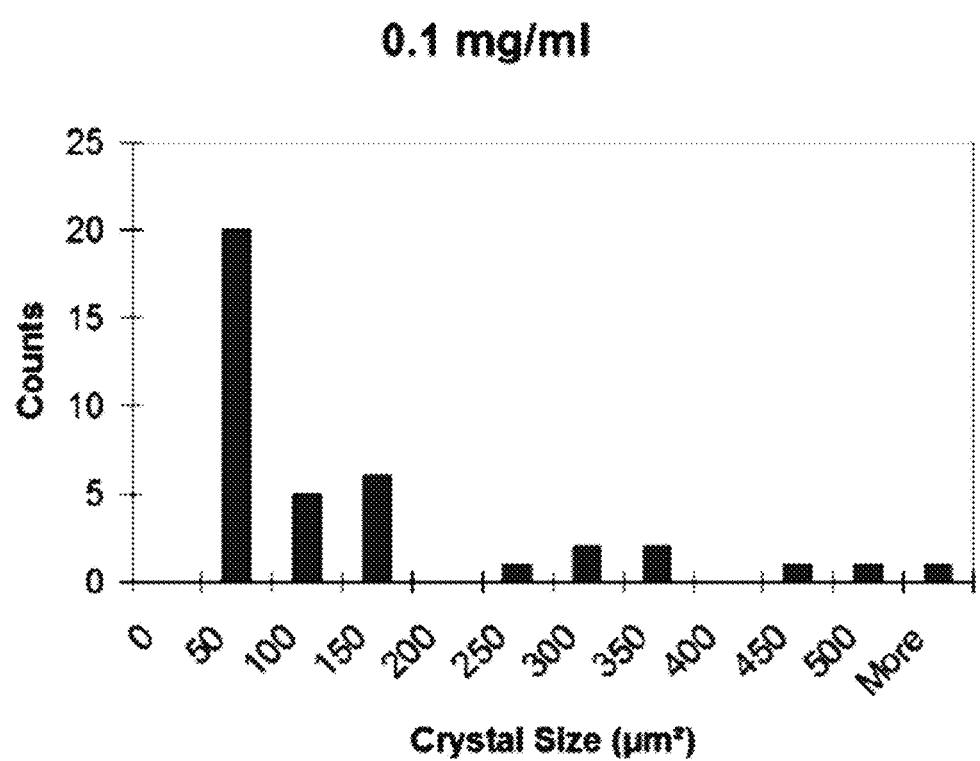
FIG. 21B is a graph showing the distribution of crystal sizes for matrix concentration of 0.1 mg/m.
Figure 22A:
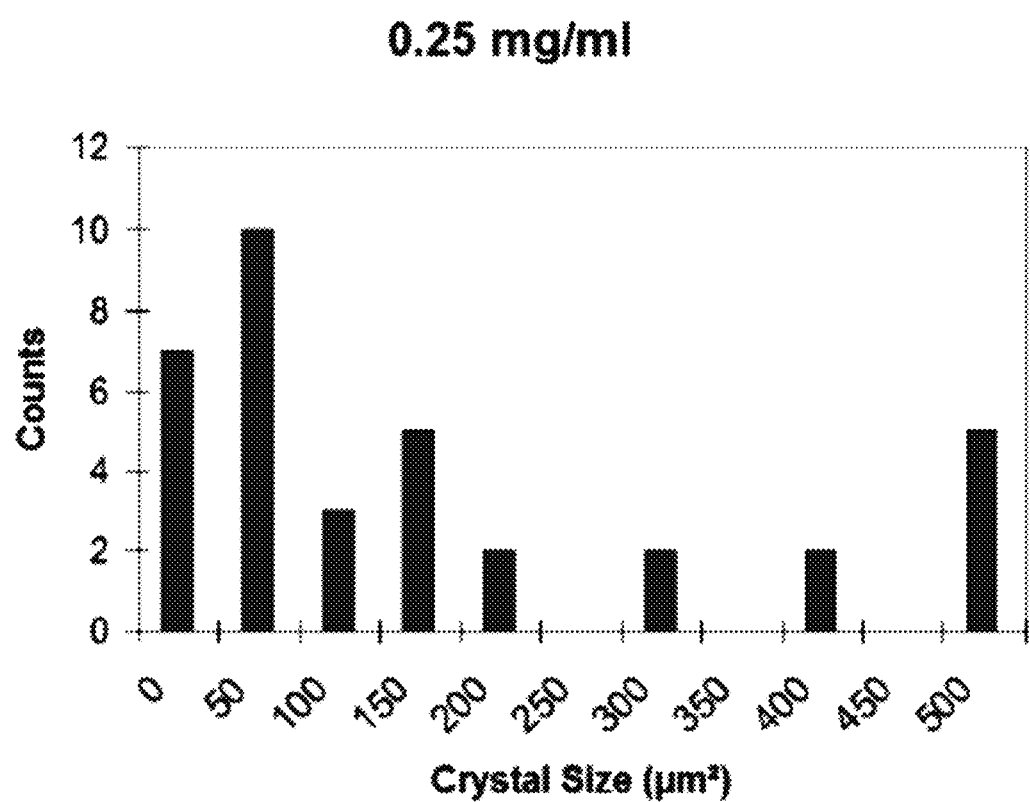
FIG. 22A is a graph showing the distribution of crystal sizes for matrix concentration of 0.25 mg/mL. The crystals larger than 500 $\mu m^2$ are possibly clusters of smaller crystals that could not be resolved due to overlap.
Figure 22B:
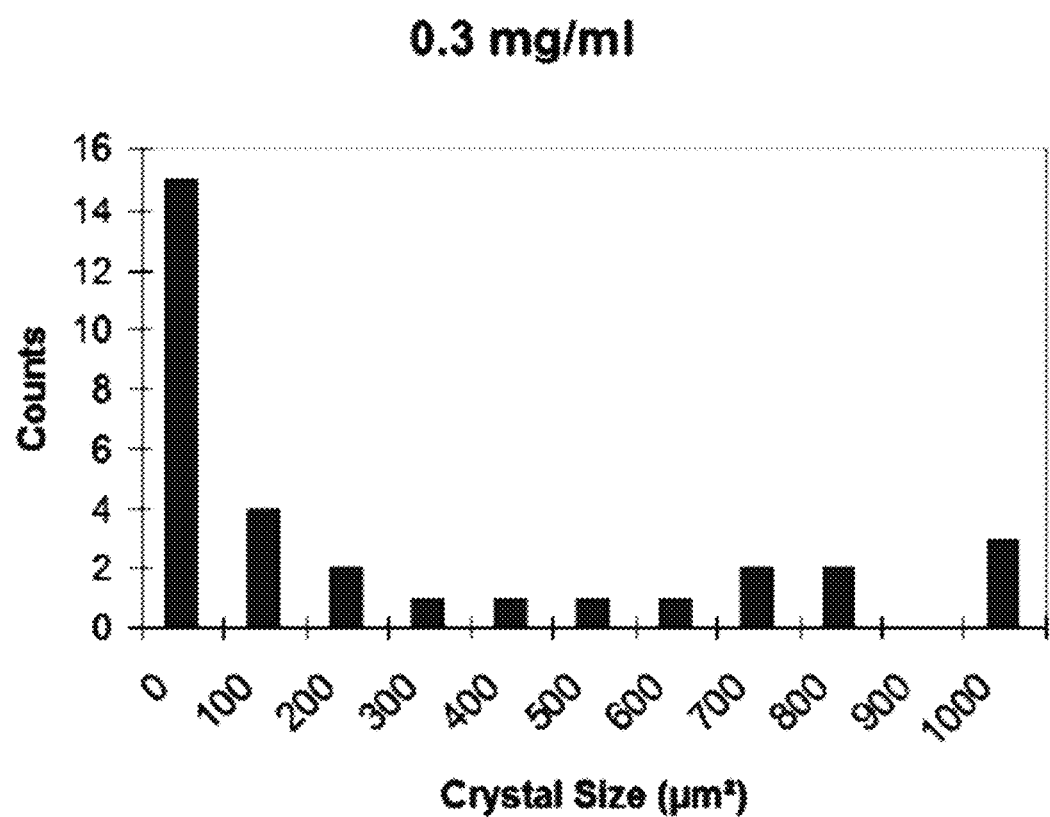
FIG. 22B is a graph showing the distribution of crystal sizes for matrix concentration of 0.3 mg/mL. The crystals larger than 500 $\mu m^2$ are possibly clusters of smaller crystals that could not be resolved due to overlap.
Figure 23A:
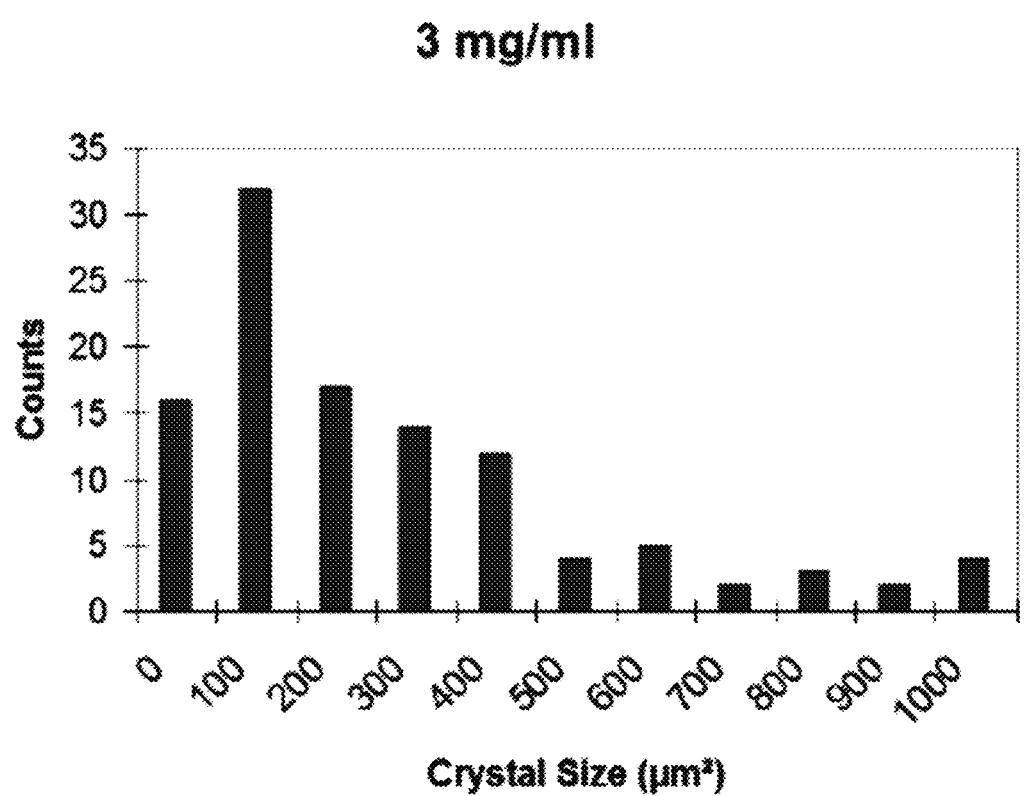
FIG. 23A are graphs showing the distribution of crystal sizes for a matrix concentration of 3 mg/mL.
Figure 23B:
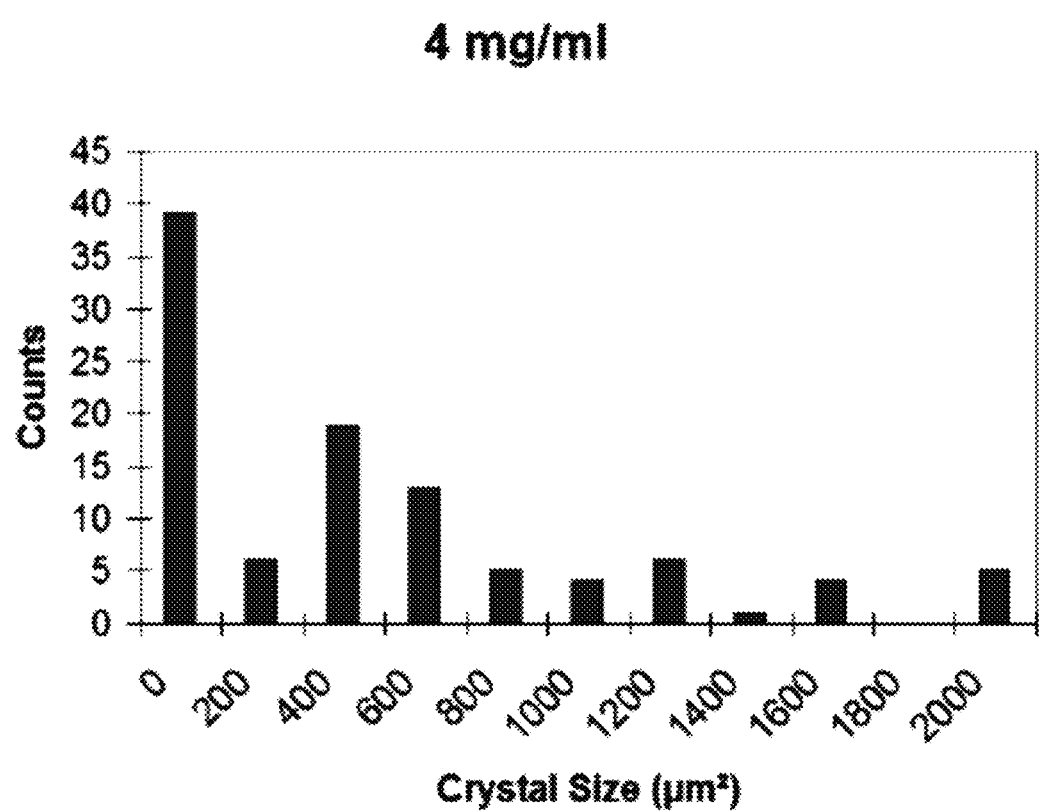
FIG. 23B are graphs showing the distribution of crystal sizes for a matrix concentration of 4 mg/mL.
Figure 24A:
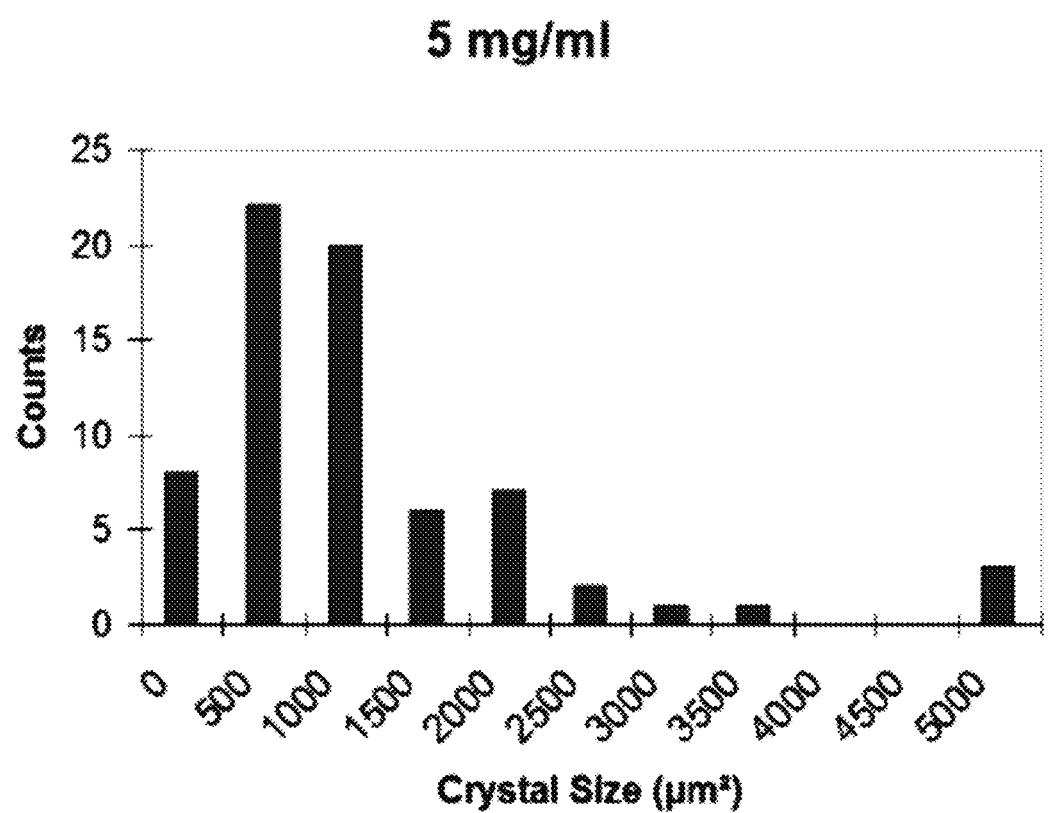
FIG. 24A is a graph showing the distribution of crystal sizes for matrix concentration of 5 mg/mL. A significant number of crystals have areas up to 2500 $\mu m^2$, which appear to be single crystals, rather than clusters of smaller ones.
Figure 24B:
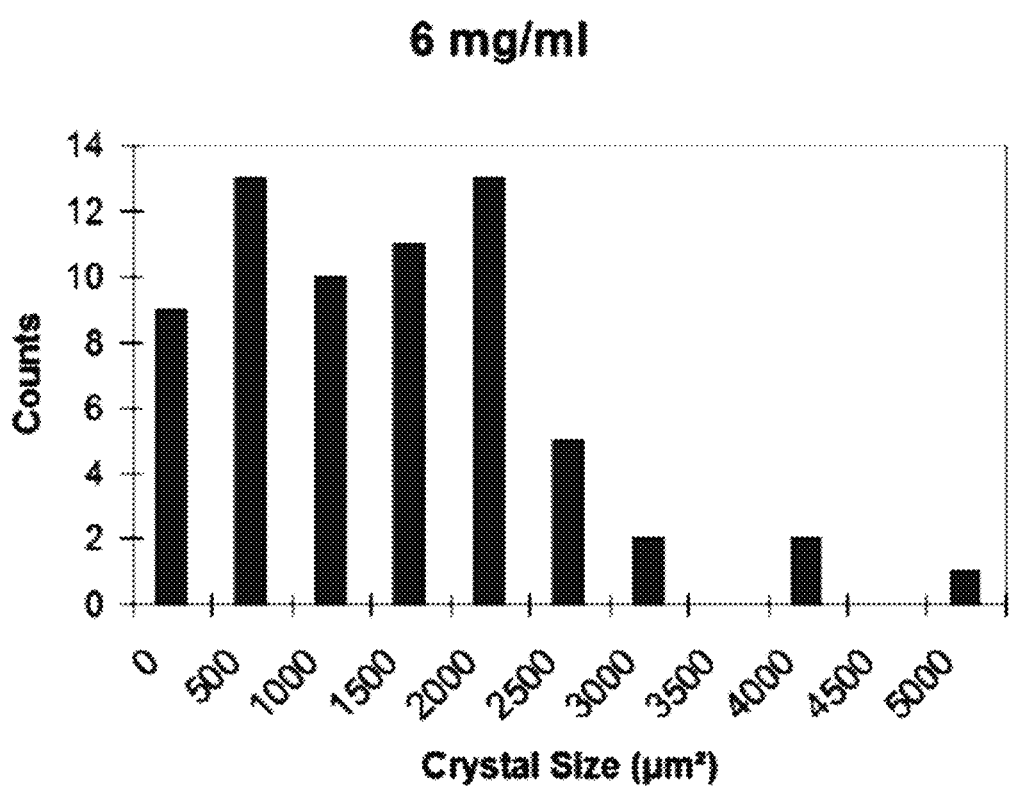
FIG. 24B is a graph showing the distribution of crystal sizes for matrix concentration of 6 mg/mL. A significant number of crystals have areas up to 2500 $\mu m^2$, which appear to be single crystals, rather than clusters of smaller ones.

As indicated previously, the carbon nanotubes grown using the PECVD technique possess multiple shells, i.e. multi-walled, with at least one shell displaying metallic properties, thereby dominating the conductive properties of the nanotube. Granger et al. (Granger, et al., *Highly extended image states around nanotubes*. Physical Review Letters, 2002. 89(13).) predicted that metallic carbon nanotubes can form extended image states due to external electron polarization of the CNT via image charge interaction with the electrons in the nanotube. The combined effect of these states forms a cylinder-shaped region surrounding the metallic carbon nanotube and is referred to as "tubular image states", with an effective potential a function of distance. Without being bound to any specific theory, a αCHCA and Salicylic acid are dissolved in acetonitrile and de-ionized water to matching concentrations, the molecules indicated similar, highly acidic pH values, which suggested a high probability that the dissolved molecules carry a charge. The quantity of charged molecules in combination with the tubular image states surrounding the carbon nanotubes could provide a mechanism for long range attraction, resulting in the enhanced preferential crystallization that was displayed during sample preparation, as seen in FIG. 16.

Earlier work by Schuerenberg et al. (Schuerenberg, et al., *Prestructured MALDI-MS sample supports*. Analytical Chemistry, 2000. 72(15): p. 3436-3442), involved sample concentration using a thin film of gold as the patterned hydrophilic anchor with a surrounding hydrophobic field of Teflon®. The solutions of matrix αCHCA crystallized onto the spots with a few interesting effects reported. Some droplets left the gold spot and crystallized on the surrounding Teflon®, which could suggest forces that could overcome potential hydrophilic attraction. Additionally, droplets that were intentionally deposited on the Teflon® field, not in contact with any gold anchors, also displayed lateral concentration, which could indicate that the final dried droplet diameter may be dependent on the initial solution concentration and solvent composition rather than the diameter of the anchor spot. As shown in FIGS. 17(A) through (F) and FIG. 18(A) through (F), deposition of matrix solution on the silicon surface surrounding patterned CNT's does not display any form of lateral concentration, which confirms the effect of the CNT's on the drying process.

Example 4

To further investigate the sample concentrating properties of CNT anchor spots, experiments were conducted using varying concentration of sample. Solutions were prepared. A solution of 1:1 volumetric ratio of acetonitrile to de-ionized water was prepared as a matrix solvent. Dry crystalline matrix αCHCA was weighed out with a Sartorius Research (Goettingen, Germany) model R200D digital precision balance and combined in a 1.5 mL Eppendorf® Safe-Lock Microcentrifuge tube (Westbury, N.Y.) with sufficient quantity of solution to achieve a matrix concentration varied over three orders of magnitude from 0.006 mg/mL to 6 mg/mL. Matrix concentrations above 6 mg/mL displayed insolubility and were not tested. All matrix solutions were prepared freshly and independently of each other in order to reduce possibility of concentration error. The samples were prepared by manually depositing 0.2 μL of solution from pipette to new carbon nanotube enhanced substrates (same parameters as previous experiment). The droplets were allowed to dry in ambient conditions (room temperature 23° C.), and time-lapse images were captured using the optical microscope described previously. Images of the samples after completed crystallization were analyzed using ImageJ software for crystal size, as seen in Table 6.

TABLE 6

Average crystal size of dried droplet
samples grouped by concentration.

| Matrix Concentration | Average Crystal Size |
|---|---|
| 0.006-0.03 mg/mL | 40 μm$^2$ |
| 0.1-0.25 mg/mL | 50-100 μm$^2$ |
| 3-6 mg/mL | 500-1000 μm$^2$ |
| over 6 mg/mL | Not available |

Histograms of crystal sizes for each deposition can be found in for the wide range of matrix depositions (concentrations 0.006 mg/mL to 6 mg/mL) are shown in FIGS. 19(A) through 24(B). The data was calculated using ImageJ software in particle analysis mode.

Figure 25:
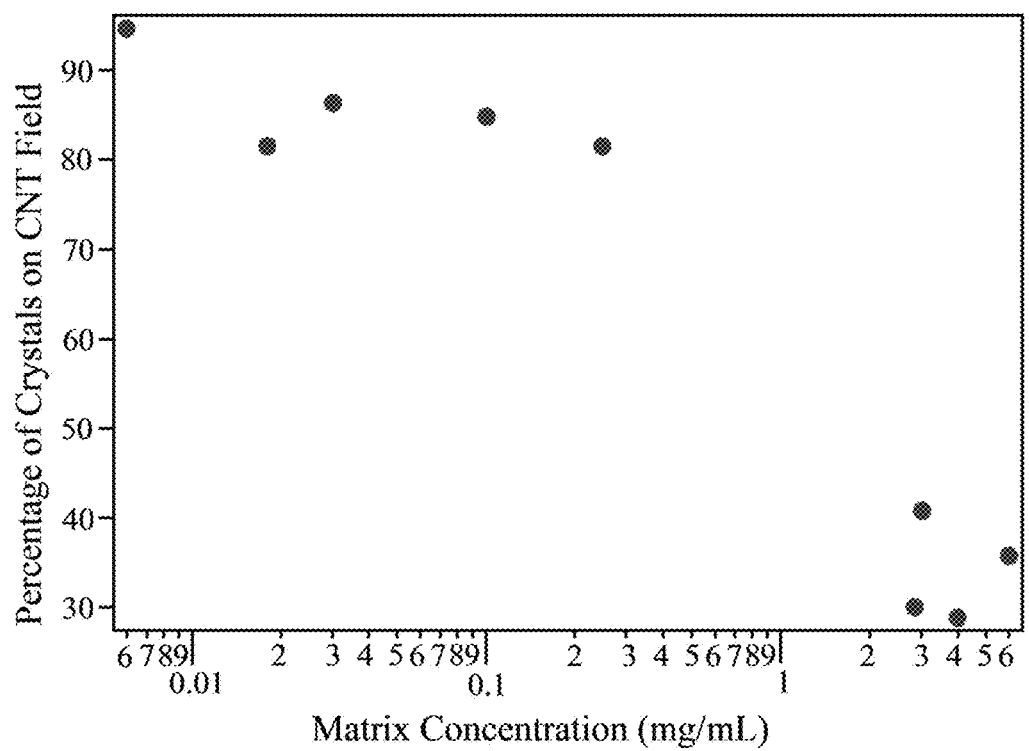
FIG. 25 is a graphs showing the crystallization percentage on CNT field for varying matrix solution concentrations

Further image analysis using the ImageJ software provided crystal count data for the entire image and for a select area defined by the location of the CNT field. The data provided a means for calculation of the crystal percentage formed on the carbon nanotubes relative to the surrounding area. An analysis of the concentration series images resulted in a range of data that was plotted using Wavemetrics Igor Pro software, as seen in FIG. 25. The percentage of matrix crystals that formed on the carbon nanotubes was very high for low matrix concentrations (94.6% for 0.006 mg/mL) as a result of droplet diameter reduction during evaporation on a hydrophobic surface. The midrange concentrations still performed well on the CNT enhanced substrate averaging 83.5% of all crystals on CNT's. Crystallization occurred on the carbon nanotubes first (less than 30 seconds after deposition) and droplet diameter reduction continued until the matrix concentration reached supersaturation and crystals precipitated on the surrounding silicon substrate. The crystals effectively pinned the contact line and prevented diameter reduction until increasing surface tension from continued evaporation was sufficient to overcome capillary force.

At very high matrix concentrations, matrix crystals covered the CNT field first (approximately 30 seconds), then precipitated onto the surrounding silicon wafer due to supersaturation of matrix in solution. The result was a low percentage (35%) of the total crystals deposited on the carbon nanotube area.

Example 5

Figure 26:
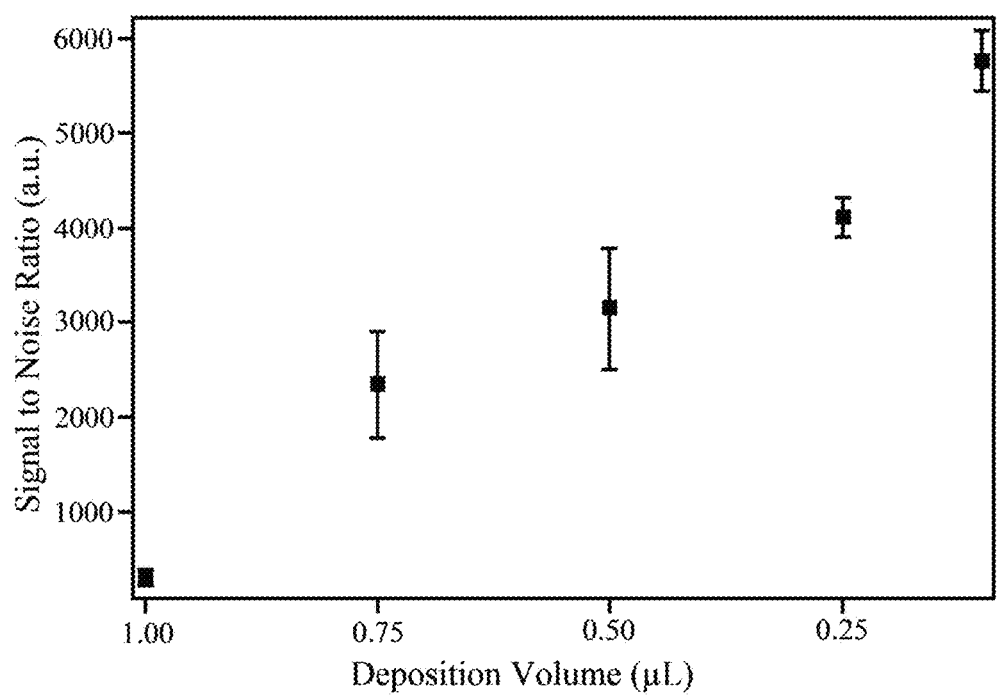
FIG. 26 is a graph showing the averaged signal to noise ratio values (in generic units) for the different deposition volumes. The error bars represent the standard error of the mean for the data points. The error bars surrounding each data point represent the standard error of the mean (Zar, *Biostatistical analysis.* 4th ed. 1999, Upper Saddle River, N.J.: Prentice Hall. 929; Sokal & Rohlf, *Biometry: The principles and practice of statistics in biological research.* 3rd ed. 1995, New York: W.H. Freeman and Co. 887), defined as the standard deviation of the error in the sample mean, and is calculated as the standard deviation divided by the square root of the sample size.

An initial experiment was conducted to identify the deposition volume for optimal MALDI signal. The deposition volume was varied while the solution concentration and ratio was held constant. A solution was prepared from 5 mg/mL matrix (αCHCA) mixed 1:1 with 250 fmol/µL of analyte solution peptide mixture 1, as disclosed in the previous examples. The values used were recommended by the operating instructions for calibration (Applied Biosystems). When mixed in a 1:1 ratio, the concentrations correspond to 13.2 nmol/µL of matrix to 125 fmol/µL of analyte ($1.32 \times 10^{-8}$ mol/µL and $1.25 \times 10^{-13}$ mol/µL, respectively) or a matrix to analyte molar ratio of approximately 106,000:1. Spotting volumes recommended by Applied Biosystems were 0.5 and 1 µL. Aliquots of solution with volumes from 1 µL to 0.1 µL were deposited on a standard MALDI plate via pipette and allowed to dry at room temperature. Two spots were prepared for each volume and each spot was interrogated numerous times with the MALDI laser. Analysis was performed immediately after deposition. Measurement noise was calculated with Data Explorer V.4 software from Applied Biosystems and given in root mean square (RMS) form. The graph in FIG. 26 displays the average signal-to-noise ratio (SNR) for the peptide des-Arginine-Bradykinin (m/z 904) over deposition volume. The signal-to-noise ratio increased steadily from 200 to well over 5500 (arbitrary units) as the deposition volume decreased from 1 µL to 0.1 µL (0.1 µL is the lower physical limit for the manual pipette used in these experiments). Similar trends were observed for other peptides in the mixture.

The Isoelectric Point (pI) for each of the peptides found in peptide Mixture I used in this research are listed in Table 7 and acid dissociation constants listed in Table 8. The values were calculated via the Isoelectric Point Service online tool (*EMBL WWW Gateway to Isoelectric Point Service*, EMBL Heidelberg—European Molecular Biology Laboratory) using the technique published by Lehninger's 1979 work *Biochimie* (Lehninger, *Biochimie*. 1979, New York: Worth Publishers). The range of net charge is given for the pH value of 2.75, which corresponds to the measured value of the αCHCA matrix solution. Samples were prepared by depositing 0.2 µL of a matrix/analyte solution described in Example 3, and calculated using the Isoelectric Point Service online tool (*EMBL WWW Gateway to Isoelectric Point Service*, EMBL Heidelberg—European Molecular Biology Laboratory).

TABLE 7

Isoelectric points for individual components of peptide Mixture 1.

| Analyte Component | Isoelectric Point (pI) | Net Charge at pH 2.75 |
|---|---|---|
| des-Arginine1-Bradykinin | 11.045 | +1.18 to +1.41 |
| Angiotensin I | 7.909 | +3.05 to +3.36 |
| Glu1-Fibrinopeptide B | 3.685 | +0.89 to +1.31 |
| Adrenocorticotropic hormone (ACTH) | 10.88 | +6.12 to +6.39 |

TABLE 8

Acid dissociation constants for matrix and analog molecules.

| Molecule | pKa Value |
|---|---|
| αCHCA | 1.17 |
| Catechol | 9.173-9.48 |
| Benzoic acid | 4.20 |
| Salicylic acid | 2.97 |
| Decanediol Alcohol | pKa value unknown |

Figure 27:
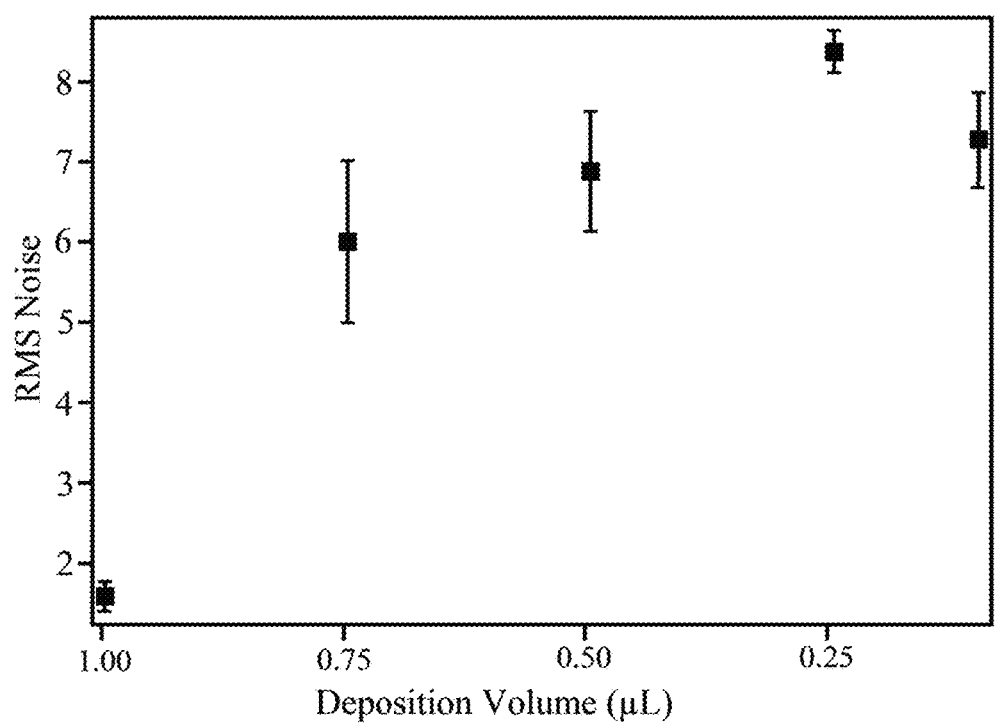
FIG. 27 is a graph showing the averaged RMS noise for measurements at different deposition volumes.

As shown in FIG. 27, RMS noise increased as deposition volume decreased with a maximum at 0.25 µL. From the data, the optimal deposition volume was calculated at 0.1 µL, providing a combination of the best SNR and local minimum of RMS noise. However aliquots with this volume are difficult to deposit reproducibly using a manual pipette due to mechanical fluctuation and droplet adhesion to the pipette tip. Therefore, based on SNR performance and ease of deposition, 0.2 µL was the deposition volume selected as the standard for use in future experiments.

Example 6

In an effort to determine the optimal matrix to analyte ratio, an experiment was conducted to vary both the matrix concentration (αCHCA) and the analyte concentration (peptide mixture 1). The results were analyzed to determine which combination produced the best signal-to-noise ratio (SNR) when investigated with the MALDI instrument. Three matrix concentrations (5 mg/mL, 3 mg/mL, 1 mg/mL), and six analyte concentrations (ranging from 250 fmol/µL to 25 fmol/µL) were investigated. The solutions were combined in equal parts by volume in individual 0.5 mL Eppendorf vials to represent each combination of matrix and analyte concentration, for 18 total variations. The combined solutions were spotted on the standard MALDI plate three times per solution with 0.2 µL deposition volume for a total of 54 spots. Each spot was interrogated five times with the MALDI instrument for a total of 270 spectra, and each spectrum was broken into four peaks of interest for a total of 1080 peaks.

Figure 28:
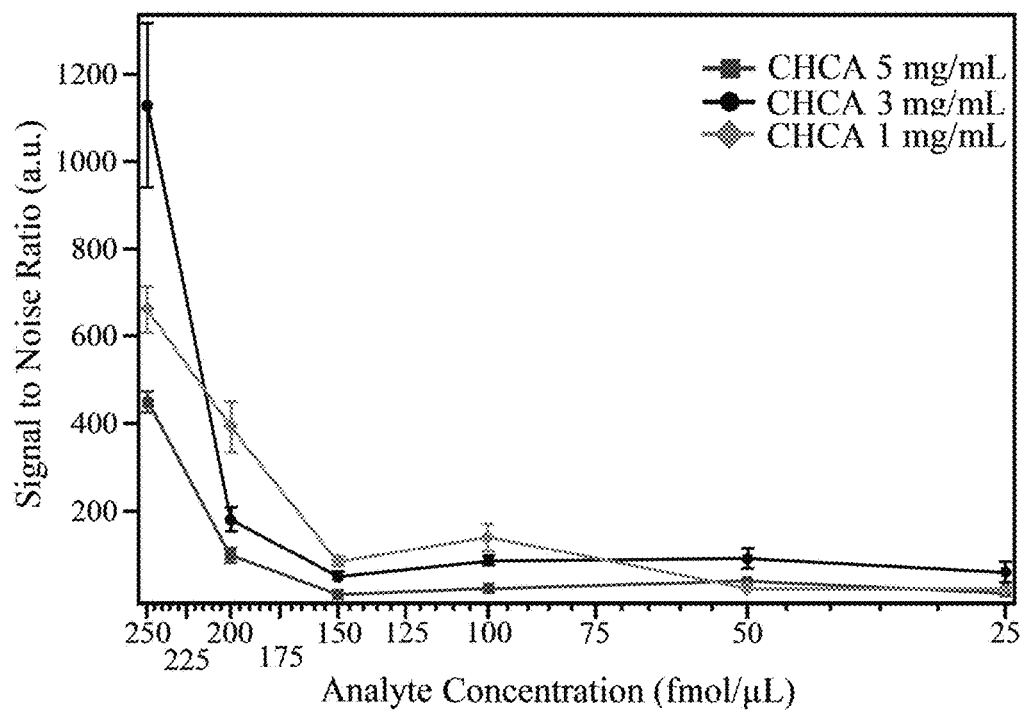
FIG. 28 is a graph showing the averaged SNR data (in generic units) versus analyte concentration grouped according to matrix concentration for peptide Angiotensin I (m/z 1297).

The data from the experiment is plotted in graphs of signal-to-noise ratio versus analyte concentration and grouped according to matrix concentration. The graph for peptide Angiotensin I (m/z 1297), is shown in FIG. 28 and is representative of the results from the other peptides. The data in the graph indicates that change in analyte concentration has a stronger influence on MALDI performance than matrix concentration for the tested ranges. The decrease in SNR is significant for the reduction in analyte concentration from 250 to 150 fmol/µL.

Figure 29:
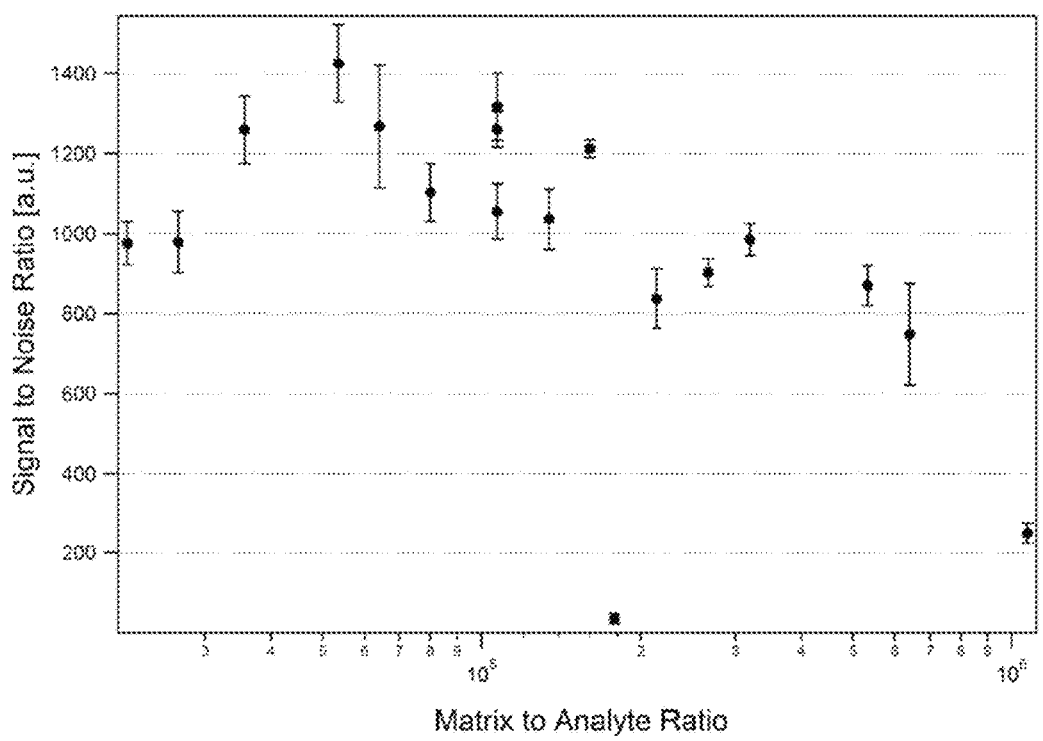
FIG. 29 is a graph showing the averaged SNR data (in generic units) for des-Arginine-Bradykinin (m/z 904) plotted versus the matrix to analyte molar ratio of the solution used for deposition.

To better illustrate the effect of change in matrix and analyte concentration in the MALDI process, signal-to-noise ratio data collected from the same experiment was graphed against the matrix-to-analyte molar ratio, seen in FIG. 29. The data is for peptide des-Arginine-Bradykinin (m/z 904) and represents all 18 combinations of solutions. The samples that produced the best signal-to-noise values were prepared from solutions that had matrix-to-analyte molar ratios between 35,000 and 100,000 to 1. This range verifies the value (approx 100,000:1) given in the operating instructions for CALMIX 4700.

The combination of 3 mg/mL of matrix with 250 fmol/µL of analyte (which corresponds to a matrix-to-analyte molar ratio of 63,400:1) performed consistently for both peptides (des-Arginine-Bradykinin and Angiotensin I) and was used as the standard for the subsequently discussed experiments.

Example 7

Figure 30:
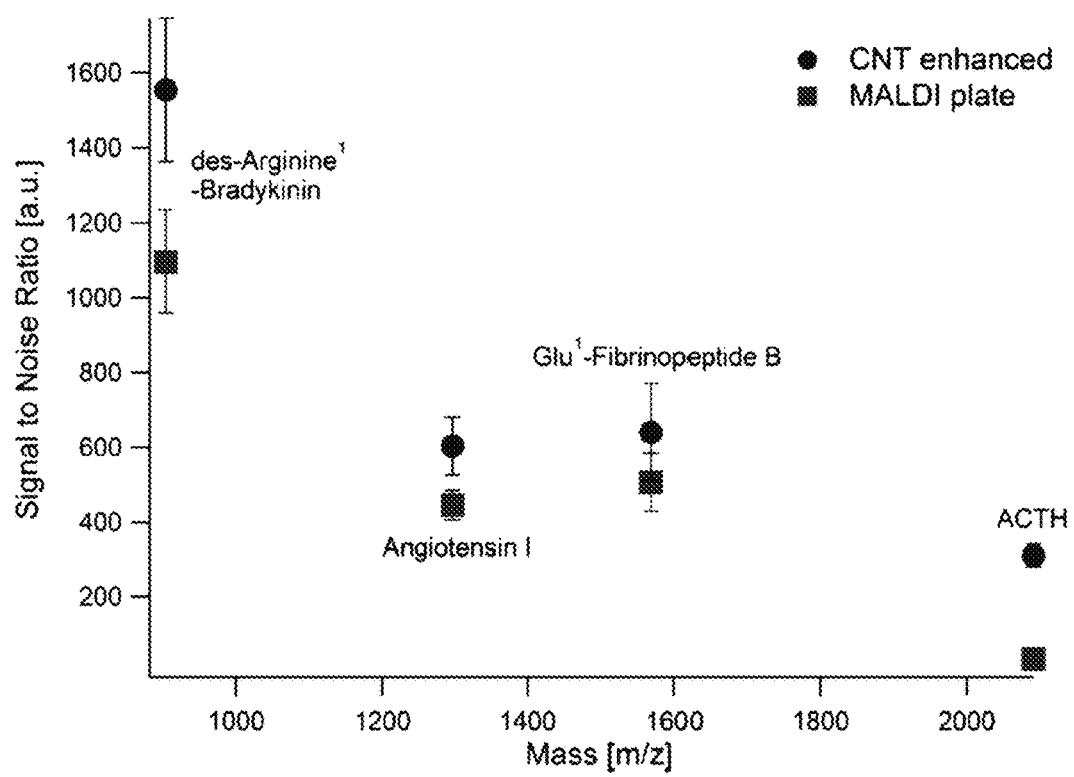
FIG. 30 is a graph showing the Signal to Noise Ratio (SNR) (in generic units) for the four peptides in mixture 1 on the standard MALDI plate and the CNT-enhanced substrates.

Performance Comparisons were performed on Standard and CNT-enhanced MALDI Substrates. Two sample supports of each type (standard MALDI plate and CNT enhanced substrate) were prepared, using the procedure described in Example 1 for the CNT. The solution used for deposition contained 3 mg/mL of αCHCA matrix and 250 fmol/µL of peptide mixture 1. The samples were investigated with an Applied Biosystems Voyager DE STR MALDI-TOF in positive-ion reflector mode with a 200 nano-second delayed extraction and 25 kV accelerating voltage. Ionization was achieved using a 355 nm wavelength laser with 20 Hz firing frequency. Laser intensity was adjusted to slightly above the threshold level for each sample to maintain mass resolution and minimize noise. Data was collected for 250 consecutive laser shots per spectrum. AppliedBiosystems Data Explorer (version 4) software was used for spectrum analysis. In order to calculate the signal to noise ratios, the signal value from each independent peak was divided by the root mean square (RMS) noise from the individual spectra that was calculated using the Data Explorer software. Five spectra were collected from different locations on each sample with 250 laser shots collected per spectrum. The signal-to-noise values were averaged for each sample and the data separated into four peak groups with each peak corresponding to a different peptide in the calibration mixture. The results are shown in FIG. 30. The error bars surrounding the data points represent the standard error of the mean (Zar, *Biostatistical analysis*. 4th ed. 1999, Upper Saddle River, N.J.: Prentice Hall. 929).

Data from the samples deposited on the carbon nanotube-enhanced substrate indicates an increased signal to noise ratio compared to that of the standard MALDI sample plate. The raw signal strength from the CNT-enhanced samples was slightly higher than that of the standard samples, however the RMS noise was significantly lower (22.11 for the CNT-enhanced and 32.09 for the standard substrate), which is the main factor in the SNR increase. Des-Arginine1-Bradykinin (m/z 904) shows a greater SNR increase than the other peptides, possibly due to differences in molecular weight as Puretzky et al. (Puretzky, et al., *Imaging of vapor plumes produced by matrix assisted laser desorption: A plume sharpening effect*. Physical Review Letters, 1999. 83(2): p. 444-447) demonstrated that lighter molecules travel faster through the desorption plume from the sample to the instrument, which can effect ionization via collisions in the matrix plume. The analyte ACTH (m/z 2093) deposited on the CNT enhanced substrate also demonstrated an increase in signal strength over the sample on the MALDI plate. Recently published research has shown that the aromatic carbon rings in the structure of amino acids phenylalanine (Piao, L. Y., et al., *Adsorption of L-phenylalanine on single-walled carbon nanotubes*. Journal of Physical Chemistry C, 2008. 112(8): p. 2857-2863; Piao, et al., *The Adsorption of L-Phenylalanine on Oxidized Single-Walled Carbon Nanotubes*. Journal of Nanoscience and Nanotechnology, 2009. 9(2): p. 1394-1399), tryptophan (Li, et al., *Direct measurements of interactions between polypeptides and carbon nanotubes*. Journal of Physical Chemistry B, 2006. 110(25): p. 12621-12625; Wang, et al., *Peptides with selective affinity for carbon nanotubes*. Nature Materials, 2003. 2(3): p. 196-200), and tyrosine (Salzmann, et al., *Interaction of tyrosine-, tryptophan-, and lysine-containing polypeptides with single-wall carbon nanotubes and its relevance for the rational design of dispersing agents*. Journal of Physical Chemistry C, 2007. 111(50): p. 18520-18524), interact with the surface of carbon nanotubes. The interaction has the potential to enhance the affinity of the peptide for the carbon nanotube surface. Additionally, the aromatic rings in the matrix αCHCA likely interact through π-bonds with these aromatic amino acids (Piao, et al., *Adsorption of L-phenylalanine on single-walled carbon nanotubes*. Journal of Physical Chemistry C, 2008. 112(8): p. 2857-2863), resulting in a localization of the peptide in the vicinity of a matrix molecule or crystal. This localization of the peptides can enhance charge transfer via the hopping mechanism calculated by Setz et al. (Setz & Knochenmuss, *Exciton mobility and trapping in a MALDI matrix*. Journal of Physical Chemistry A, 2005. 109(18): p. 4030-4037) to be an average of seventeen molecular diameters. A greater number of peptides in contact with charge donating matrix molecules have the potential to increase the charge transfer efficiency per laser shot, which may result in a larger MALDI signal as seen in FIG. 30.

Figure 31:
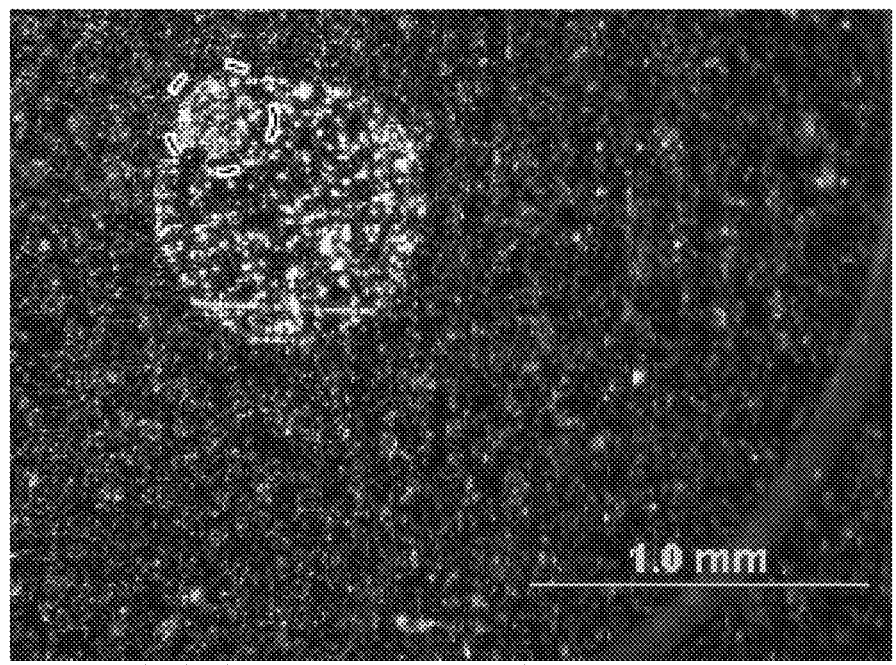
FIG. 31 depicts a solution of 250 fmol peptide standard in 3 mg/ml HCCA matrix compound deposited MALDI samples on standard "anchor-plate" (Bruker). A ~0.8 mm diameter deposition area occurred encompassing the anchor spot (circled on top left), but considerably exceeding it.

Additional analyte/matrix crystallization was compared on traditional target supports versus carbon nanotube-seeded target supports. 0.2 µL aliquots of 250 fmol/µL Mariner CALMIX 1 peptide standard solution (des-Arginine-Bradykinin, Angiotensin I, Glu-Fibrinopeptide, and Adrenocorticotropic Hormone (ACTH); Applied Biosystems (Foster City, Calif.)) mixed in a 3 mg/ml HCCA matrix, dropped onto a conventional Bruker "anchor plate" and allowed to evaporate. SEM images of the resulting solid matrix/analyte deposits display a diffuse 200 µm diameter anchor spot residue, seen in FIG. 31. Matrix concentrations were varied proportionally with the analyte, from 0.3 mg/mL to 0.006 mg/mL HCCA, to keep the matrix to analyte ratio constant. The matrix/analyte deposit is considerably larger (~0.8 mm diameter) than the anchor spot (circled) on the Bruker target support. It was also noted that this large matrix/analyte deposit was similar in magnitude to previous studies on MALDI matrix/analyte deposition (Schuerenberg, et al., "Prestructured MALDI-MS sample supports", Analytical Chemistry 72 (15), pp. 3436-3442 (2000).).

Figure 32:
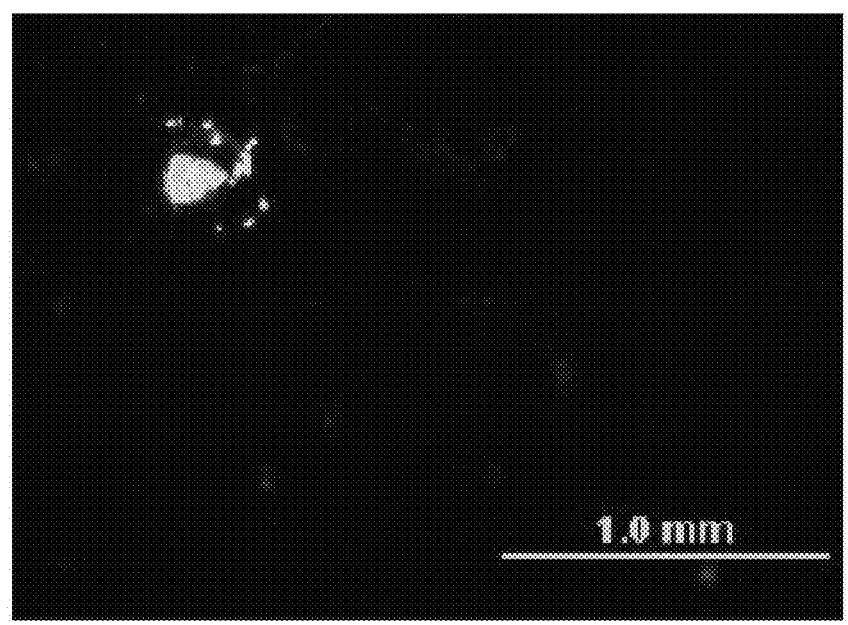
FIG. 32 depicts a solution of 250 fmol peptide standard in 2.5 mg/ml HCCA matrix compound deposited on a carbon nanotube "nucleation enhancing" anchor spot on a Si wafer. Only very few crystallites are located outside the central nanotube area due to early nucleation onset on the nanotube area.

The Mariner CALMIX 1 peptide standard was prepared again, and mixed in a 2.5 mg/ml HCCA matrix compound. 0.2 µL aliquots of 250 fmol/µL standard were dropped onto a carbon nanotube target support and allowed to evaporate. In contrast to the traditional Bruker support, deposition on the carbon nanotube anchor spot resulted in an almost complete concentration of the analyte/matrix crystals onto the ~150 µm diameter nanotube area, as seen in FIG. 32.

Figure 33A:
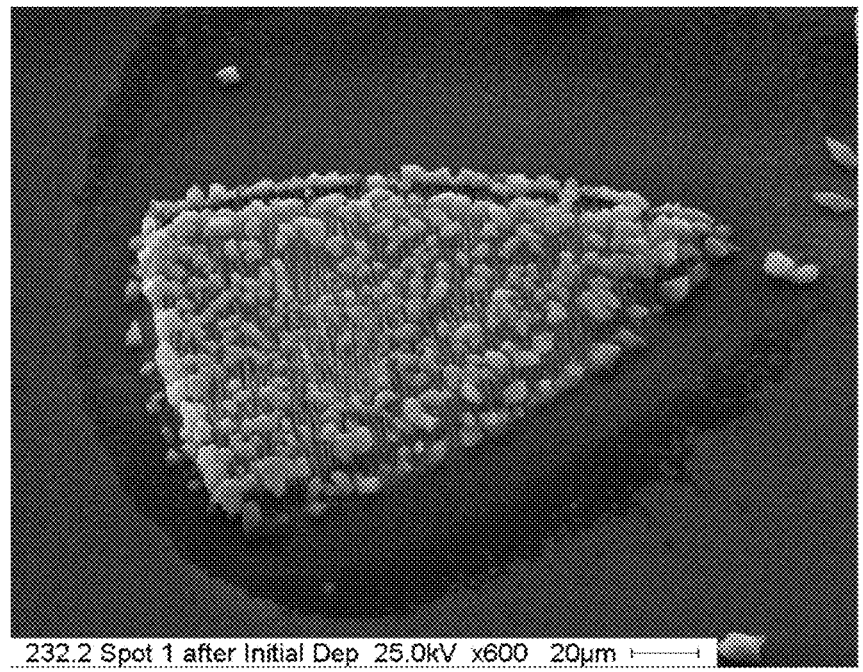
FIG. 33A is a scanning electron microscopy image of the carbon nanotube patch used as anchor spot. The matrix/analyte preferentially crystallizes onto the carbon nanotubes and is concentrated into a ~150 µm diameter area.
Figure 33B:
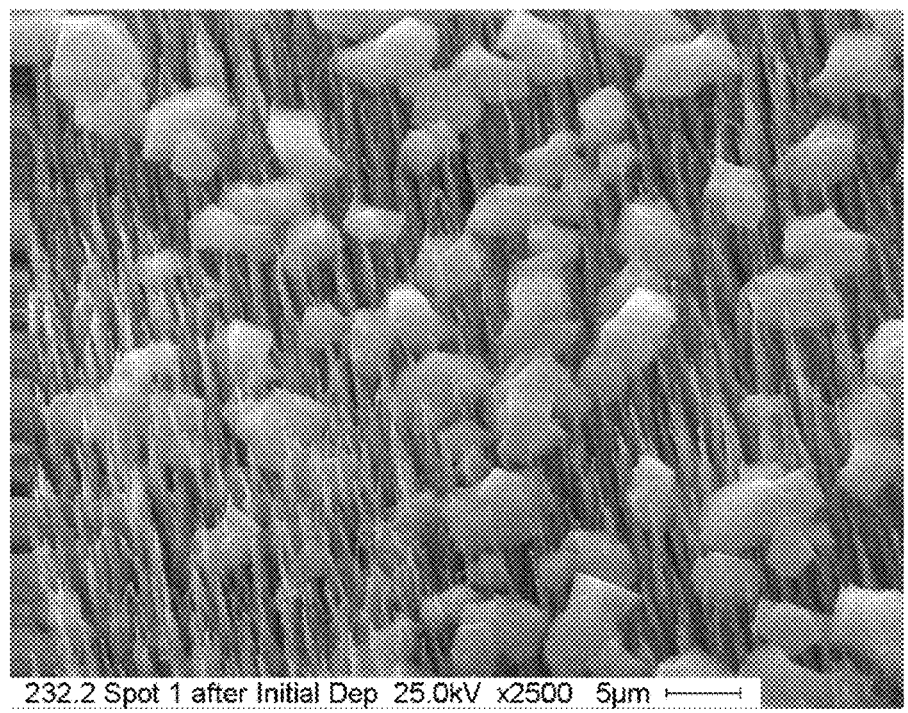
FIG. 33B is a scanning electron microscopy image of the carbon nanotube patch used as anchor spot. A magnified image of matrix/analyte crystals formed on the top of the nanotubes.

Scanning electron microscopy images were captured of the deposit on top of the carbon nanotube covered area, seen in FIGS. 33(A) and (B). As can be seen in FIG. 33(A), the area covered by the initial droplet (dark region) was significantly larger than the anchor spot. The crystallization of matrix and analyte preferentially occurred on the carbon nanotubes, with only a few crystals forming on the empty target support. Closer analysis of the anchor spot, seen in FIG. 33(B), shows the analyte/matrix crystals deposited on the peaks of the carbon nanotubes, documenting that the crystalline deposit forms on top of the carbon nanotubes.

Example 8

The use of a carbon nanotube-enhanced substrate was shown to increase average SNR values for peptide signals collected via the MALDI process. The experiment was performed for a single solution concentration. In order to investigate substrate performance over a range of solution concentrations, and to find the detection limit, substrate performance was tested at low analyte concentrations. This is important for applications involving small quantities of analyte or highly diluted solutions.

Multiple samples were prepared according to the procedure given in Example 3. The concentrations of analyte peptide mixture 1 ranged from 25 fmol/µL to 0.5 fmol/µL. Two samples were prepared on each type of substrate for each concentration of solution for a total of 24 samples. The matrix concentration was reduced appropriately to keep the matrix to analyte molar ratio constant at 63,400:1, which corresponded to the ratio of 3 mg/mL matrix with 250 fmol/μL analyte that was selected as the standardized ratio established in Example 6. The deposition volume was the same as in the earlier experiments, 0.2 μL. The final amount of analyte deposited onto the substrates ranged from 3.25 femtomoles to 65 attomoles, as calculated for analyte component Glu1-Fibrinopeptide B and the SNR data plotted in FIG. 34.

The average signal from the samples on the standard MALDI plate declined with decreasing analyte concentration and no signal was detected below 130 attomols. The samples deposited on carbon nanotube-enhanced substrates showed an overall increase in intensity with a significant gain in the 250 attomol range. In addition, the CNT spotted sample produced a signal at the minimum analyte concentration used for this experiment. The error bars surrounding the data points represent the standard error of the mean.

Figure 34:
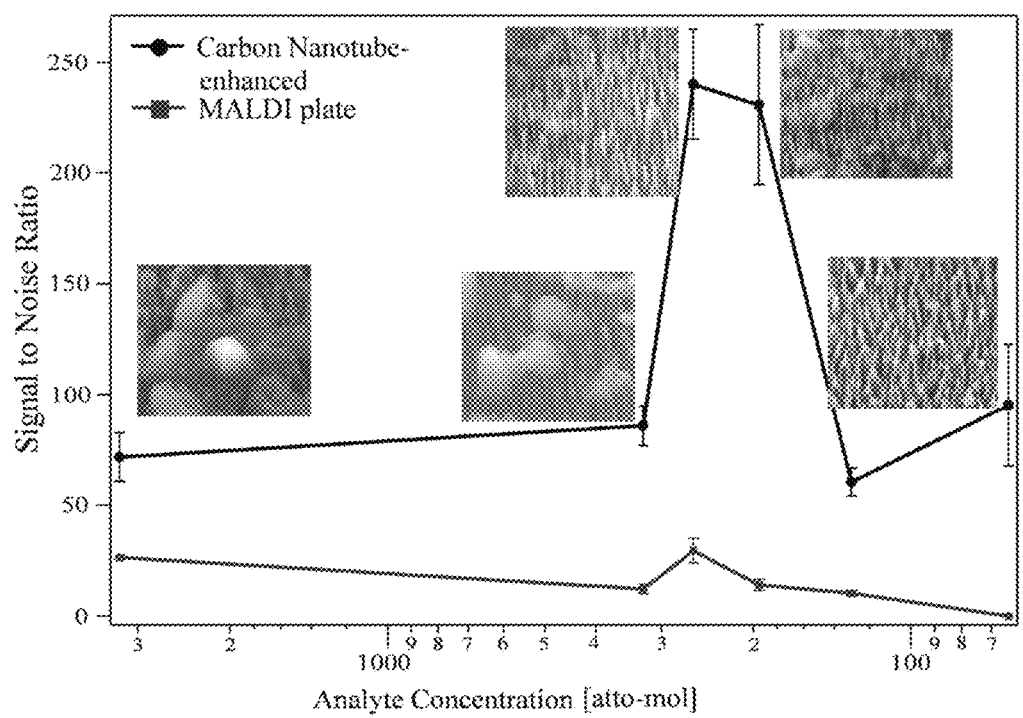
FIG. 34 is a graph comparing the MALDI-TOF-MS signal-to-noise ratio of the Glu-Fibrinopeptide 1570 m/z peak for a series of different analyte concentrations deposited on standard and carbon nanotube substrates. The nanotube substrates show consistently better signal. The inset images are SEM images of the crystal deposits on the CNT enhanced substrate that correspond to the data points. Signal to Noise Ratio in generic units.

The series of images inset in FIG. 34 are scanning electron microscope images of the samples that correspond to the data points on the graph. The morphology of the crystals changed over the range of concentrations, partially due to the different amounts of αCHCA matrix that was deposited with the analyte. At higher concentrations, the matrix produced large crystals with a defined, cubic structure. Below the 300 attomol level, the crystals are significantly smaller and more numerous, which theoretically provides an increase in the overall crystalline surface area. The change in the morphology of the crystals may account for the signal intensity increase in the center of the graph. Vorm et al. (Vorm, et al., *Improved Resolution and Very High-Sensitivity in Maldi Tof of Matrix Surfaces Made by Fast Evaporation*. Analytical Chemistry, 1994. 66(19): p. 3281-3287) reported a two order of magnitude increase in sensitivity due to a reduction in matrix crystal size using αCHCA. The increased surface area may permit greater flux of matrix and ionized analyte molecules to desorb from the sample surface when excited by the laser in the MALDI instrument.

The performance of AnchorChip™ plates has a published the detection limit for peptides deposited using αCHCA as the matrix. Analyte signal was detectable at 0.4 femtomoles for the dried droplet technique and 0.1 femtomoles for the SMW technique, with a signal to noise ratio between 5.5 and 39.5. The dried droplet deposition on patterned carbon nanotubes presented in this work was able to produce a quality signal (SNR of approximately 100) at 65 attomoles.

Carbon nanotube anchor spots were found to vastly improve MALDI-TOF-MS signal-to-noise ratios. An Applied Biosystems Voyager DE STR MALDI-TOF and nitrogen laser at 20 Hz firing frequency with 400 micron fiber coupling were used for these experiments. Glu-Fibrinopeptide samples were then digested and mixed in a 2.5 mg/ml HCCA matrix. 0.2 μL aliquots of 250 fmol/μL were applied to either the traditional Bruker support or the carbon nanotube target support and ionized by a laser and run through a mass spectrometer with the operating laser intensity set slightly above threshold levels, and an acquisition of 250 shots per spectrum. The samples were analyzed on single positions on the target support using a delayed-extraction mode (extraction delay 200 nanoseconds). Signal-to-noise ratios for 1570 m/z peak in a variety of analyte concentrations were recorded, as seen in FIG. 34. The nanotube-based anchor spot samples display at least a 3-5× better signal than the traditional Bruker support. The reason for the much stronger (~50×) signals at the 195 and 260 attomol samples is not known, but may lead to a further increase in sensitivity.

Figure 35:
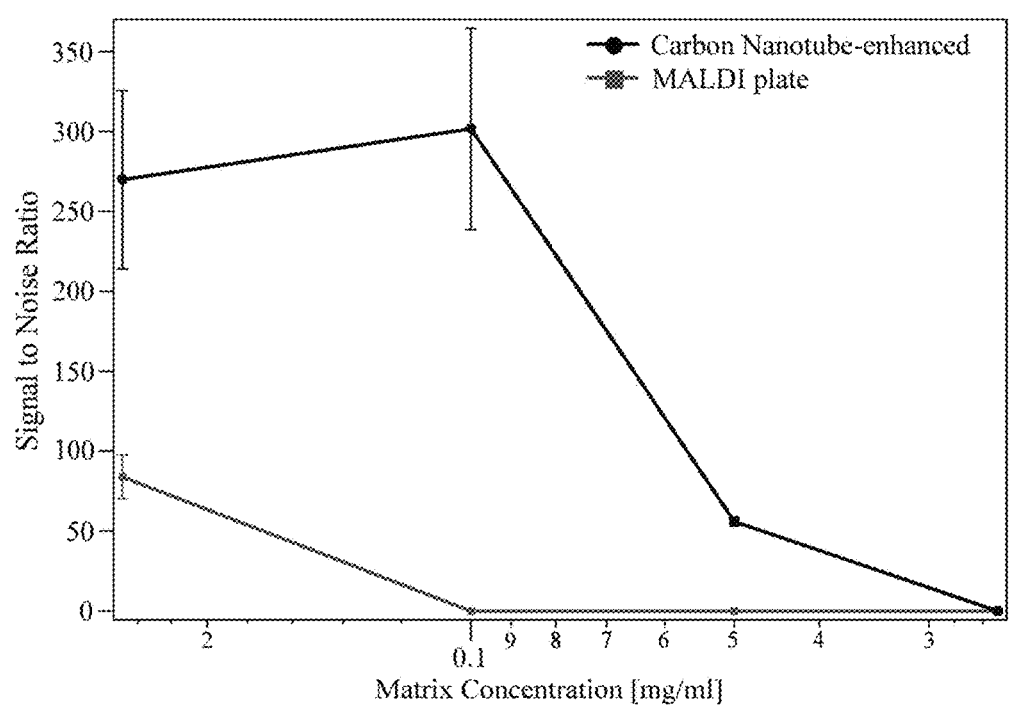
FIG. 35 is a graph comparing the MALDI-TOF-MS signal-to-noise ratio of the Glu-Fibrinopeptide 1570 m/z peak for a series of different matrix/analyte concentration ratios. The nanotube nucleation promoting anchor spots ("CNT") show consistently better signal, with the highest performance increase at lower matrix concentrations.

Moreover, at low matrix concentrations, carbon nanotube target supports greatly enhance signal-to-noise ratios compared to traditional Bruker supports, as seen in FIG. 35. Spots performances were compared for traditional Bruker supports and carbon nanotube target supports by suspending 2 fmol/μL Glu-Fibrinopeptide analyte was suspended in varying amounts of HCCA matrix from 0.25 mg/ml to 0.025 mg/ml. The matrix-to-analyte ratio was compared to signal-to-noise for both traditional Bruker supports and carbon nanotube target supports. The nanotube spots show consistently better performance than the standard plate control samples, and enhance the signal levels in samples with 0.1 mg/ml of matrix or less.

The data shown in FIGS. 34 and 35 represent the average of multiple samples that were prepared identically and investigated at the same time under the same conditions for each data point. As seen by the standard error bars of the mean for the collected data, the carbon nanotube supports significantly improve the signal to noise ration over conventional supports.

As seen in the examples, using a HCCA matrix the final deposit is spread over a much wider area than the anchor spot in traditional target supports. The reason for this behavior lies in the necessity to use an organic solvent mixable with water to dissolve the HCCA matrix. Acetonitrile is typically used as organic solvent as it dissolves HCCA and is sufficiently polar to mix with the aqueous analyte solution. The ensuing scenario after deposition is schematically shown in FIG. 11(A). The organic solvent evaporates first due to its higher vapor pressure than water, creating a supersaturation for the matrix molecules. This causes the matrix molecules to precipitate in situ around the anchor spot since the drop is still relatively large at that point, while in the same time collapsing due to the increased concentration. At the end of the evaporation process an area much larger than that of the anchor spot is coated with deposit, similar to drop depositions on a standard (non-anchor stainless steel) plate, as seen in FIG. 11(A). The MALDI laser spot can only interrogate a small fraction of the total deposit, resulting in most analyte never being analyzed by the mass spectrometer and limiting the total achievable sensitivity.

Figure 9:
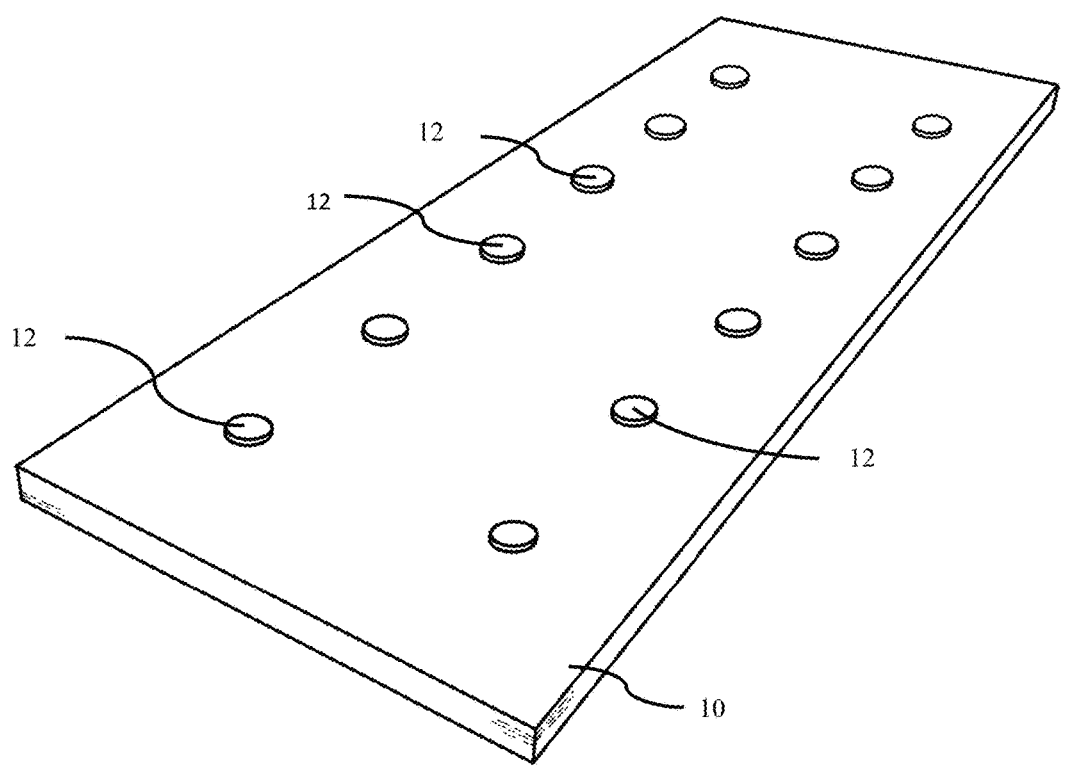
FIG. 9 is an isometric view of the target support wafer of the present invention showing the nickel catalyst seeds. The seed islands are enlarged compared to the wafer to allow visualization.

The carbon nanotubes provide an anchor spot which promotes selective nucleation of the matrix compound on the nanotube versus the surrounding area, avoiding supersaturation precipitation on the surrounding area. Deposition occurs exclusively on the anchor spot during the initial organic solvent evaporation phase, regardless of the area covered by the droplet, as seen in FIG. 11(B). This results in significant signal improvement as seen in FIG. 9. The nanotubes also demonstrated a much more reproducible analysis process. The small size of the deposit eliminates the "hunting" for signal, as every excitation from the laser yielded signal until analyte depletion occurred.

Example 9

Determination of threshold irradiance is important in MALDI sample processing. Setting the laser intensity too high can cause increased measurement noise and loss of mass resolution due to increased peak width. Laser intensity below the desorption threshold can lead to decline of analyte signal below a detectable level. Threshold irradiance for samples prepared on the standard MALDI plate and carbon nanotube-enhanced substrates was tested. The performance of carbon nanotube-enhanced substrates was tested over a range of laser intensities. The matrix and analyte concentrations used were 0.25 mg/mL (αCHCA) and 2.5 fmol/μL (peptide mixture 1) respectively. Two samples were prepared, one on a carbon nanotube spot (sample #1) and one on the standard MALDI plate (#43) using a deposition volume of 0.2 µL. Two other samples (#2 and #44) were prepared using a deposition volume of 0.5 µL in order to document any change in performance between the two sets of substrates with respect to deposition volume. Table 9 contains a summary of the sample configuration and dried droplet measurements.

TABLE 9

Deposition conditions and resulting dried droplet sizes.

| Sample | Substrate | Volume (µL) | Area (mm$^2$) | Diameter (mm) |
|---|---|---|---|---|
| 1 | CNT | 0.2 | 0.021 | 0.206 |
| 2 | CNT | 0.5 | 0.207 | 0.496 |
| 43 | MALDI plate | 0.2 | 0.651 | 1.104 |
| 44 | MALDI plate | 0.5 | 1.285 | 1.306 |

Laser intensity of the MALDI instrument was increased incrementally from 2000 to 2400 (arbitrary units given in the instrument control software), using a linear neutral density filter (attenuates laser energy). Spectra were collected from 250 interrogations at constant laser power for each step. Data Explorer software was used to analyze the spectra and produce SNR data. IGOR Pro was used to plot the data for the analyte signal from the des-Argininel-Bradykinin (904 m/z) peptide.

Figure 36:
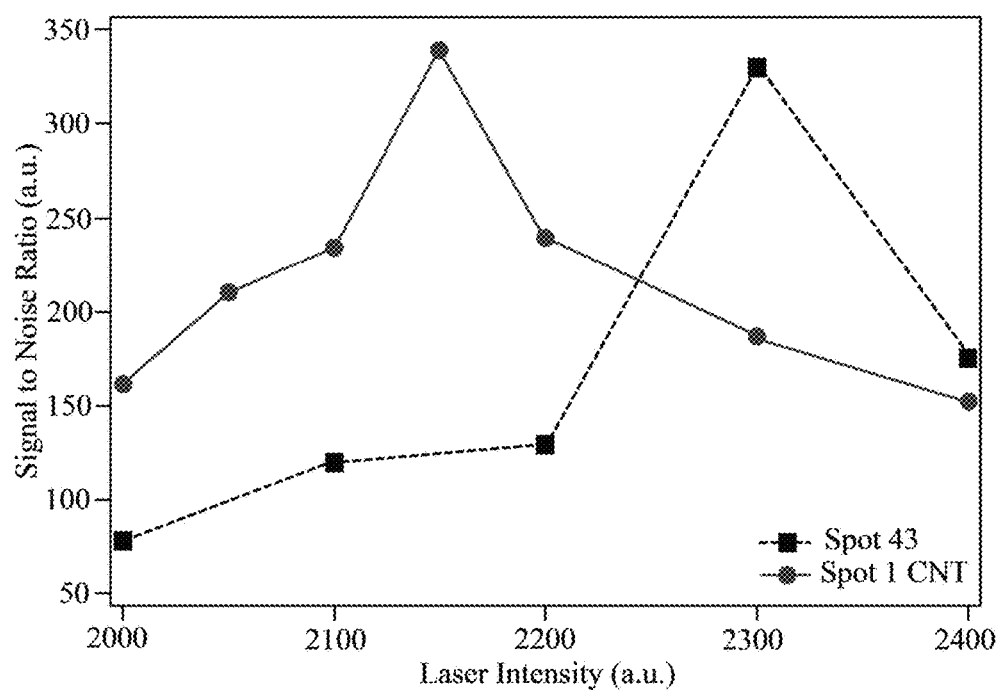
FIG. 36 is a graph showing signal-to-noise ratio (SNR) data (in generic units) versus laser intensity (in arbitrary units) for samples prepared with 0.2 μL of solution.

The data for spots 1 and 43 (0.2 µL deposition volume) was plotted in FIG. 36. The CNT-enhanced sample produced a slightly higher SNR (338.7 a.u.) than that of the standard sample (329.8 a.u.). However, the peak occurred at a lower laser intensity (2150 vs. 2300 a.u.), indicating increased efficiency of laser absorption and signal generation.

Figure 37:
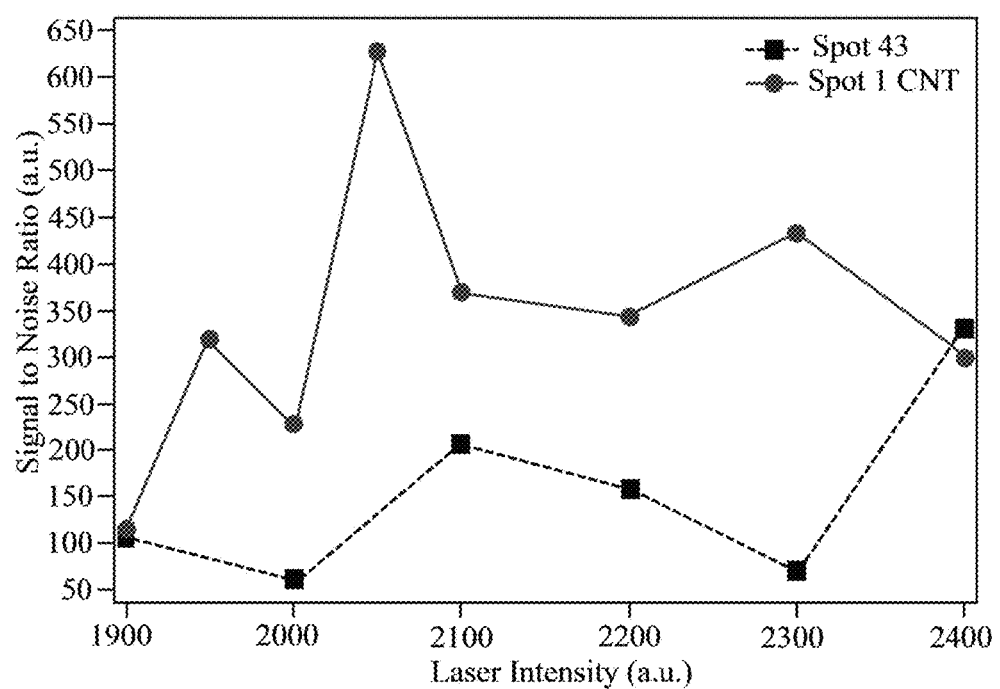
FIG. 37 is a graph showing signal-to-noise ratio (SNR) data (in generic units) versus laser intensity (in arbitrary units) for samples prepared with 0.5 μL of solution.
Figure 38A:
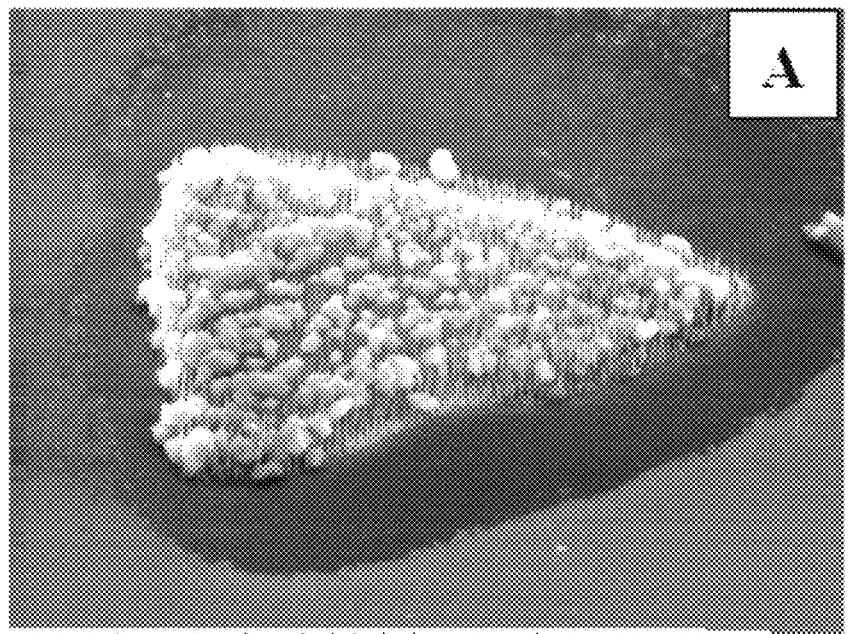
FIG. 38A is a scanning electron microscope (SEM) image of spot 1 after initial deposition.
Figure 38B:
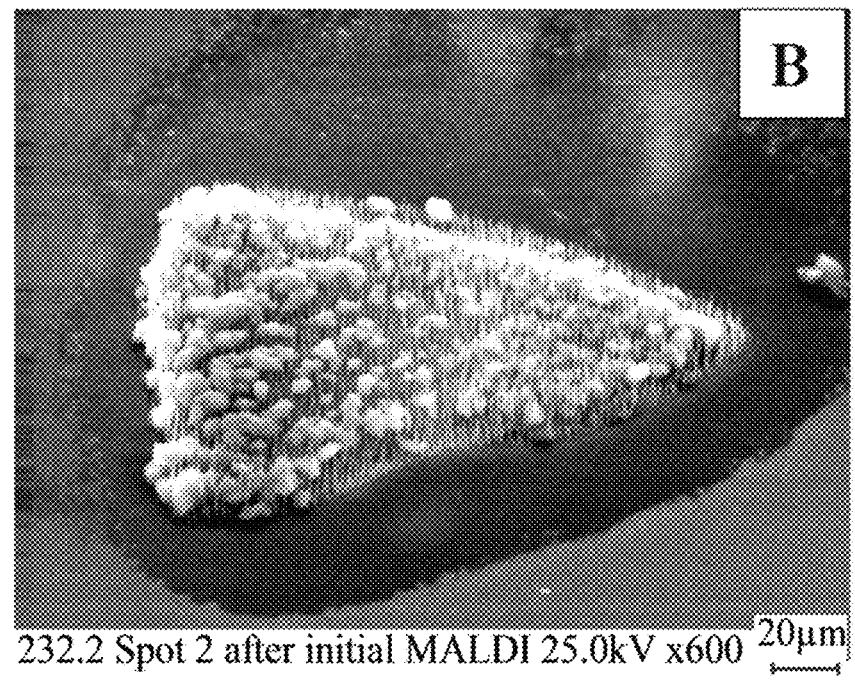
FIG. 38B is a scanning electron microscope (SEM) image of spot 1 after MALDI investigation.
Figure 38C:
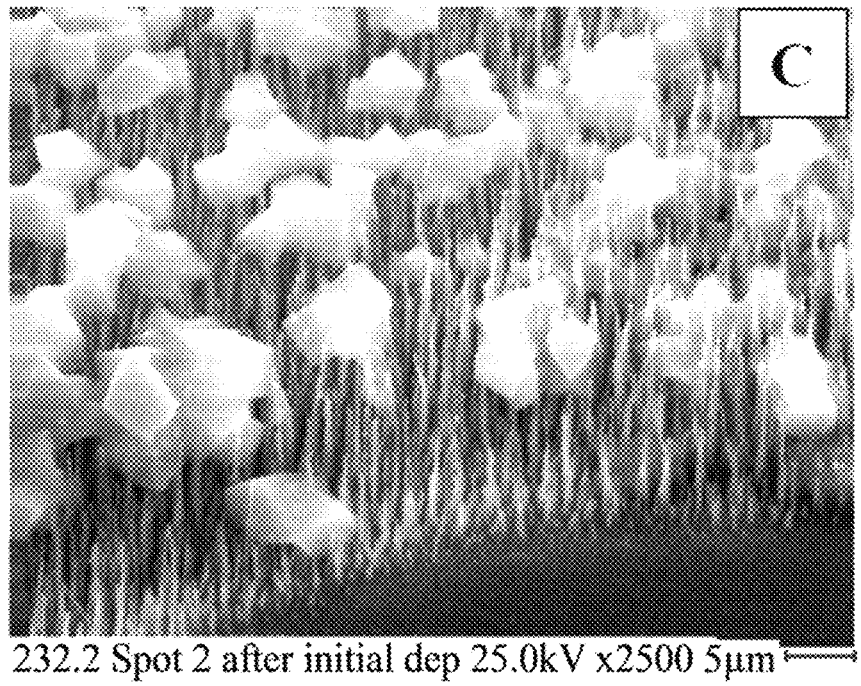
FIG. 38C is a scanning electron microscope (SEM) image of spot 1 after initial deposition at a higher magnification image than 38 A, illustrating change in crystal morphology.
Figure 38D:
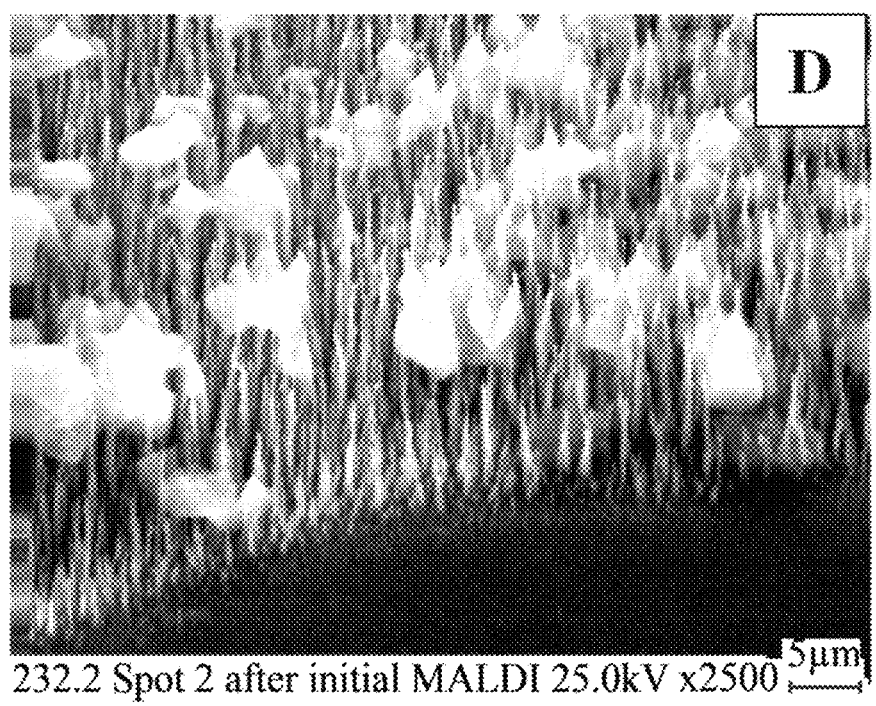
FIG. 38D is a scanning electron microscope (SEM) image of spot 1 after MALDI investigation at a higher magnification image than 38B, illustrating change in crystal morphology.

FIG. 37 graphs the data for spots 2 and 44 (0.5 µL deposition volume). The performance difference between the two samples is more pronounced (628.2 vs 329.7 a.u.). The SNR values for these samples are higher than those deposited with 0.2 µL possibly due to a larger quantity of matrix/analyte deposited on the sample. The fluctuations shown in the graph could be the result of variations in crystal formations over the larger dried droplet diameter.

The performance of the carbon nanotube-enhanced substrates is thought to be a result of lateral concentration of the matrix crystals into an area approximately the size of the laser beam at the point of investigation. This localization can increase inter-crystalline contact and maximize simultaneous interrogation, resulting in an enhancement of the ionization process through increased interaction of excitations, both on the sample surface and in the plume.

In addition to the standard optical microscopy, scanning electron microscopy was performed on spots 1 and 2 after the initial deposition and again after the series of MALDI interrogations. The difference in matrix crystal morphology illustrates the effect of the desorption process in removing material from the sample. The carbon nanotubes appear unchanged after the MALDI process. In the magnified images, FIGS. 38 (C) and (D), the tips of the carbon nanotubes can clearly be seen protruding from the matrix crystals, indicating matrix interaction with the nanotube surface. The results demonstrate the importance of laser intensity optimization for each sample to maximize SNR values. Excessive laser power can decrease mass resolution (known from literature) and can cause a change in crystal morphology as a result of the desorption process.

Utilizing patterned carbon nanotubes in the MALDI sample preparation process was shown to anchor the deposited liquid matrix/analyte solution and provide a seeding area for the growth of matrix crystals during the evaporation process. The ring-shaped crystallization pattern of matrix αCHCA deposited on a standard MALDI plate was replaced with preferential nucleation on the CNTs, when an identical solution was deposited on a carbon nanotube-enhanced substrate. Further, CNT-enhanced substrates provided droplet diameter reduction without significant deposition on the surrounding substrate. This was not due to residual catalyst or the silicon substrate, as no preferential nucleation was observed in either example, and deposition results were similar to a standard MALDI plate.

Results demonstrated that the carboxyl group did not interact with the carbon nanotubes in the same way as the hydroxyl group, possibly the result of fewer available bonding sites due to dimerization of carboxyl groups between the molecules in solution, Additionally, molecules without aromatic rings did not appear to interact with the nanotubes. Of the molecules tested, salicylic acid behaved in a similar manner as αCHCA, with preferential nucleation on the CNTs, and a similar reduction in the resulting dried droplet spot size.

Testing suggested that tubular image charge states (Granger, B. E., et al., *Highly extended image states around nanotubes*. Physical Review Letters, 2002. 89(13)) surrounding the nanotubes, as a result of the metallic-dominated conduction behavior typically associated with multi-wall carbon nanotubes, may be a dominant mechanism for the observed preferential nucleation. The effectiveness of the carbon nanotube-enhanced substrate can be dependent on matrix concentration. For concentrations in the low and medium range, crystallization occurred primarily on the nanotubes. However, for concentrations approaching saturation of solution, the overabundance of material lead to deposition on the CNT's and the surrounding areas, and the average crystal size increased significantly.

The improved sample concentrating ability of the carbon nanotube-enhanced substrate over the standard MALDI plate was demonstrated by increased signal to noise ratios for all four peptides contained in the analyte mixture. The performance increase was attributed to lateral matrix and analyte concentration on the sample surface due to preferential nucleation. Increased contact between the crystals could provide a path for pooling of excited states, thereby increasing efficiency of desorption and localized ionization.

For samples prepared with low concentrations of analyte, the carbon nanotube-enhanced substrate demonstrated better performance over the tested range than the standard MALDI plate, with signal to noise ratio increases from 2× to 5×. The CNT-enhanced substrate produced a quality signal at the lowest concentration tested, 65 attomoles. Optimal substrate performance corresponded to crystal morphology that was small and numerous instead of large and connected, attributed to increased crystal surface area contributing to enhanced laser absorption and increased molecular desorption. The increase in analyte signal at this concentration may indicate that crystal surface area is a more dominant mechanism for desorption than exciton pooling.

The importance of optimized laser intensity for maximum signal to noise data was demonstrated by variation of the laser intensity with subsequent MALDI interrogations. This process also verified that the concentrating effect of the CNT-enhanced substrate reduced the required intensity for maximum SNR. This is thought to be the result of molecular localization, increased energy pooling, and the increased number of crystals interrogated simultaneously, compared to the samples deposited on the standard MALDI plate. Scanning electron microscopy was used to study crystal morphology, as images that were taken of the matrix crystals before and after the experiment displayed the effect of desorption at high laser intensities as the crystals appeared reduced in size and less numerous.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of mass spectrometer anchors, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

---

---

What is claimed is:

1. A mass spectrometry analyte support, comprising:
a support wafer comprising at least an analysis face;
at least one analyte anchor disposed on the analysis face, the at least one analyte anchor comprising a plurality of carbon nanotubes aligned perpendicularly to the analysis face, wherein the at least one analyte anchor has a diameter of about 150 µm to about 200 µm; and
a dissolved analyte-matrix solution preferentially nucleated on the plurality of carbon nanotubes of the support wafer, wherein the dissolved analyte-matrix solution comprises an analyte and a water-insoluble matrix dissolved in a mixture of water and organic solvent.

2. The mass spectrometry analyte support of claim 1, wherein the support wafer is a silicon wafer.

3. The mass spectrometry analyte support of claim 2, wherein the support wafer is coated with a hydrophobic material.

4. The mass spectrometry analyte support of claim 1, wherein the plurality of carbon nanotubes have an average length of 2.5 μm.

5. The mass spectrometry analyte support of claim 1, wherein the plurality of carbon nanotubes have an average width of 110 nm.

6. A method of creating a mass spectrometry analyte support, comprising the steps of:
providing a matrix-assisted laser desorption/ionization support wafer further comprising at least an analysis face;
patterning at least one metal catalyst island on the analysis face of the matrix-assisted laser desorption/ionization support wafer, wherein the metal catalyst island has a diameter of about 150 μm to about 200 μm;
reducing the ambient pressure surrounding the matrix-assisted laser desorption/ionization support wafer;
exposing the matrix-assisted laser desorption/ionization support wafer to ammonia;
exposing the matrix-assisted laser desorption/ionization support wafer to a carbon source;
growing a plurality of aligned carbon nanotubes disposed perpendicular to the matrix-assisted laser desorption/ionization support wafer on the patterned at least one metal catalyst island by plasma enhanced chemical vapor deposition;
dissolving a water-insoluble matrix in a mixture of water and organic solvent;
adding an analyte to the matrix solution;
applying the dissolved analyte-matrix solution to the support wafer; and
nucleating the dissolved analyte-matrix solution on the nanotubes of the support wafer, wherein the dissolved analyte preferentially nucleates on the plurality of nanotubes of the at least one metal catalyst island.

7. The method of claim 6, further comprising annealing the metal catalyst to the matrix-assisted laser desorption/ionization support wafer by warming the support wafer-metal catalyst at 200° C. for 24 hours.

8. The method of claim 6, wherein the matrix-assisted laser desorption/ionization support wafer is a silicon wafer.

9. The method of claim 6, wherein the metal catalyst island is selected from the group consisting of iron, iron and molybdenum, cobalt, cobalt and molybdenum, and nickel.

10. The method of claim 9, wherein the metal catalyst island is patterned on the matrix-assisted laser desorption/ionization support wafer at a thickness of between 10 nm and 40 nm.

11. The method of claim 6, wherein the carbon source is selected from the group consisting of methane, carbon oxide, hexane, acetylene, carbon dioxide, benzene, and ethanol.

12. The method of claim 11, wherein the carbon source is gaseous acetylene, and ammonia and wherein a ratio of the ammonia to gaseous acetylene ratio is 4:1.

13. The method of claim 8, further comprising cleaning the silicon wafer using a sequential rinse of acetone, isopropyl alcohol, and methanol; and
drying the silicon wafer with nitrogen after cleaning the silicon wafer.

14. The method of claim 6, where growing the plurality of aligned carbon nanotubes further comprises growing the plurality of aligned carbon nanotubes at a temperature between 500° C. and 1200° C.

15. The method of claim 6, where reducing the ambient pressure further comprises reducing the ambient pressure to $1 \times 10^{-3}$ Torr.

16. The method of claim 6, wherein patterning the catalyst further comprises patterning the catalyst using electron beam deposition.

17. The method of claim 16, wherein the electron beam deposition is performed using a 270° deflection of an electron beam source from a crucible.

18. The method of claim 16, wherein the electron beam deposition is performed at $1 \times 10^{-6}$ Torr.

19. The method of claim 6, further comprising allowing the plurality of aligned carbon nanotubes disposed perpendicular to the matrix-assisted laser desorption/ionization support wafer to cool to room temperature in vacuum.

* * * * *